US010004704B2

(12) United States Patent
Bannister et al.

(10) Patent No.: US 10,004,704 B2
(45) Date of Patent: *Jun. 26, 2018

(54) COMPOSITIONS AND METHODS FOR TREATING CHRONIC INFLAMMATION AND INFLAMMATORY DISEASES

(71) Applicant: Infirst Healthcare Limited, London (GB)

(72) Inventors: Robin Mark Bannister, Essex (GB); John Brew, Hertfordshire (GB); Wilson Caparros-Wanderley, Buckinghamshire (GB); Gregory Alan Stoloff, London (GB); Suzanne Jane Dilly, Oxfordshire (GB); Gemma Szucs, Oxfordshire (GB); Olga Pleguezuelos Mateo, Bicester (GB)

(73) Assignee: Infirst Healthcare Limited, London (GB)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/169,619

(22) Filed: May 31, 2016

(65) Prior Publication Data

US 2016/0271088 A1 Sep. 22, 2016

Related U.S. Application Data

(63) Continuation of application No. 14/520,150, filed on Oct. 21, 2014, now Pat. No. 9,381,180, which is a continuation of application No. 13/365,824, filed on Feb. 3, 2012, now Pat. No. 8,895,536, which is a continuation-in-part of application No. PCT/GB2011/052115, filed on Oct. 31, 2011.

(30) Foreign Application Priority Data

| Oct. 29, 2010 | (GB) | 1018289.7 |
| Feb. 4, 2011 | (GB) | 1101937.9 |
| Aug. 10, 2011 | (GB) | 1113728.8 |
| Aug. 10, 2011 | (GB) | 1113729.6 |
| Aug. 10, 2011 | (GB) | 1113730.4 |

(51) Int. Cl.
| A61K 31/19 | (2006.01) |
| A61K 31/192 | (2006.01) |
| A61K 9/08 | (2006.01) |
| A61K 47/44 | (2017.01) |
| A61K 9/20 | (2006.01) |
| A61K 31/60 | (2006.01) |
| A61K 47/10 | (2017.01) |
| A61K 47/14 | (2017.01) |
| A61K 47/34 | (2017.01) |
| A61K 31/215 | (2006.01) |
| A61K 31/22 | (2006.01) |
| A61K 31/40 | (2006.01) |
| A61K 31/216 | (2006.01) |

(52) U.S. Cl.
CPC ............. *A61K 31/192* (2013.01); *A61K 9/08* (2013.01); *A61K 9/2013* (2013.01); *A61K 31/60* (2013.01); *A61K 47/10* (2013.01); *A61K 47/14* (2013.01); *A61K 47/34* (2013.01); *A61K 47/44* (2013.01); *A61K 31/19* (2013.01); *A61K 31/215* (2013.01); *A61K 31/216* (2013.01); *A61K 31/22* (2013.01); *A61K 31/40* (2013.01)

(58) Field of Classification Search
CPC .............................. A61K 31/192; A61K 31/19
USPC .............................. 514/570, 571, 557
See application file for complete search history.

(56) References Cited

U.S. PATENT DOCUMENTS

| 3,228,831 A | 1/1966 | Nicholson et al. |
| 3,800,038 A | 3/1974 | Rudel |
| 4,571,400 A | 2/1986 | Arnold |
| 4,684,666 A | 8/1987 | Haas |
| 4,918,103 A | 4/1990 | Park et al. |
| 5,011,852 A | 4/1991 | Park et al. |
| 5,059,626 A | 10/1991 | Park et al. |
| 5,154,930 A | 10/1992 | Nicholson et al. |
| 5,552,160 A | 9/1996 | Liversidge et al. |
| 5,645,856 A | 7/1997 | Lacy et al. |
| 5,955,451 A | 9/1999 | Lichtenberger et al. |
| 6,214,386 B1 | 4/2001 | Santus |
| 6,264,981 B1 | 7/2001 | Zhang |
| 6,267,985 B1 | 7/2001 | Chen et al. |
| 6,294,192 B1 | 9/2001 | Patel et al. |
| 6,319,513 B1 | 11/2001 | Dobrozsi |
| 6,383,471 B1 | 5/2002 | Chen et al. |

(Continued)

FOREIGN PATENT DOCUMENTS

| CN | 1736369 | 2/2006 |
| CN | 1736369 A | 2/2006 |

(Continued)

OTHER PUBLICATIONS

Csizmazia, E., et al., Penetration enhancer effect of sucrose laurate and Transcutol on ibuprofen, Journal of Drug Delivery Science and Technology, vol. 21, No. 5 Sep. 2011 XP009168551.
Hesson Chung, et al., Oil Components Modulate Physical Characteristics of the Natural Oil Emulsions as Drug or Gene Delivery System, Journal of Controlled Release 71:339-350 (2001).
List et al., Hydrogenation of Soybean Oil Triglycerides: Effect of Pressure on Selectivity. JAOCS (2000), vol. 77, pp. 311-314.
PCT International Preliminary Report on Patentability, PCT/GB2011/050189, pp. 11 (dated Aug. 7, 2012).
PCT International Preliminary Report on Patentability, PCT/GB2011/052115, pp. 8 (dated Apr. 30, 2013).
PCT International Search Report and The Written Opinion of the Internation Searching Authority PCT/EP2014/050627.

(Continued)

*Primary Examiner* — Kevin E Weddington
(74) *Attorney, Agent, or Firm* — Ultimatedge IP Law Group, P.C.; Dean G. Stathakis

(57) ABSTRACT

The present specification discloses pharmaceutical compositions, methods of preparing such pharmaceutical compositions, and methods and uses of treating a chronic inflammation and/or an inflammatory disease in an individual using such pharmaceutical compositions.

24 Claims, 4 Drawing Sheets

(56) References Cited

U.S. PATENT DOCUMENTS

| | | |
|---|---|---|
| 6,451,339 B2 | 9/2002 | Patel et al. |
| 6,455,067 B1 | 9/2002 | Woo et al. |
| 6,923,988 B2 | 8/2005 | Patel et al. |
| 7,473,432 B2 | 1/2009 | Cevc et al. |
| 8,663,692 B1 | 5/2014 | Muller et al. |
| 8,895,536 B2 * | 11/2014 | Bannister ............... A61K 9/08 514/159 |
| 8,895,537 B2 | 11/2014 | Bannister |
| 9,265,742 B2 * | 2/2016 | Bannister ............. A61K 31/192 |
| 9,271,950 B2 * | 3/2016 | Bannister ............... A61K 9/08 |
| 9,308,213 B2 | 4/2016 | Bannister |
| 9,326,958 B2 | 5/2016 | Bannister |
| 9,381,180 B2 * | 7/2016 | Bannister ............... A61K 9/08 |
| 9,427,422 B2 | 8/2016 | Bannister |
| 9,504,664 B2 * | 11/2016 | Bannister ............. A61K 31/192 |
| 9,693,980 B2 | 7/2017 | Bannister et al. |
| 9,737,500 B2 | 8/2017 | Bannister et al. |
| 9,744,132 B2 | 8/2017 | Bannister et al. |
| 9,750,810 B2 | 9/2017 | Bannister et al. |
| 9,775,820 B2 | 10/2017 | Bannister et al. |
| 9,789,075 B2 | 10/2017 | Bannister et al. |
| 9,795,577 B2 | 10/2017 | Bannister et al. |
| 9,820,952 B2 | 11/2017 | Bannister et al. |
| 9,827,215 B2 | 11/2017 | Bannister et al. |
| 2001/0005726 A1 | 6/2001 | Woo et al. |
| 2001/0006650 A1 | 7/2001 | Burnside et al. |
| 2003/0008003 A1 | 1/2003 | Jamali |
| 2003/0170279 A1 | 9/2003 | Lambert et al. |
| 2003/0232097 A1 | 12/2003 | Radhakrishnan et al. |
| 2004/0024057 A1 | 2/2004 | Earl et al. |
| 2004/0253276 A1 | 12/2004 | Sato et al. |
| 2005/0152968 A1 | 7/2005 | Brophy et al. |
| 2006/0034937 A1 | 2/2006 | Patel |
| 2006/0062810 A1 | 3/2006 | Woo et al. |
| 2006/0078616 A1 | 4/2006 | Georgewill et al. |
| 2007/0015834 A1 | 1/2007 | Flashner-Barak et al. |
| 2007/0026062 A1 | 2/2007 | Holm et al. |
| 2007/0036831 A1 | 2/2007 | Baker |
| 2007/0048284 A1 | 3/2007 | Donahue et al. |
| 2007/0048384 A1 | 3/2007 | Rosenberg et al. |
| 2007/0092559 A1 | 4/2007 | Yuan |
| 2007/0104741 A1 | 5/2007 | Murty et al. |
| 2007/0105912 A1 | 5/2007 | Holm et al. |
| 2007/0190080 A1 | 8/2007 | Friedman |
| 2007/0203173 A1 | 8/2007 | Mudumba et al. |
| 2008/0153894 A1 | 6/2008 | Britten et al. |
| 2008/0154210 A1 | 6/2008 | Jordan et al. |
| 2009/0304782 A1 | 12/2009 | De Bias et al. |
| 2010/0068276 A1 | 3/2010 | Friesen et al. |
| 2010/0099767 A1 | 4/2010 | Davis |
| 2010/0125060 A1 | 5/2010 | Razzak et al. |
| 2011/0142945 A1 | 6/2011 | Chen et al. |
| 2011/0195993 A1 | 8/2011 | Masson et al. |
| 2012/0270845 A1 | 10/2012 | Bannister et al. |
| 2012/0270899 A1 | 10/2012 | Bannister et al. |
| 2013/0156853 A1 | 6/2013 | Zhang et al. |
| 2013/0178448 A1 | 7/2013 | Bannister et al. |
| 2014/0128353 A1 | 5/2014 | Bannister et al. |
| 2014/0162987 A1 | 6/2014 | Bannister et al. |
| 2014/0162988 A1 | 6/2014 | Bannister et al. |

FOREIGN PATENT DOCUMENTS

| | | |
|---|---|---|
| CN | 101129335 A | 2/2008 |
| CN | 102793628 A | 11/2012 |
| EP | 306060 A2 | 3/1989 |
| EP | 0521344 A2 | 1/1993 |
| EP | 1923060 A1 | 5/2008 |
| FR | 2810243 A1 | 12/2001 |
| GB | 2331458 A | 5/1999 |
| GB | 2477590 A | 8/2011 |
| JP | 6009381 | 3/1992 |
| JP | 2008143807 | 12/2006 |
| JP | 2009155282 | 7/2009 |
| WO | 198600802 A1 | 2/1986 |
| WO | 198600802 A1 | 2/1986 |
| WO | 92/09272 A1 | 6/1992 |
| WO | 1995/011039 A1 | 4/1995 |
| WO | 1997003655 A1 | 2/1997 |
| WO | 1998000169 A1 | 1/1998 |
| WO | 1998/025595 A1 | 6/1998 |
| WO | 1998/025595 A2 | 6/1998 |
| WO | 1999006024 A1 | 2/1999 |
| WO | 2000/27372 A1 | 5/2000 |
| WO | 2000057859 A1 | 5/2000 |
| WO | 00/67728 A2 | 11/2000 |
| WO | 00/76478 A1 | 12/2000 |
| WO | 2002/085414 A2 | 10/2002 |
| WO | 2003/013566 A1 | 2/2003 |
| WO | 2004/082588 A2 | 9/2004 |
| WO | 2005/009436 A1 | 2/2005 |
| WO | 2006037348 A1 | 4/2006 |
| WO | 2006057903 A2 | 6/2006 |
| WO | 2006/096806 A2 | 9/2006 |
| WO | 2006/099325 A2 | 9/2006 |
| WO | 2006115463 A1 | 11/2006 |
| WO | 2008/070950 A1 | 6/2008 |
| WO | 2008/120207 A3 | 10/2008 |
| WO | 2008/134512 A1 | 11/2008 |
| WO | 2009/033131 A2 | 3/2009 |
| WO | 2009/047785 A3 | 4/2009 |
| WO | 2009/067734 A1 | 6/2009 |
| WO | 2009/069139 A1 | 6/2009 |
| WO | 2010/059717 A2 | 5/2010 |
| WO | 2010/087947 A2 | 8/2010 |
| WO | 2010/097332 A1 | 9/2010 |
| WO | 2010/097334 A1 | 9/2010 |
| WO | 2010103312 A1 | 9/2010 |
| WO | 2011/095814 A1 | 8/2011 |
| WO | 2012/056251 A1 | 5/2012 |
| WO | 2012/104654 A1 | 8/2012 |
| WO | 2012/104655 A2 | 8/2012 |
| WO | 2012127037 A2 | 9/2012 |
| WO | 2014108569 A1 | 7/2014 |
| WO | 2014108572 A1 | 7/2014 |
| WO | 2014108573 A1 | 7/2014 |
| WO | 2014108574 A1 | 7/2014 |
| WO | 2014117999 A1 | 8/2014 |
| WO | 2017025517 A1 | 2/2017 |

OTHER PUBLICATIONS

PCT International Search Report and the Written Opinion of the Internation Searching Authority PCT/EP2014/050628.

PCT International Search Report and the Written Opinion of the Internation Searching Authority PCT/EP2014/050637.

PCT International Search Report & Written Opinion, PCTGB2012050241, pp. 24 (dated Jul. 13, 2012).

PCT International Search Report & Written Opinion, PCTGB2012050242, pp. 12 (dated Jan. 22, 2013).

Strickley, Solubilizing Excipients in Oral and Inkectable Formulations Pharaceutical (2004), vol. 21, pp. 21, pp. 201-230.

Wolfgang Grebe, et al., A Multicenter, Randomized, Double-Blind, Double-Dummy, Placebo- and Active-Controlled, Parallel-Group Comparison of Diclofenac-K and Ibuprofen for the Treatment of Adults with Influenza-like Symptoms, Clinical Therapeutics 25(2): 444-459 (2003).

BASF Monomuls® 90-L 12, Personal Care BASF, Product Details, 4 pages.

Department of Health and Human Services, Attachment 3: Stability Background and Data Presentation, (Downloaded Jan. 15, 2015) 8 p.

Elburg, (Elburg Global, Hydrogenated Coconut Oil (Aug. 4, 2010), (retrieved from internet <URL: http://www.elburgglobal.nl/fileadmin/brochures/PDS_Hydr._Coconut_oil.pdf>), 1 page).

International Preliminary Report on Patentability and Written Opinion PCT/EP2014/050627, dated Aug. 4, 2015.

Juarez-Soberanez, et al., Gelucire 39/01 as excipient gastroretentive metronidazole sustained delivery, International Journal of Pharmacy and Pharmaceutical Sciences, (2011), vol. 3, Supp. 2, pp. 86-91.

(56) References Cited

OTHER PUBLICATIONS

Sharma, et al., Preparation and Characterization of Meloxicam—Myrj-52 Granules Obtained by Melt Granulation, PharmaTech, (2007).
Vane Jr et al., Mechanism of action of anti-inflammatory drugs, Int J Tissue React. 1998;20(1):3-15, abstract.
WHC (WHC, Welch, Holme & Clark Co., Inc., Partially Hydrogenated Soybean Oil, (Retrieved from internet <URL://http://whc-oils.com/hydrogenated-soybean-oil_html>), (downloaded).
Zeberg-Mikkelsen, et al., Predicting the melting points and the enthalpies of fusion of saturated triglycerides by a group contribution method, Fluid Phase Equilibria (1999), 162: 7-17.
Gattefosse, Maisine 35-1, Physicochemical Data Sheet (PCS), pp. 2 (last updated Nov. 28, 2013).
Gattefosse, Range of Products, URL: https://www.gattefosse.com/range-of-products#oral, pp. 5 (downloaded Jun. 22, 2017).
Haw, The HLB System, A Time Saving Guide to Surfactant Selection, Presentation to the Midwest Chapter of the Society of Cosmetic Chemists, Uniqema, URL: http://www.lotioncrafter.com/pdf/The_HLB_System.pdf, pp. 40 (2004).
Herbarie, Emulsifiers with HLB Values, URL: http://www.theherbarie.com/files/resource-center/formulating/Emulsifiers_HLB_Values.pdf, pp. 3 (downloaded Oct. 30, 2017).
ICI Americas, Inc., The HLB System, A Time-Saving Guide to Emulsifer Selection, pp. 22 (1980).
Jain, et al., Development of Gelucire 43/01 Beads od Metformin Hydrochloride for Floating Delivery, AAPS Pharm. Sci. Tech. 10(4): 1128-1136 (2009).
Khatri, Home Remedies for Ulcers, URL: http://www.steadyhealth.com/articles/homeremedies-for-ulcers, pp. 4 (downloaded Jun. 20, 2017).
Monzir-Pal, Characteristics of Surfactants and Emulsions, URL: http://www.monzirpal.net/Industrial/Characteristics%20of%20Surfactants%20and%20Emulsions.htm, pp. 8 (downloaded Jul. 26, 2015).
PCT Form ISA 210, International Search Report, PCT/GB2011/050189, pp. 7 (dated Jul. 1, 2011).
PCT Form ISA 237, Written Opinion, PCT/GB2011/050189, pp. 10 (dated Jul. 1, 2011).
PCT Form ISA 210, International Search Report, PCT/GB2011/052115, pp. 4 (dated Feb. 13, 2011).
PCT Form ISA 237, Written Opinion, PCT/GB2011/052115, pp. 7 (dated Feb. 13, 2011).
PCT Form IB 373, International Preliminary Report on Patentability, PCT/GB2012/050241, pp. 11 (dated Aug. 6, 2013).
PCT Form IB 373, International Preliminary Report on Patentability, PCT/GB2012/050242, pp. 12 (dated Aug. 6, 2013).
PCT Form IB 373, International Preliminary Report on Patentability, PCT/EP2014/050628, pp. 7 (dated Jul. 1, 2015).
PCT Form ISA 210, International Search Report, PCT/EP2014/050636, pp. 4 (dated Apr. 3, 2014).
PCT Form ISA 237, Written Opinion, PCT/EP2014/050636, pp. 6 (dated Apr. 3, 2014).
PCT Form IB 373, International Preliminary Report on Patentability, PCT/EP2014/050636, pp. 7 (dated Jul. 14, 2015).
PCT Form IB 373, International Preliminary Report on Patentability, PCT/EP2014/050637, pp. 25 (dated Apr. 8, 2015).
PCT Form ISA 210, International Search Report, PCT/EP2014/050638, pp. 4 (dated Apr. 3, 2014).
PCT Form ISA 237, Written Opinion, PCT/EP2014/050638, pp. 6 (dated Apr. 3, 2014).
PCT Form IB 373, International Preliminary Report on Patentability, PCT/EP2014/050638, pp. 7 (dated Jul. 14, 2015).
PCT Form ISA 210, International Search Report, PCT/EP2016/068900, pp. 3 (dated Oct. 26, 2016).
PCT Form ISA 237, Written Opinion, PCT/EP2016/068900, pp. 6 (dated Oct. 26, 2016).
PubChem, 1-Linoleoyl-(2S)-glycerol, URL: https://pubchem.ncbi.nlm.nih.gov/compound/6436630, pp. 20 (last modified Nov. 4, 2017).
PubChem, 1-Monolinolein, URL: https://pubchem.ncbi.nlm.nih.gov/compound/1-Monolinolein, pp. 20 (last modified Nov. 4, 2017).
Ren, et al., Optimization of Self Nanoemulsifying Drug Delivery System for Poorly Water-Soluble Drug using Response Surface Methodology, Drug. Dev. Ind. Pharm. 39(5): 799-806 (2013).
Shen, et al., Effects of Core Tablet Size on the Functionality of Aqueous Delayed Release Coatings as Measured by SEM and LIBS, ACRYL-EZE MP, Poster Reprint (2010).
SIGMA-ALDRICH (Millipore Sigma), Surfactants Classified by HLB Numbers, URL: https://www.sigmaaldrich.com/materials-science/material-science-products.html?T ablePage=22686648, pp. 4 (downloaded Oct. 30, 2017).
Sinha, et al., Solid Dispersion as an Approach for Bioavailability Enhancement of Poorly Water-Soluble Drugs Ritonavir, AAPS Pharm. Sci. Tech. 11(2): 518-527 (2010).
Wikipedia, Monoglyceride, URL: https://en.wikipedia.org/wiki/Monoglyceride, pp. 3 (last edited Oct. 15, 2017).
U.S. Appl. No. 13/365,824, filed Feb. 3, 2012, Feb. 4, 2011, US 20120270845, U.S. Pat. No. 8,895,536.
U.S. Appl. No. 13/365,828, filed Feb. 3, 2012, Feb. 4, 2011, US 20120270899, U.S. Pat. No. 8,895,537.
U.S. Appl. No. 13/576,758, filed Dec. 14, 2012, Feb. 5, 2010, US 20130178448.
U.S. Appl. No. 14/155,042, filed Jan. 14, 2014, Feb. 4, 2011, US 20140155485, U.S. Pat. No. 9,271,950.
U.S. Appl. No. 14/155,808, filed Jan. 14, 2014, Feb. 4, 2011, US 20140128354, U.S. Pat. No. 9,265,742.
U.S. Appl. No. 14/155,108, filed Jan. 14, 2014, Feb. 4, 2011, US 20140162988, U.S. Pat. No. 9,308,213.
U.S. Appl. No. 14/155,147, filed Jan. 14, 2014, Feb. 4, 2011, US 20140128353.
U.S. Appl. No. 14/155,167, filed Jan. 14, 2014, Feb. 4, 2011, US 20140162987.
U.S. Appl. No. 14/520,141, filed Oct. 21, 2014, Feb. 4, 2011, US 20150051281, U.S. Pat. No. 9,326,958.
U.S. Appl. No. 14/520,150, filed Oct. 21, 2014, Feb. 4, 2011, US 20150051287, U.S. Pat. No. 9,381,180.
U.S. Appl. No. 14/520,159, filed Oct. 21, 2014, Feb. 4, 2011, US 20150051235, U.S. Pat. No. 9,427,422.
U.S. Appl. No. 14/821,687, filed Aug. 7, 2015, Feb. 4, 2011, US 20150342880, U.S. Pat. No. 9,744,132.
U.S. Appl. No. 14/975,559, filed Dec. 18, 2015, Feb. 4, 2011, US 20160101077, U.S. Pat. No. 9,504,664.
U.S. Appl. No. 14/975,608, filed Dec. 18, 2015, Feb. 4, 2011, US 20160101180, U.S. Pat. No. 9,737,500.
U.S. Appl. No. 15/043,327, filed Feb. 12, 2016, Feb. 4, 2011, US 20160158361.
U.S. Appl. No. 15/061,661, filed Jan. 14, 2014, Feb. 4, 2011, US 20160199327.
U.S. Appl. No. 15/169,617, filed May 31, 2016, Feb. 4, 2011, US 20160271087, U.S. Pat. No. 9,693,980.
U.S. Appl. No. 15/169,619, filed May 31, 2016, Feb. 4, 2011, US 20160271088.
U.S. Appl. No. 15/195,608, filed Jun. 28, 2016, Feb. 4, 2011, US 20160303060.
U.S. Appl. No. 15/195,623, filed Jun. 28, 2016, Feb. 4, 2011, US 20160317482.
U.S. Appl. No. 15/219,245, filed Jul. 25, 2016, Feb. 4, 2011, US 20160331706, U.S. Pat. No. 9,789,075.
U.S. Appl. No. 15/289,083, filed Oct. 7, 2016, Feb. 4, 2011, US 20170043016.
U.S. Appl. No. 15/295,933, filed Oct. 17, 2016, Feb. 4, 2011, US 20170027895, U.S. Pat. No. 9,795,577.
U.S. Appl. No. 15/614,592, filed Jun. 5, 2017, Feb. 4, 2011, US 20170266287.
U.S. Appl. No. 15/684,197, filed Aug. 23, 2017, Feb. 4, 2011, US 20170348262.
U.S. Appl. No. 15/684,214, filed Aug. 23, 2017, Feb. 4, 2011, US 20170360702.
U.S. Appl. No. 15/702,440, filed Sep. 12, 2017, Feb. 4, 2011, US 20180000763.
U.S. Appl. No. 15/794,178, filed Oct. 26, 2017, Feb. 4, 2011.
U.S. Appl. No. 15/794,197, filed Oct. 26, 2017, Feb. 4, 2011.

(56) References Cited

OTHER PUBLICATIONS

U.S. Appl. No. 15/794,214, filed Oct. 26, 2017, Feb. 4, 2011.
U.S. Appl. No. 14/155,080, filed Jan. 14, 2014, Feb. 4, 2011, US 20140128354, U.S. Pat. No. 9,265,742.
U.S. Appl. No. 14/975,599, filed Dec. 18, 2015, Feb. 4, 2011, US 20160101077, U.S. Pat. No. 9,504,664.

* cited by examiner

COMPOSITIONS AND METHODS FOR TREATING CHRONIC INFLAMMATION AND INFLAMMATORY DISEASES

This continuation application claims priority pursuant to 35 U.S.C. § 120 to U.S. patent application Ser. No. 14/520,150, filed Oct. 21, 2014, a continuation that claims priority to U.S. patent application Ser. No. 13/365,824, filed Feb. 3, 2012, now U.S. Pat. No. 8,895,536, a continuation-in-part application that claims priority to patent application PCT/GB2011/052115, filed Oct. 31, 2011, an international patent application that claims priority to GB 1018289.7, filed Oct. 29, 2010, and claims priority to GB 1113730.4, filed Aug. 10, 2011, GB 1113729.6, filed Aug. 10, 2011, GB 1113728.8, filed Aug. 10, 2011, and GB 1101937.9, filed Feb. 4, 2011, each of which is hereby incorporated by reference in its entirety.

Inflammation involves the activation of the immune system in response to harmful stimuli, such as, e.g., a pathogen, infection, irritant, or damage to cells. As a stereotyped response, inflammation is a mechanism of innate immunity, as compared to adaptive immunity, which is specific for each pathogen. Inflammation can be classified as either acute or chronic. Generally speaking, acute inflammation is mediated by granulocytes, while chronic inflammation is mediated by mononuclear cells such as monocytes and lymphocytes.

Acute inflammation is an initial protective response of the body to remove an injurious stimulus by maintaining tissue integrity and contributing to tissue repair. It a part of the body's natural defense system against injury and disease, and in the absence of acute inflammation, wounds and infections would never heal and progressive destruction of the tissue would compromise the survival of the organism.

The process of acute inflammation is initiated by cells already present in all tissues, mainly resident macrophages, dendritic cells, histiocytes, Kupffer cells, mastocytes, vascular endothelial cells, and vascular smooth muscle cells. At the onset of a harmful stimulus, these cells undergo activation and release inflammatory mediating and sensitizing molecules, such as, e.g., pro-inflammatory cytokines, pro-inflammatory prostaglandins, leukotrienes, histamine, serotonin, neutral proteases, bradykinin and nitric oxide. These inflammatory molecules modulate a complex series of biological events involving cellular and acellular components of the local vascular system, the immune system, and the injured tissue site to propagate and mature the inflammatory response. These events are responsible for eliciting an acute inflammatory response, typically characterized by 1) vasodilatation which increases blood flow into the tissue thereby causing erythema (redness and warmth), which may extend beyond this site (the flare response); 2) blood vessel permeability which increases plasma leakage into the tissue thereby causing edema (swelling); 3) alter the excitability of certain sensory neurons causing hypersensitivity and pain; 4) stimulate the release of inflammation inducing molecules such as, e.g., neuropeptides like substance P (SP) and calcitonin gene-related peptide (CGRP), prostaglandins, and amino acids like glutamate, from the peripheral nerve endings; and 5) increase migration of leukocytes, mainly granulocytes, from the blood vessels into the tissue. An acute inflammatory response requires constant stimulation to be sustained and must be actively terminated when no longer needed. Hence, acute inflammation ceases once the injurious stimulus has been removed.

However, severe or prolonged noxious stimulation results in a chronic inflammatory response that leads to a progressive shift in the type of cells present at the site of tissue injury. Chronic inflammation may be characterized as the simultaneous destruction and healing of tissue from the inflammatory process, with the net result of provoking injury rather than mediating repair. As such, chronic inflammation is a disease. As an inflammatory response can occur anywhere in the body, chronic inflammation has been implicated in the pathophysiology of a wide range of seemingly unrelated disorders which underlay a large and varied group of human diseases. For example, chronic inflammation is involved in diseases as diverse as cardiovascular diseases, cancers, allergies, obesity, diabetes, digestive system diseases, degenerative diseases, auto-immune disorders, and Alzheimer's disease.

Attempts to treat chronic inflammation have met with limited success. This is due, in part, to the fact that the etiology of chronic inflammation is a complex response based in part on the various inflammation inducing molecules and the multitude of inflammation mediating and sensitizing molecules that appear to elicit inflammation via redundant mechanism. In addition, besides blocking pro-inflammatory molecules, many anti-inflammatory drugs, also inhibit regulatory loops that release endogenous anti-inflammatory molecules. For example, NSAIDs reduce inflammation by blocking the enzymatic activity of cyclooxygenase, a key enzyme that catalyzes the conversion of arachidonic acid to prostaglandins and leukotrienes. Thus, NSAIDs reduce inflammation by preventing the synthesis of all prostaglandins. However, NSAIDs not only prevents the synthesis of proinflammatory prostaglandins, these compounds also prevent the synthesis of anti-inflammatory prostaglandins. Hence, NSAIDs have limited success as they block endogenous anti-inflammatory response, which in some instances may prolong chronic inflammation. Therefore, compounds, compositions, uses, and methods preferentially inhibiting pro-inflammatory responses would be highly desirable for the treatment of chronic inflammation.

The present specification discloses pharmaceutical compositions and methods for treating an individual suffering from a chronic inflammation. The pharmaceutical compositions disclosed herein are essentially a lipid delivery system that enables a therapeutic compound having anti-inflammatory activity to be delivered in a manner that more effectively inhibits a pro-inflammatory response. The end result is an improved treatment for chronic inflammation.

SUMMARY

Aspects of the present specification disclose a pharmaceutical composition comprising a therapeutic compound and a pharmaceutically-acceptable adjuvant. A therapeutic compound may have an anti-inflammatory activity. Other aspects of the present specification disclose a pharmaceutical composition comprising a therapeutic compound disclosed herein, a pharmaceutically-acceptable solvent, and a pharmaceutically-acceptable adjuvant. In other aspects, the pharmaceutical compositions disclosed herein further comprise a pharmaceutically-acceptable stabilizing agent.

Other aspects of the present specification disclose a method of preparing a pharmaceutical composition, the method comprising the step of contacting a therapeutic compound with a pharmaceutically-acceptable adjuvant under conditions which allow the formation of the pharmaceutical composition. Other aspects of the present specification disclose a method of preparing a pharmaceutical composition, the method comprising the steps: a) contacting a pharmaceutically-acceptable solvent with a therapeutic compound under conditions which allow the therapeutic compound to dissolve in the pharmaceutically-acceptable solvent, thereby forming a solution, wherein the therapeutic compound has anti-inflammatory activity, and b) contacting the solution formed in step (a) with a pharmaceutically-acceptable adjuvant under conditions which allow the formation of the pharmaceutical composition. In other aspects, the method of preparing disclosed herein further comprises c) removing the pharmaceutically-acceptable solvent from the pharmaceutical composition.

Other aspects of the present specification disclose a pharmaceutical composition, the pharmaceutical composition made according to a method comprising the step of contacting a therapeutic compound with a pharmaceutically-acceptable adjuvant under conditions which allow the formation of the pharmaceutical composition. Other aspects of the present specification disclose a pharmaceutical composition, the pharmaceutical composition made according to a method comprising the steps: a) contacting a pharmaceutically-acceptable solvent with a therapeutic compound under conditions which allow the therapeutic compound to dissolve in the pharmaceutically-acceptable solvent, thereby forming a solution, wherein the therapeutic compound has anti-inflammatory activity, and b) contacting the solution formed in step (a) with a pharmaceutically-acceptable adjuvant under conditions which allow the formation of the pharmaceutical composition. In other aspects, the method of making a pharmaceutical composition disclosed herein further comprises c) removing the pharmaceutically-acceptable solvent from the pharmaceutical composition.

Other aspects of the present specification disclose a method of treating an individual with a chronic inflammation, the method comprising the step of administering to the individual in need thereof a pharmaceutical composition disclosed herein, wherein administration results in a reduction in a symptom associated with the chronic inflammation, thereby treating the individual.

Other aspects of the present specification disclose a use of a pharmaceutical composition disclosed herein in the manufacture of a medicament for the treatment of a chronic inflammation.

Other aspects of the present specification disclose a use of a pharmaceutical composition disclosed herein for the treatment of a chronic inflammation.

BRIEF DESCRIPTION OF THE DRAWINGS

FIG. 2A shows a graph of the effects of a pharmaceutical composition disclosed herein on in vivo levels of IL-10, whereas FIG. 2B shows a graph of the effects of a pharmaceutical composition disclosed herein on in vivo levels of IL-4. BC1054 ORAL=Group A; Vehicle ORAL=Group B; and BC1054 Lipid ORAL=Group C.

FIG. 3A shows a graph of the effects of a pharmaceutical composition disclosed herein on in vivo levels of IL-10; FIG. 3B shows a graph of the effects of a pharmaceutical composition disclosed herein on in vivo levels of TNF-α; and FIG. 3C shows a graph of the effects of a pharmaceutical composition disclosed herein on in vivo levels of IFN-γ. BC1054 ORAL=Group A; Vehicle ORAL=Group B; and BC1054 Lipid ORAL=Group C.

DESCRIPTION

Figure 1:
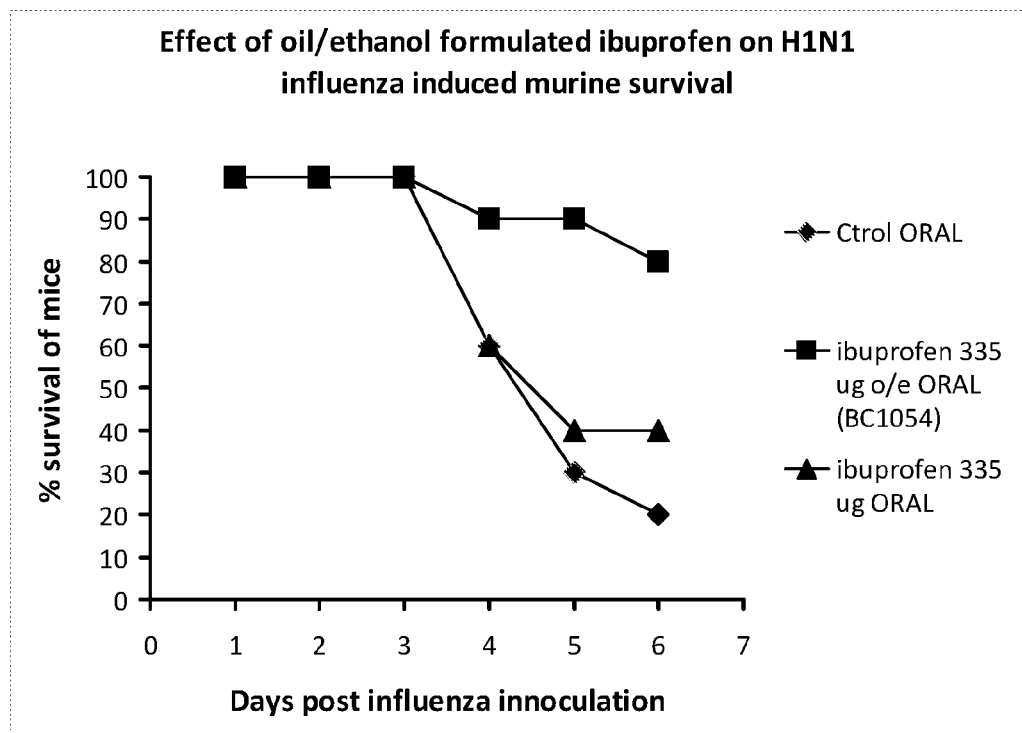
FIG. 1 shows the effects of a pharmaceutical composition disclosed herein on survival against Influenza A/PR/8/34 lethal challenge. Ibuprofen 335 μg=Group A; Ctrol ORAL=Group B; and ibuprofen 335 μg o/e ORAL (BC1054)=Group C.

Aspects of the present specification disclose, in part, a pharmaceutical composition. As used herein, the term "pharmaceutically acceptable" means any molecular entity or composition that does not produce an adverse, allergic or other untoward or unwanted reaction when administered to an individual. As used herein, the term "pharmaceutically acceptable composition" is synonymous with "pharmaceutical composition" and means a therapeutically effective concentration of an active ingredient, such as, e.g., any of the therapeutic compounds disclosed herein. A pharmaceutical composition disclosed herein is useful for medical and veterinary applications. A pharmaceutical composition may be administered to an individual alone, or in combination with other supplementary active ingredients, agents, drugs or hormones.

A pharmaceutical composition disclosed herein may optionally include a pharmaceutically-acceptable carrier that facilitates processing of an active ingredient into pharmaceutically-acceptable compositions. As used herein, the term "pharmacologically-acceptable carrier" is synonymous with "pharmacological carrier" and means any carrier that has substantially no long term or permanent detrimental effect when administered and encompasses terms such as "pharmacologically acceptable vehicle, stabilizer, diluent, additive, auxiliary or excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

In one embodiment, a pharmaceutical composition disclosed herein comprises a therapeutic compound having anti-inflammatory activity and a pharmaceutically-acceptable adjuvant. In another embodiment, a pharmaceutical composition disclosed herein comprises a therapeutic compound having anti-inflammatory activity, a pharmaceutically-acceptable solvent, and a pharmaceutically-acceptable adjuvant. In aspects of this embodiment, a pharmaceutical composition disclosed herein may further comprise a pharmaceutically-acceptable stabilizing agent. In other aspects of this embodiment, a pharmaceutical composition disclosed herein may further comprise a pharmaceutically-acceptable carrier, a pharmaceutically-acceptable component, or both pharmaceutically-acceptable carrier and pharmaceutically-acceptable component.

Aspects of the present specification disclose, in part, a therapeutic compound. A therapeutic compound is a compound that provides pharmacological activity or other direct effect in the diagnosis, cure, mitigation, treatment, or prevention of disease, or to affect the structure or any function of the body of man or animals. A therapeutic compound disclosed herein may be used in the form of a pharmaceutically acceptable salt, solvate, or solvate of a salt, e.g. the hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. A therapeutic compound disclosed herein may have anti-inflammatory activity.

In an embodiment, a therapeutic compound disclosed herein has an anti-inflammatory activity capable of reducing the levels of an inflammation inducing molecule. In an aspect of this embodiment, a therapeutic compound disclosed herein has an anti-inflammatory activity capable of reducing the levels of substance P (SP), calcitonin gene-related peptide (CGRP), glutamate, or a combination thereof. In other aspects of this embodiment, a therapeutic compound disclosed herein has an anti-inflammatory activity capable of reducing the levels of SP, CGRP, glutamate, or a combination thereof released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein has an anti-inflammatory activity capable of reducing the levels of SP, CGRP, glutamate, or a combination thereof released from a sensory neuron in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Prostaglandins mediate a local inflammatory response and are involved in all inflammatory functions through action on prostaglandin receptors and mediate inflammatory signaling including chemotaxis (macrophages, neutrophils and eosinophils), vasodilation and algesia. However, the PG-mediated inflammatory response is self-limiting (resolving). The principle resolution factor is a prostaglandin called 15dPGJ2, which is an endogenous agonist of peroxisome proliferator-activator receptor gamma (PPAR-γ) signaling. PPARγ signaling pathway 1) induces apoptosis of Macrophage M1 cells, thereby reducing the levels of Th1 pro-inflammatory cytokines and 2) promotes differentiation of monocytes into Macrophage M2 cells. Macrophage M2 cells produce and release Th2 anti-inflammatory cytokines.

In an embodiment, a therapeutic compound disclosed herein has an anti-inflammatory activity capable of reducing the levels of an inflammation inducing prostaglandin. In other aspects of this embodiment, a therapeutic compound disclosed herein has an anti-inflammatory activity capable of reducing the levels of a inflammation inducing prostaglandin released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein has an anti-inflammatory activity capable of reducing the levels of a inflammation inducing prostaglandin released from a sensory neuron in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein has an anti-inflammatory activity substantially similar to 15dPGJ2. In aspects of this embodiment, a therapeutic compound disclosed herein an anti-inflammatory activity that is, e.g., at least 5%, at least 15%, at least 25%, at least 50%, at least 55%, at least 60%, at least 65%, at least 70%, at least 75%, at least 80%, at least 85%, at least 90% or at least 95% of the activity observed for 15dPGJ2. In other aspects of this embodiment, a therapeutic compound disclosed herein an anti-inflammatory activity that is in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50% of the activity observed for 15dPGJ2.

The peroxisome proliferator-activated receptors (PPARs) are a group of nuclear receptor proteins that function as transcription factors regulating the expression of genes. All PPARs are known to heterodimerize with the retinoid X receptor (RXR) and bind to specific regions on the DNA of target genes called peroxisome proliferator hormone response elements (PPREs). PPARs play essential roles in the regulation of cellular differentiation, development, and metabolism (carbohydrate, lipid, protein), and tumorigenesis of higher organisms. The family comprises three members, PPAR-α, PPAR-γ, and PPAR-δ (also known as PPAR-β). PPAR-α is expressed in liver, kidney, heart, muscle, adipose tissue, as well as other tissues. PPAR-δ is expressed in many tissues but markedly in brain, adipose tissue, and skin. PPAR-γ comprises three alternatively-spliced forms, each with a different expression pattern. PPAR-γ1 is expressed in virtually all tissues, including heart, muscle, colon, kidney, pancreas, and spleen. PPAR-γ2 is expressed mainly in adipose tissue. PPAR-γ3 is expressed in macrophages, large intestine, and white adipose tissue. Endogenous ligands for the PPARs include free fatty acids and eicosanoids. PPAR-γ is activated by PGJ2 (a prostaglandin), whereas PPAR-α is activated by leukotriene B4.

In an embodiment, a therapeutic compound disclosed herein has an anti-inflammatory activity capable of stimulating all PPAR signaling pathways. Such a therapeutic compound includes a PPAR pan-agonist. In other embodiments, a therapeutic compound disclosed herein has an anti-inflammatory activity capable of stimulating one or two of the PPAR signaling pathways. Such a therapeutic compound includes a selective PPAR agonist.

In another embodiment, a therapeutic compound disclosed herein has an anti-inflammatory activity capable of stimulating a PPAR-α signaling pathway. In aspects of this embodiment, a therapeutic compound disclosed herein stimulates a PPAR-α signaling pathway by, e.g., at least 5%, at least 15%, at least 25%, at least 50%, at least 60%, at least 70%, at least 80%, or at least 90%. In other aspects of this embodiment, a therapeutic compound disclosed herein stimulates a PPAR-α signaling pathway in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

In another embodiment, a therapeutic compound disclosed herein has an anti-inflammatory activity capable of stimulating a PPAR-δ signaling pathway. In aspects of this embodiment, a therapeutic compound disclosed herein stimulates a PPAR-δ signaling pathway by, e.g., at least 5%, at least 15%, at least 25%, at least 50%, at least 60%, at least 70%, at least 80%, or at least 90%. In other aspects of this embodiment, a therapeutic compound disclosed herein stimulates a PPAR-δ signaling pathway in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

In another embodiment, a therapeutic compound disclosed herein has an anti-inflammatory activity capable of stimulating a PPARγ signaling pathway. A therapeutic compounds disclosed herein may be capable of binding to all isoforms of PPAR-γ, or may be capable of selectively binding to either PPAR-γ1, PPAR-γ2, PPAR-γ3, or any combination of two thereof. In aspects of this embodiment, a therapeutic compound disclosed herein stimulates a PPARγ signaling pathway by, e.g., at least 5%, at least 15%, at least 25%, at least 50%, at least 60%, at least 70%, at least 80%, or at least 90%. In other aspects of this embodiment, a therapeutic compound disclosed herein stimulates a PPARγ signaling pathway in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

Macrophages are activated and polarized into distinct phenotypes expressing unique cell surface molecules and secreting discrete sets of cytokines and chemokines. The classical M1 phenotype supports pro-inflammatory Th1 responses driven by cytokines such as, e.g., Interleukin-6 (IL-6), IL-12 and IL-23, while the alternate M2 phenotype is generally supportive of anti-inflammatory processes driven by IL-10. M2 cells can be further classified into subsets, M2a, M2b, and M2c, based on the type of stimulation and the subsequent expression of surface molecules and cytokines.

In yet another embodiment, a therapeutic compound disclosed herein has an anti-inflammatory activity capable of promoting the resolving phenotypic change of M1 to M2. In an aspect of this embodiment, a therapeutic compound disclosed herein has an anti-inflammatory activity capable of inducing apoptosis of Macrophage M1 cells. In another aspect of this embodiment, a therapeutic compound disclosed herein has an anti-inflammatory activity capable of promoting differentiation of Macrophage M2 cells. In yet another aspect of this embodiment, a therapeutic compound disclosed herein has an anti-inflammatory activity capable of inducing apoptosis of Macrophage M1 cells and promoting differentiation of Macrophage M2 cells.

In still another embodiment, a therapeutic compound disclosed herein has an anti-inflammatory activity capable of modulating Th1 and Th2 cytokines. In an aspect of this embodiment, a therapeutic compound disclosed herein has an anti-inflammatory activity capable of reducing the levels of Interferon-gamma (IFNγ), Tumor necrosis factor-alpha (TNF-α), Interleukin-12 (IL-12), or a combination thereof released from a Th1 cell. In other aspects of this embodiment, a therapeutic compound disclosed herein has an anti-inflammatory activity capable of reducing the levels of IFNγ, TNF-α, IL-12, or a combination thereof released from a Th1 cell by, e.g., at least 10%, at least 20%, at least 30%, at least 40%, at least 50%, at least 60%, at least 70%, at least 80%, or at least 90%. In yet other aspects of this embodiment, a therapeutic compound disclosed herein has an anti-inflammatory activity capable of reducing the levels of IFNγ, TNF-α, IL-12, or a combination thereof released from a Th1 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another aspect of this embodiment, a therapeutic compound disclosed herein has an anti-inflammatory activity capable of increasing the levels of IL-10 released from a Th2 cell. In other aspects of this embodiment, a therapeutic compound disclosed herein has an anti-inflammatory activity capable of increasing the levels of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein has an anti-inflammatory activity capable of increasing the levels of IL-10 released from a Th2 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another aspect of this embodiment, a therapeutic compound disclosed herein has an anti-inflammatory activity capable of reducing the levels of IFNγ, TNF-α, IL-12, or a combination thereof released from a Th1 cell and increasing the levels of IL-10 released from a Th2 cell. In other aspects of this embodiment, a therapeutic compound disclosed herein has an anti-inflammatory activity capable of reducing the levels of IFNγ, TNF-α, IL-12, or a combination thereof released from a Th1 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%, and capable of increasing the levels of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein has an anti-inflammatory activity capable of reducing the levels of IFNγ, TNF-α, IL-12, or a combination thereof released from a Th1 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%, and capable of increasing the levels of IL-10 released from a Th2 cell in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A therapeutic compound disclosed herein may have a log P value indicating that the compound is soluble in an organic solvent. As used herein, the term "log P value" refers to the logarithm (base 10) of the partition coefficient (P) for a compound and is a measure of lipophilicity. Typically, P is defined as the ratio of concentrations of a unionized compound in the two phases of a mixture of two immiscible solvents at equilibrium. Thus, log P=Log 10 (P), where P=[solute in immiscible solvent 1]/[solute in immiscible solvent 2]. With regard to organic and aqueous phases, the log P value of a compound is constant for any given pair of aqueous and organic solvents, and its value can be determined empirically by one of several phase-partitioning methods known to one skilled in the art including, e.g., a shake flask assay, a HPLC assay, and an interface between two immiscible electrolyte solutions (ITIES) assay.

In aspects of this embodiment, a therapeutic compound disclosed herein may have a log P value indicating that the compound is substantially soluble in an organic solvent. In aspects of this embodiment, a therapeutic compound disclosed herein may have a log P value indicating that the compound is, e.g., at least 50% soluble in an organic solvent, at least 60% soluble in an organic solvent, at least 70% soluble in an organic solvent, at least 80% soluble in an organic solvent, or at least 90% soluble in an organic solvent. In aspects of this embodiment, a therapeutic compound disclosed herein may have a log P value indicating that the compound is between, e.g., about 50% to about 100% soluble in an organic solvent, about 60% to about 100% soluble in an organic solvent, about 70% to about 100% soluble in an organic solvent, about 80% to about 100% soluble in an organic solvent, or about 90% to about 100% soluble in an organic solvent.

In aspects of this embodiment, a therapeutic compound disclosed herein may have a log P value of, e.g., more than 1.1, more than 1.2, more than 1.4, more than 1.6, more than 1.8, more than 2.0, more than 2.2, more than 2.4, more than 2.6, more than 2.8, more than 3.0, more than 3.2, more than 3.4, or more than 3.6. In other aspects of this embodiment, a therapeutic compound disclosed herein may have a log P value in the range of, e.g., between 1.8 and 4.0, between 2.0 and 4.0, between 2.1 and 4.0, between 2.2 and 4.0, or between 2.3 and 4.0, between 2.4 and 4.0, between 2.5 and 4.0, between 2.6 and 4.0, or between 2.8 and 4.0. In other aspects of this embodiment, a therapeutic compound disclosed herein may have a log P value in the range of, e.g., between 3.0 and 4.0, or between 3.1 and 4.0, between 3.2 and 4.0, between 3.3 and 4.0, between 3.4 and 4.0, between 3.5 and 4.0, or between 3.6 and 4.0. In still other aspects of this embodiment, a therapeutic compound disclosed herein may have a log P value in the range of, e.g., between 2.0 and 2.5, between 2.0 and 2.7, between 2.0 and 3.0, or between 2.2 and 2.5.

A therapeutic compound disclosed herein may have a polar surface area that is hydrophobic. As used herein, the term "polar surface area" refers to the surface sum over all of the polar atoms in the structure of a compound and is a measure of hydrophobicity. Typically, these polar atoms include, e.g., oxygen, nitrogen, and their attached hydrogens. In aspects of this embodiment, a therapeutic compound disclosed herein may have a polar surface area of, e.g., less than 8.0 nm$^2$, less than 7.0 nm$^2$, less than 6.0 nm$^2$, less than 5.0 nm$^2$, less than 4.0 nm$^2$, or less than 3.0 nm$^2$. In other aspects of this embodiment, a therapeutic compound disclosed herein may have a polar surface area in the range of, e.g., between 3.0 nm$^2$ and 6.5 nm$^2$, between 3.0 nm$^2$ and 6.0 nm$^2$, between 3.0 nm$^2$ and 5.5 nm$^2$, between 3.0 nm$^2$ and 5.0 nm$^2$, between 3.0 nm$^2$ and 4.5 nm$^2$, between 3.5 nm$^2$ and 6.5 nm$^2$, between 3.5 nm$^2$ and 6.0 nm$^2$, between 3.5 nm$^2$ and 5.5 nm$^2$, between 3.5 nm$^2$ and 5.0 nm$^2$, between 3.5 nm$^2$ and 4.5 nm$^2$, between 4.0 nm$^2$ and 6.5 nm$^2$, between 4.0 nm$^2$ and 6.0 nm$^2$, between 4.0 nm$^2$ and 5.5 nm$^2$, or between 4.0 nm$^2$ and 5.0 nm$^2$, between 4.0 nm$^2$ and 4.5 nm$^2$, or between 4.5 nm$^2$ and 5.5 nm$^2$. In yet other aspects of this embodiment, a therapeutic compound disclosed herein may have a polar surface area in the range of, e.g., between 2.0 nm$^2$ and 6.5 nm$^2$, between 2.0 nm$^2$ and 6.0 nm$^2$, between 2.0 nm$^2$ and 5.5 nm$^2$, between 2.0 nm$^2$ and 5.0 nm$^2$, between 2.0 nm$^2$ and 4.5 nm$^2$, between 2.5 nm$^2$ and 6.5 nm$^2$, between 2.5 nm$^2$ and 6.0 nm$^2$, between 2.5 nm$^2$ and 5.5 nm$^2$, between 2.5 nm$^2$ and 5.0 nm$^2$, or between 2.5 nm$^2$ and 4.5 nm$^2$.

A therapeutic compound disclosed herein may be a non-steroidal anti-inflammatory drug (NSAID). NSAIDs are a large group of therapeutic compounds with analgesic, anti-inflammatory, and anti-pyretic properties. NSAIDs reduce inflammation by blocking cyclooxygenase. NSAIDs include, without limitation, Aceclofenac, Acemetacin, Act-arit, Alcofenac, Alminoprofen, Amfenac, Aloxipirin, Aminophenazone, Antraphenine, Aspirin, Azapropazone, Benorilate, Benoxaprofen, Benzydamine, Butibufen, Cele-coxib, Chlorthenoxacin, Choline Salicylate, Clometacin, Dexketoprofen, Diclofenac, Diflunisal, Emorfazone, Epirizole; Etodolac, Etoricoxib, Feclobuzone, Felbinac, Fenbufen, Fenclofenac, Flurbiprofen, Glafenine, Hydroxyethyl salicylate, Ibuprofen, Indometacin, Indoprofen, Ketoprofen, Ketorolac, Lactyl phenetidin, Loxoprofen, Lumiracoxib, Mefenamic acid, Meloxicam, Metamizole, Metiazinic acid, Mofebutazone, Mofezolac, Nabumetone, Naproxen, Nifenazone, Niflumic acid, Oxametacin, Phenacetin, Pipebuzone, Pranoprofen, Propyphenazone, Proquazone, Protizinic acid, Rofecoxib, Salicylamide, Salsalate, Sulindac, Suprofen, Tiaramide, Tinoridine, Tolfenamic acid, Valdecoxib, and Zomepirac.

NSAIDs may be classified based on their chemical structure or mechanism of action. Non-limiting examples of NSAIDs include a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, and a selective cyclooxygenase 2 (COX 2) inhibitor. A NSAID may be a profen. Examples of a suitable salicylate derivative NSAID include, without limitation, Acetylsalicylic acid (asprin), Diflunisal, and Salsalate. Examples of a suitable p-amino phenol derivative NSAID include, without limitation, Paracetamol and Phenacetin. Examples of a suitable propionic acid derivative NSAID include, without limitation, Alminoprofen, Benoxaprofen, Dexketoprofen, Fenoprofen, Flurbiprofen, Ibuprofen, Indoprofen, Ketoprofen, Loxoprofen, Naproxen, Oxaprozin, Pranoprofen, and Suprofen. Examples of a suitable acetic acid derivative NSAID include, without limitation, Aceclofenac, Acemetacin, Act-arit, Alcofenac, Amfenac, Clometacin, Diclofenac, Etodolac, Felbinac, Fenclofenac, Indometacin, Ketorolac, Metiazinic acid, Mofezolac, Nabumetone, Naproxen, Oxametacin, Sulindac, and Zomepirac. Examples of a suitable enolic acid (Oxicam) derivative NSAID include, without limitation, Droxicam, Isoxicam, Lornoxicam, Meloxicam, Piroxicam, and Tenoxicam. Examples of a suitable fenamic acid derivative NSAID include, without limitation, Flufenamic acid, Mefenamic acid, Meclofenamic acid, and Tolfenamic acid. Examples of a suitable selective COX-2 inhibitors include, without limitation, Celecoxib, Etoricoxib, Firocoxib, Lumiracoxib, Meloxicam, Parecoxib, Rofecoxib, and Valdecoxib.

A therapeutic compound disclosed herein may be a PPARγ agonist. Examples of a suitable PPARγ agonist include, without limitation, Benzbromarone, a cannabidiol, Cilostazol, Curcumin, Delta(9)-tetrahydrocannabinol, glycyrrhetinic acid, Indomethacin, Irbesartan, Monascin, mycophenolic acid, Resveratrol, 6-shogaol, Telmisartan, a thiazolidinedione like Rosiglitazone, Pioglitazone, and Troglitazone, a NSAID, and a fibrate. Other suitable PPARγ agonists are described in Masson and Caumont-Bertrand, PPAR Agonist Compounds, Preparation and Uses, US 2011/0195993, which is hereby incorporated by reference in its entirety.

A therapeutic compound disclosed herein may be a nuclear receptor binding agent. Examples of a suitable nuclear receptor binding agent include, without limitation, a Retinoic Acid Receptor (RAR) binding agent, a Retinoid X Receptor (RXR) binding agent, a Liver X Receptor (LXR) binding agent and a Vitamin D binding agent.

A therapeutic compound disclosed herein may be an anti-hyperlipidemic agent. There are several classes of anti-hyperlipidemic agents (also known as hypolipidemic agents). They may differ in both their impact on the cholesterol profile and adverse effects. For example, some may lower low density lipoprotein (LDL), while others may preferentially increase high density lipoprotein (HDL). Clinically, the choice of an agent will depend on the cholesterol profile of an individual, cardiovascular risk of an individual, and/or the liver and kidney functions of an individual. Examples of a suitable anti-hyperlipidemic agent include, without limitation, a fibrate, a statin, a tocotrienol, a niacin, a bile acid sequestrants (resin), a cholesterol absorption inhibitor, a pancreatic lipase inhibitor, and a sympathomimetic amine.

A therapeutic compound disclosed herein may be a fibrate. Fibrates are a class of amphipathic carboxylic acids with lipid level modifying properties. These therapeutic compounds are used for a range of metabolic disorders. One non-limiting use is as an anti-hyperlipidemic agent where it may lower levels of, e.g., triglycerides and LDL as well as increase levels of HDL. Examples of a suitable fibrate include, without limitation, Bezafibrate, Ciprofibrate, Clofibrate, Gemfibrozil, and Fenofibrate.

A therapeutic compound disclosed herein may be a statin. Statins (or HMG-CoA reductase inhibitors) are a class of therapeutic compounds used to lower LDL and/or cholesterol levels by inhibiting the enzyme HMG-CoA reductase, which plays a central role in the production of cholesterol in the liver. To compensate for the decreased cholesterol availability, synthesis of hepatic LDL receptors is increased, resulting in an increased clearance of LDL particles from the blood. Examples of a suitable statin include, without limitation, Atorvastatin, Fluvastatin, Lovastatin, Pitavastatin, Pravastatin, Rosuvastatin, and Simvastatin.

A therapeutic compound disclosed herein may be a tocotrienol. Tocotrienols are anotehr class of HMG-CoA reductase inhibitors and may be used to lower LDL and/or cholesterol levels by inducing hepatic LDL receptor up-regulation and/or decreasing plasma LDL levels. Examples of a suitable tocotrienol include, without limitation, a γ-tocotrienol and a δ-tocotrienol.

A therapeutic compound disclosed herein may be a niacin. Niacins are a class of therapeutic compounds with lipid level modifying properties. For example, a niacin may lower LDL by selectively inhibiting hepatic diacyglycerol acyltransferase 2, reduce triglyceride synthesis, and VLDL secretion through a receptor HM74 and HM74A or GPR109A. These therapeutic compounds are used for a range of metabolic disorders. One non-limiting use is as an anti-hyperlipidemic agent where it may inhibit the breakdown of fats in adipose tissue. Because a niacin blocks the breakdown of fats, it causes a decrease in free fatty acids in the blood and, as a consequence, decreases the secretion of very-low-density lipoproteins (VLDL) and cholesterol by the liver. By lowering VLDL levels, a niacin may also increase the level of HDL in blood. Examples of a suitable niacin include, without limitation, acipimox, niacin, nicotinamide, and vitamin B3.

A therapeutic compound disclosed herein may be a bile acid sequestrant. Bile acid sequestrants (also known as resins) are a class of therapeutic compounds used to bind certain components of bile in the gastrointestinal tract. They disrupt the enterohepatic circulation of bile acids by sequestering them and preventing their reabsorption from the gut. Bile acid sequestrants are particularly effective for lowering LDL and cholesterol by sequestering the cholesterol-containing bile acids released into the intestine and preventing their reabsorption from the intestine. In addition, a bile acid sequestrant may also raise HDL levels. Examples of a suitable bile acid sequestrant include, without limitation, Cholestyramine, Colesevelam, and Colestipol.

A therapeutic compound disclosed herein may be a cholesterol absorption inhibitor. Cholesterol absorption inhibitors are a class of therapeutic compounds that inhibits the absorption of cholesterol from the intestine. Decreased cholesterol absorption leads to an upregulation of LDL-receptors on the surface of cells and an increased LDL-cholesterol uptake into these cells, thus decreasing levels of LDL in the blood plasma. Examples of a suitable cholesterol absorption inhibitor include, without limitation, Ezetimibe, a phytosterol, a sterol and a stanol.

A therapeutic compound disclosed herein may be a fat absorption inhibitor. Fat absorption inhibitors are a class of therapeutic compounds that inhibits the absorption of fat from the intestine. Decreased fat absorption reduces caloric intake. In one aspect, a fat absorption inhibitor inhibits pancreatic lipase, an enzyme that breaks down triglycerides in the intestine. Examples of a suitable fat absorption inhibitor include, without limitation, Orlistat.

A therapeutic compound disclosed herein may be a sympathomimetic amine. Sympathomimetic amines are a class of therapeutic compounds that mimic the effects of transmitter substances of the sympathetic nervous system such as catecholamines, epinephrine (adrenaline), norepinephrine (noradrenaline), and/or dopamine. A sympathomimetic amine may act as an α-adrenergic agonist, a β-adrenergic agonist, a dopaminergic agonist, a monoamine oxidase (MAO) inhibitor, and a COMT inhibitor. Such therapeutic compounds, among other things, are used to treat cardiac arrest, low blood pressure, or even delay premature labor. Examples of a suitable sympathomimetic amine include, without limitation, Clenbuterol, Salbutamol, ephedrine, pseudoephedrine, methamphetamine, amphetamine, phenylephrine, isoproterenol, dobutamine, methylphenidate, lisdexamfetamine, cathine, cathinone, methcathinone, cocaine, benzylpiperazine (BZP), methylenedioxypyrovalerone (MDPV), 4-methylaminorex, pemoline, phenmetrazine, and propylhexedrine.

A therapeutic compound disclosed herein may be an ester of a therapeutic compound. An ester of a therapeutic compound increases the log P value relative to the same therapeutic compound, but without the ester modification. An ester group may be attached to a therapeutic compound by, e.g., a carboxylic acid or hydroxyl functional group present of the therapeutic compound. An ester of a therapeutic compound may have an increased hydrophobicity, and as such, may be dissolved in a reduced volume of solvent disclosed herein. In some instances, an ester of a therapeutic compound may be combined directly with an adjuvant disclosed herein, thereby eliminating the need of a solvent. An ester of a therapeutic compound may enable the making of a pharmaceutical composition disclosed herein, in situations where a non-esterified form of the same therapeutic compound is otherwise immiscible in a solvent disclosed herein. An ester of a therapeutic compound may still be delivered in a manner that more effectively inhibits a pro-inflammatory response as long as the compound is combined with an adjuvant disclosed herein. In one embodiment, a therapeutic compound may be reacted with ethyl ester in order to form an ethyl ester of the therapeutic compound.

In another embodiment, a pharmaceutical composition disclosed herein does not comprise a pharmaceutically-acceptable solvent disclosed herein. In an aspect of this embodiment, a pharmaceutical composition comprises a therapeutic compound and a pharmaceutically-acceptable adjuvant, but does not comprise a pharmaceutically-acceptable solvent disclosed herein.

A pharmaceutical composition disclosed herein may comprise a therapeutic compound in an amount sufficient to allow customary administration to an individual. In aspects of this embodiment, a pharmaceutical composition disclosed herein may be, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In other aspects of this embodiment, a pharmaceutical composition disclosed herein may be, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a pharmaceutical composition disclosed herein may be in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still other aspects of this embodiment, a pharmaceutical composition disclosed herein may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

Aspects of the present specification disclose, in part, a pharmaceutically-acceptable solvent. A solvent is a liquid, solid, or gas that dissolves another solid, liquid, or gaseous (the solute), resulting in a solution. Solvents useful in the pharmaceutical compositions disclosed herein include, without limitation, a pharmaceutically-acceptable polar aprotic solvent, a pharmaceutically-acceptable polar protic solvent and a pharmaceutically-acceptable non-polar solvent. A pharmaceutically-acceptable polar aprotic solvent includes, without limitation, dichloromethane (DCM), tetrahydrofuran (THF), ethyl acetate, acetone, dimethylformamide (DMF), acetonitrile (MeCN), dimethyl sulfoxide (DMSO). A pharmaceutically-acceptable polar protic solvent includes, without limitation, acetic acid, formic acid, ethanol, n-butanol, 1-butanol, 2-butanol, isobutanol, sec-butanol, tert-butanol, n-propanol, isopropanol, 1,2 propan-diol, methanol, glycerol, and water. A pharmaceutically-acceptable non-polar solvent includes, without limitation, pentane, cyclopentane, hexane, cyclohexane, benzene, toluene, 1,4-Dioxane, chloroform, n-methyl-pyrrilidone (NMP), and diethyl ether.

A pharmaceutical composition disclosed herein may comprise a solvent in an amount sufficient to dissolve a therapeutic compound disclosed herein. In other aspects of this embodiment, a pharmaceutical composition disclosed herein may comprise a solvent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, a pharmaceutical composition disclosed herein may comprise a solvent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

In one embodiment, a solvent may comprise a pharmaceutically-acceptable alcohol. As used herein, the term "alcohol" refers to an organic molecule comprising a hydroxyl functional group (—OH) bond to a carbon atom, where the carbon atom is saturated. In aspects of this embodiment, the alcohol may be, e.g., a $C_{2-4}$ alcohol, a $C_{1-4}$ alcohol, a $C_{1-5}$ alcohol, a $C_{1-7}$ alcohol, a $C_{1-10}$ alcohol, a $C_{1-15}$ alcohol, or a $C_{1-20}$ alcohol. In other aspects of this embodiment, an alcohol may be, e.g., a primary alcohol, a secondary alcohol, or a tertiary alcohol. In other aspects of this embodiment, an alcohol may be, e.g., an acyclic alcohol, a monohydric alcohol, a polyhydric alcohol (also known as a polyol or sugar alcohol), an unsaturated aliphatic alcohol, an alicyclic alcohol, or a combination thereof. Examples of a monohydric alcohol include, without limitation, methanol, ethanol, propanol, butanol, pentanol, and 1-hexadecanol. Examples of a polyhydric alcohol include, without limitation, glycol, glycerol, arabitol, erythritol, xylitol, maltitol, sorbitol (gluctiol), mannitol, inositol, lactitol, galactitol (iditol), and isomalt. Examples of an unsaturated aliphatic alcohol include, without limitation, prop-2-ene-1-ol, 3,7-dimethylocta-2,6-dien-1-ol, and prop-2-in-1-ol. Examples of an alicyclic alcohol include, without limitation, cyclohexane-1,2,3,4,5,6-hexol and 2-(2-propyl)-5-methyl-cyclohexane-1-ol.

In another embodiment, a solvent may comprise an ester of pharmaceutically-acceptable alcohol and an acid. Suitable pharmaceutically-acceptable alcohols include the ones disclosed herein. Suitable acids include, without limitation, acetic acid, butaric acid, and formic acid. An ester of an alcohol and an acid include, without limitation, methyl acetate, methyl buterate, methyl formate, ethyl acetate, ethyl buterate, ethyl formate, propyl acetate, propyl buterate, propyl formate, butyl acetate, butyl buterate, butyl formate, isobutyl acetate, isobutyl buterate, isobutyl formate, pentyl acetate, pentyl buterate, pentyl formate, and 1-hexadecyl acetate, 1-hexadecyl buterate, and 1-hexadecyl formate.

In another embodiment, a solvent may comprise a pharmaceutically-acceptable polyethylene glycol (PEG) polymer. PEG polymers, also known as polyethylene oxide (PEO) polymers or polyoxyethylene (POE) polymers, are prepared by polymerization of ethylene oxide and are commercially available over a wide range of molecular weights from 100 g/mol to 10,000,000 g/mol. PEG polymers with a low molecular mass are liquids or low-melting solids, whereas PEG polymers of a higher molecular mass are solids. A PEG polymer include, without limitation, PEG 100, PEG 200, PEG 300, PEG 400, PEG 500, PEG 600, PEG 700, PEG 800, PEG 900, PEG 1000, PEG 1100, PEG 1200, PEG 1300, PEG 1400, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750, PEG 5000, PEG 5500, PEG 6000, PEG 6500, PEG 7000, PEG 7500, PEG 8000, PEG 8500, PEG 9000, PEG 9500, PEG 10,000, PEG 11,000, PEG 12,000, PEG 13,000, PEG 14,000, PEG 15,000, PEG 16,000, PEG 17,000, PEG 18,000, PEG 19,000, or PEG 20,000.

In another embodiment, a solvent may comprise a pharmaceutically-acceptable glyceride.

Glycerides comprise a substituted glycerol, where one, two, or all three hydroxyl groups of the glycerol are each esterified using a fatty acid to produce monoglycerides, diglycerides, and triglycerides, respectively. In these compounds, each hydroxyl groups of glycerol may be esterified by different fatty acids. Additionally, glycerides may be acetylated to produce acetylated monoglycerides, acetylated diglycerides, and acetylated triglycerides.

In one embodiment, a solvent may comprise a pharmaceutically-acceptable solid solvent. Solid solvents may be useful in the manufacture of a solid dose formulation of a pharmaceutical composition disclosed herein. Typically, a solid solvent is melted in order to dissolve a therapeutic compound. A pharmaceutically-acceptable solid solvent includes, without limitation, Menthol and PEG polymers above about 20,000 g/mol.

Aspects of the present specification disclose, in part, a pharmaceutically-acceptable adjuvant. An adjuvant is a pharmacological agent that modifies the effect of other agents, such as, e.g., a therapeutic compound disclosed herein. In addition, an adjuvant disclosed herein may be used as a solvent that dissolves a therapeutic compound disclosed herein, forming a adjuvant solution. An adjuvant disclosed herein facilitates delivery of a therapeutic compound in a manner that more effectively inhibits a pro-inflammatory response. In one embodiment, an adjuvant disclosed herein facilitates the delivery of a therapeutic compound disclosed herein into macrophages.

A pharmaceutical composition disclosed herein may comprise a pharmaceutically-acceptable adjuvant in an amount sufficient to mix with a solution disclosed herein or an emulsion disclosed herein. In other aspects of this embodiment, a pharmaceutical composition disclosed herein may comprise an adjuvant in an amount of, e.g., at least 10% (v/v), at least 20% (v/v), at least 30% (v/v), at least 35% (v/v), at least 40% (v/v), at least 45% (v/v), at least 50% (v/v), at least 55% (v/v), at least 60% (v/v), at least 65% (v/v), at least 70% (v/v), at least 75% (v/v), at least 80% (v/v), at least 85% (v/v), at least 90% (v/v), at least 95% (v/v), or at least 99% (v/v). In other aspects of this embodiment, a pharmaceutical composition disclosed herein may comprise an adjuvant in an amount in a range of, e.g., about 30% (v/v) to about 99% (v/v), about 35% (v/v) to about 99% (v/v), about 40% (v/v) to about 99% (v/v), about 45% (v/v) to about 99% (v/v), about 50% (v/v) to about 99% (v/v), about 30% (v/v) to about 98% (v/v), about 35% (v/v) to about 98% (v/v), about 40% (v/v) to about 98% (v/v), about 45% (v/v) to about 98% (v/v), about 50% (v/v) to about 98% (v/v), about 30% (v/v) to about 95% (v/v), about 35% (v/v) to about 95% (v/v), about 40% (v/v) to about 95% (v/v), about 45% (v/v) to about 95% (v/v), or about 50% (v/v) to about 95% (v/v). In yet other aspects of this embodiment, a pharmaceutical composition disclosed herein may comprise an adjuvant in an amount in a range of, e.g., about 70% (v/v) to about 97% (v/v), about 75% (v/v) to about 97% (v/v), about 80% (v/v) to about 97% (v/v), about 85% (v/v) to about 97% (v/v), about 88% (v/v) to about 97% (v/v), about 89% (v/v) to about 97% (v/v), about 90% (v/v) to about 97% (v/v), about 75% (v/v) to about 96% (v/v), about 80% (v/v) to about 96% (v/v), about 85% (v/v) to about 96% (v/v), about 88% (v/v) to about 96% (v/v), about 89% (v/v) to about 96% (v/v), about 90% (v/v) to about 96% (v/v), about 75% (v/v) to about 93% (v/v), about 80% (v/v) to about 93% (v/v), about 85% (v/v) to about 93% (v/v), about 88% (v/v) to about 93% (v/v), about 89% (v/v) to about 93% (v/v), or about 90% (v/v) to about 93% (v/v).

In one embodiment, an adjuvant may be a pharmaceutically-acceptable lipid. A lipid may be broadly defined as a hydrophobic or amphiphilic small molecule. The amphiphilic nature of some lipids allows them to form structures such as vesicles, liposomes, or membranes in an aqueous environment. Non-limiting examples, of lipids include fatty acids, glycerolipids (like monoglycerides, diglycerides, and triglycerides), phospholipids, sphingolipids, sterol lipids, prenol lipids, saccharolipids, and polyketides. A pharmaceutical composition disclosed herein may comprise a lipid such as, e.g. an oil, an oil-based liquid, a fat, a fatty acid, a wax, a fatty acid ester, a fatty acid salt, a fatty alcohol, a glyceride (mono-, di- or tri-glyceride), a phospholipids, a glycol ester, a sucrose ester, a glycerol oleate derivative, a medium chain triglyceride, or a mixture thereof.

A lipid useful in the pharmaceutical compositions disclosed herein may be a pharmaceutically-acceptable fatty acid. A fatty acid comprises a carboxylic acid with a long unbranched hydrocarbon chain which may be either saturated or unsaturated. Thus arrangement confers a fatty acid with a polar, hydrophilic end, and a nonpolar, hydrophobic end that is insoluble in water. Most naturally occurring fatty acids have a hydrocarbon chain of an even number of carbon atoms, typically between 4 and 24 carbons, and may be attached to functional groups containing oxygen, halogens, nitrogen, and sulfur. Synthetic or non-natural fatty acids may have a hydrocarbon chain of any number of carbon atoms from between 3 and 40 carbons. Where a double bond exists, there is the possibility of either a cis or a trans geometric isomerism, which significantly affects the molecule's molecular configuration. Cis-double bonds cause the fatty acid chain to bend, an effect that is more pronounced the more double bonds there are in a chain. Most naturally occurring fatty acids are of the cis configuration, although the trans form does exist in some natural and partially hydrogenated fats and oils. Examples of fatty acids include, without limitation, Capryllic acid (8:0), pelargonic acid (9:0), Capric acid (10:0), Undecylic acid (11:0), Laurie acid (12:0), Tridecylic acid (13:0), Myristic acid (14:0), Myristoleic acid (14:1), Pentadecyclic acid (15:0), Palmitic acid (16:0), Palmitoleic acid (16:1), Sapienic acid (16:1), Margaric acid (17:0), Stearic acid (18:0), Oleic acid (18:1), Elaidic acid (18:1), Vaccenic acid (18:1), Linoleic acid (18:2), Linoelaidic acid (18:2), α-Linolenic acid (18:3), γ-Linolenic acid (18:3), Stearidonic acid (18:4), Nonadecylic acid (19:0), Arachidic acid (20:0), Eicosenoic acid (20:1), Dihomo-γ-linolenic acid (20:3), Mead acid (20:3), Arachidonic acid (20:4), Eicosapentaenoic acid (20:5), Heneicosylic acid (21:0), Behenic acid (22:0), Erucic acid (22:1), Docosahexaenoic acid (22:6), Tricosylic acid (23:0), Lignoceric acid (24:0), Nervonic acid (24:1), Pentacosylic acid (25:0), Cerotic acid (26:0), Heptacosylic acid (27:0), Montanic acid (28:0), Nonacosylic acid (29:0), Melissic acid (30:0), Henatriacontylic acid (31:0), Lacceroic acid (32:0), Psyllic acid (33:0), Geddic acid (34:0), Ceroplastic acid (35:0), and Hexatriacontylic acid (36:0).

In an embodiment, an adjuvant may be a pharmaceutically-acceptable saturated or unsaturated fatty acid. In aspects of this embodiment, a saturated or unsaturated fatty acid comprises, e.g., at least 8, at least 10, at least 12, at least 14, at least 16, at least 18, at least 20, at least 22, at least 24, at least 26, at least 28, or at least 30 carbon atoms, In other aspects of this embodiment, a saturated or unsaturated fatty acid comprises, e.g., between 4 and 24 carbon atoms, between 6 and 24 carbon atoms, between 8 and 24 carbon atoms, between 10 and 24 carbon atoms, between 12 and 24 carbon atoms, between 14 and 24 carbon atoms, or between 16 and 24 carbon atoms, between 4 and 22 carbon atoms, between 6 and 22 carbon atoms, between 8 and 22 carbon atoms, between 10 and 22 carbon atoms, between 12 and 22 carbon atoms, between 14 and 22 carbon atoms, or between 16 and 22 carbon atoms, between 4 and 20 carbon atoms, between 6 and 20 carbon atoms, between 8 and 20 carbon atoms, between 10 and 20 carbon atoms, between 12 and 20 carbon atoms, between 14 and 20 carbon atoms, or between 16 and 20 carbon atoms. If unsaturated, the fatty acid may have, e.g., 1 or more, 2 or more, 3 or more, 4 or more, 5 or more, or 6 or more double bonds.

In aspects of this embodiment, a pharmaceutically-acceptable saturated or unsaturated fatty acid is liquid at room temperature. The melting point of a fatty acid is largely determined by the degree of saturation/unsaturation of the hydrocarbon chain. In aspects of this embodiment, a saturated or unsaturated fatty acid has a melting point temperature of, e.g., 20° C. or below, 15° C. or below, 10° C. or below, 5° C. or below, 0° C. or below, −5° C. or below, −10° C. or below, −15° C. or below, or −20° C. or below. In other aspects of this embodiment, a saturated or unsaturated fatty acid has a melting point temperature in the range of, e.g., about −20° C. to about 20° C., about −20° C. to about 18° C., about −20° C. to about 16° C., about −20° C. to about 12° C., about −20° C. to about 8° C., about −20° C. to about 4° C., about −20° C. to about 0° C., about −15° C. to about 20° C., about −15° C. to about 18° C., about −15° C. to about 16° C., about −15° C. to about 12° C., about −15° C. to about 8° C., about −15° C. to about 4° C., about −15° C. to about 0° C.

In another embodiment, an adjuvant may comprise one kind of pharmaceutically-acceptable fatty acid. In aspects of this embodiment, an adjuvant may comprise only palmitic acid, only stearic acid, only oleic acid, only linoleic acid, or only linolenic acid.

In another embodiment, an adjuvant may comprise a plurality of different pharmaceutically-acceptable fatty acids. In aspects of this embodiment, an adjuvant may comprise, e.g., two or more different fatty acids, three or more different fatty acids, four or more different fatty acids, five or more different fatty acids, or six or more different fatty acids.

In other aspects of this embodiment, an adjuvant may comprise two or more different pharmaceutically-acceptable fatty acids including at least palmitic acid, stearic acid, oleic acid, linoleic acid and/or linolenic acid, and any combination thereof. In other aspects of this embodiment, an adjuvant may comprise a ratio of palmitic acid and/or stearic acid and/or oleic acid:linolenic acid and/or linoleic acid of, e.g., at least 2:1, at least 3:1, at least 4:1, at least 5:1, at least 6:1, at least 7:1, at least 8:1, at least 9:1, at least 10:1, at least 15:1, or at least 20:1. In yet other aspects of this embodiment, an adjuvant may comprise a ratio of palmitic acid and/or stearic acid and/or oleic acid:linolenic acid and/or linoleic acid in a range of, e.g., about 1:1 to about 20:1, about 2:1 to about 15:1, about 4:1 to about 12:1, or about 6:1 to about 10:1.

In other aspects of this embodiment, an adjuvant may comprise four or more different pharmaceutically-acceptable fatty acids including at least palmitic acid, stearic acid, oleic acid, linoleic acid and/or linolenic acid, and any combination thereof. In other aspects of this embodiment, an adjuvant may comprise a ratio of palmitic acid; stearic acid:linolenic acid:linoleic acid of, e.g., 10:10:1:1, 9:9:1:1, 8:8:1:1, 7:7:1:1, 6:6:1:1, 5:5:1:1, 4:4:1:1, 3:3:1:1, 2:2:1:1, or 1:1:1:1. In other aspects of this embodiment, an adjuvant may comprise a ratio of palmitic acid; stearic acid:linolenic acid:linoleic acid in a range of, e.g., about 10:10:1:1 to about 6:6:1:1, about 8:8:1:1 to about 4:4:1:1, or about 5:5:1:1 to about 1:1:1:1.

A lipid useful in the pharmaceutical compositions disclosed herein may be a pharmaceutically-acceptable omega fatty acid. Non-limiting examples of an omega fatty acid include omega-3, omega-6, and omega-9. Omega-3 fatty acids (also known as n-3 fatty acids or ω-3 fatty acids) are a family of essential unsaturated fatty acids that have in common a final carbon-carbon double bond in the n-3 position, that is, the third bond, counting from the methyl end of the fatty acid. The omega-3 fatty acids are "essential" fatty acids because they are vital for normal metabolism and cannot be synthesized by the human body. An omega-3 fatty acid includes, without limitation, Hexadecatrienoic acid (16:3), α-Linolenic acid (18:3), Stearidonic acid (18:4), Eicosatrienoic acid (20:3), Eicosatetraenoic acid (20:4), Eicosapentaenoic acid (20:5), Heneicosapentaenoic acid (21:5), Docosapentaenoic acid (22:5), Clupanodonic acid (22:5), Docosahexaenoic acid (22:6), Tetracosapentaenoic acid (24:5), Tetracosahexaenoic acid (Nisinic acid) (24:6).

Omega-6 fatty acids (also known as n-6 fatty acids or ω-6 fatty acids) are a family of unsaturated fatty acids that have in common a final carbon-carbon double bond in the n-6 position, that is, the sixth bond, counting from the methyl end of the fatty acid. An omega-6 fatty acid includes, without limitation, Linoleic acid (18:2), Gamma-linolenic acid (18:3), Calendic acid (18:3), Eicosadienoic acid (20:2), Dihomo-gamma-linolenic acid (20:3), Arachidonic acid (20:4), Docosadienoic acid (22:2), Adrenic acid (22:4), Docosapentaenoic acid (22:5), Tetracosatetraenoic acid (24:4), and Tetracosapentaenoic acid (24:5). Omega-9 fatty acids (also known as n-9 fatty acids or ω-9 fatty acids) are a family of unsaturated fatty acids that have in common a final carbon-carbon double bond in the n-9 position, that is, the ninth bond, counting from the methyl end of the fatty acid. An omega-9 fatty acid includes, without limitation, oleic acid (18:1), Elaidic acid (18:1), Eicosenoic acid (20:1), Mead acid (20:3), Erucic acid (22:1), and Nervonic acid (24:1).

A lipid useful in the pharmaceutical compositions disclosed herein may be a pharmaceutically-acceptable oil. An oil includes any fatty acid that is liquid at normal room temperature, such as, e.g. about 20° C. In contrast, a fat includes any fatty acid that is solid at normal room temperature, such as, e.g. about 20° C. An oil suitable as a lipid useful in the pharmaceutical compositions disclosed herein, may be a natural oil or a vegetable oil. Examples of suitable natural oils include, without limitation, mineral oil, triacetin, ethyl oleate, a hydrogenated natural oil, or a mixture thereof. Examples of suitable vegetable oils include, without limitation, almond oil, arachis oil, avocado oil, canola oil, castor oil, coconut oil, corn oil, cottonseed oil, grape seed oil, hazelnut oil, hemp oil, linseed oil (flax seed oil), olive oil, palm oil, peanut oil, rapeseed oil, rice bran oil, safflower oil, sesame oil, soybean oil, soya oil, sunflower oil, walnut oil, wheat germ oil, or a mixture thereof. Each of these oils is commercially available from a number of sources well recognized by those skilled in the art.

An oil is typically a mixture of various fatty acids. For example, Rapeseed oil, obtained from the seeds of *Brassica napus*, includes both omega-6 and omega-3 fatty acids in a ratio of about 2:1. As another example, linseed oil, obtained from the seeds of *Linum usitatissimum*, includes abut 7% palmitic acid, about 3.4-4.6% stearic acid, about 18.5-22.6% oleic acid, about 14.2-17% linoleic acid, and about 51.9-55.2% α-linolenic acid. In aspects of this embodiment, a pharmaceutical composition comprises an oil including at least two different fatty acids, at least three different fatty acids, at least four different fatty acids, at least five different fatty acids, or at least six different fatty acids.

A lipid useful in the pharmaceutical compositions disclosed herein may be a pharmaceutically-acceptable glycerolipid. Glycerolipids are composed mainly of mono-, di-, and tri-substituted glycerols. One group of glycerolipids is the glycerides, where one, two, or all three hydroxyl groups of glycerol are each esterified using a fatty acid to produce monoglycerides, diglycerides, and triglycerides, respectively. In these compounds, each hydroxyl groups of glycerol may be esterified by different fatty acids. Additionally, glycerides may be acetylated to produce acetylated monoglycerides, acetylated diglycerides, and acetylated triglycerides. One group of glycerolipids is the glycerides, where one, two, or all three hydroxyl groups of glycerol have sugar residues attached via a glycosidic linkage.

Aspects of the present specification disclose, in part, a pharmaceutically-acceptable stabilizing agent. A stabilizing agent reduces or eliminates formation of esters of a therapeutic compound that may result as a unwanted reaction with the particular solvent used. A stabilizing agent include, without limitation, water, a sacrificial acid comprising a fatty acid component and acetic acid, ethyl acetate, a sodium acetate/acetic acid (E262), a monoglyceride, an acetylated monoglyceride, a diglyceride, an acetylated monoglyceride, an acetylated diglyceride, a fatty acid, and a fatty acid salt.

In one embodiment, a pharmaceutically-acceptable stabilizing agent may comprise a pharmaceutically-acceptable emulsifying agent. An emulsifying agent (also known as an emulgent) is a substance that stabilizes an emulsion comprising a liquid dispersed phase and a liquid continuous phase by increasing its kinetic stability. Thus, in situations where the solvent and adjuvant used to make a pharmaceutical composition disclosed herein are normally immiscible, an emulsifying agent disclosed herein is used to create a homogenous and stable emulsion. An emulsifying agent includes, without limitation, a surfactant, a polysaccharide, a lectin, and a phospholipid.

In an aspect of this embodiment, an emulsifying agent may comprise a surfactant. As used hereon, the term "surfactant" refers to a natural or synthetic amphiphilic compound. A surfactant can be non-ionic, zwitterionic, or ionic. Non-limiting examples of surfactants include polysorbates like polysorbate 20 (TWEEN® 20), polysorbate 40 (TWEEN® 40), polysorbate 60 (TWEEN® 60), polysorbate 61 (TWEEN® 61), polysorbate 65 (TWEEN® 65), polysorbate 80 (TWEEN® 80), and polysorbate 81 (TWEEN® 81); poloxamers (polyethylene-polypropylene copolymers), like Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), Poloxamer 407 (PLURONIC® F127), polyoxyethyleneglycol dodecyl ethers, like BRIJ® 30, and BRIJ® 35; 2-dodecoxyethanol (LUBROL®-PX); polyoxyethylene octyl phenyl ether (TRITON® X-100); sodium dodecyl sulfate (SDS); 3-[(3-Cholamidopropyl)dimethylammonio]-1-propanesulfonate (CHAPS); 3-[(3-Cholamidopropyl)dimethylammonio]-2-hydroxy-1-propanesulfonate (CHAPSO); sucrose monolaurate; and sodium cholate. Other non-limiting examples of surfactant excipients can be found in, e.g., Ansel, supra, (1999); Gennaro, supra, (2000); Hardman, supra, (2001); and Rowe, supra, (2003), each of which is hereby incorporated by reference in its entirety.

In an aspect of this embodiment, an emulsifying agent may comprise a polysaccharide. Non-limiting examples of polysaccharides include guar gum, agar, alginate, calgene, a dextran (like dextran 1K, dextran 4K, dextran 40K, dextran 60K, and dextran 70K), dextrin, glycogen, inulin, starch, a starch derivative (like hydroxymethyl starch, hydroxyethyl starch, hydroxypropyl starch, hydroxybutyl starch, and hydroxypentyl starch), hetastarch, cellulose, FICOLL, methyl cellulose (MC), carboxymethyl cellulose (CMC), hydroxyethyl cellulose (HEC), hydroxypropyl cellulose (HPC), hydroxyethyl methyl cellulose (HEMC), hydroxypropyl methyl cellulose (HPMC); polyvinyl acetates (PVA); polyvinyl pyrrolidones (PVP), also known as povidones, having a K-value of less than or equal to 18, a K-value greater than 18 or less than or equal to 95, or a K-value greater than 95, like PVP 12 (KOLLIDON® 12), PVP 17 (KOLLIDON® 17), PVP 25 (KOLLIDON® 25), PVP 30 (KOLLIDON® 30), PVP 90 (KOLLIDON® 90); and polyethylene imines (PEI).

In an aspect of this embodiment, an emulsifying agent may comprise a lectin. Lectins are sugar-binding proteins that are highly specific for their sugar moieties. Lectins may be classified according to the sugar moiety that they bind to, and include, without limitation, mannose-binding lectins, galactose/N-acetylgalactosamine-binding lectins, N-acetylgluxosamine-binding lectins, N-acetylneuramine-binding lectins, N-acetylneuraminic acid-binding lectins, and fucose-binding lectins. Non-limiting examples of surfactants include concanavain A, lentil lectin, snowdrop lectin, Roin, peanut agglutinin, jacain, hairy vetch lectin, wheat germ agglutinin, elderberry lectin, *Maackia anurensis* leukoagglutinin, *Maackia anurensis* hemoagglutinin, *Ulex europaeus* agglutinin, and *Aleuria aurantia* lectin.

In an aspect of this embodiment, an emulsifying agent may comprise a phospholipid. The structure of the phospholipid generally comprises a hydrophobic tail and a hydrophilic head and is amphipathic in nature. Most phospholipids contain a diglyceride, a phosphate group, and a simple organic molecule such as choline; one exception to this rule is sphingomyelin, which is derived from sphingosine instead of glycerol. Phospholipids include, without limitation, diacylglycerides and phosphosphingolipids. Non-limiting examples of diacylglycerides include a phosphatidic acid (phosphatidate) (PA), a phosphatidylethanolamine (cephalin) (PE), a phosphatidylcholine (lecithin) (PC), a phosphatidylserine (PS), and a phosphoinositide including phosphatidylinositol (PI), phosphatidylinositol phosphate (PIP), phosphatidylinositol bisphosphate (PIP2), and phosphatidylinositol triphosphate (PIP3). Non-limiting examples of phosphosphingolipids include a ceramide phosphorylcholine (sphingomyelin) (SPH), ceramide phosphorylethanolamine (sphingomyelin) (Cer-PE), and ceramide phosphorylglycerol.

In one embodiment, a pharmaceutically-acceptable stabilizing agent does not comprise a pharmaceutically-acceptable emulsifying agent.

In another embodiment, a pharmaceutical composition does not comprise a pharmaceutically-acceptable emulsifying agent.

The pharmaceutical compositions disclosed herein act as a delivery system that enable a therapeutic compound disclosed herein to be more effectively delivered or targeted to a cell type, tissue, organ, or region of the body in a manner that more effectively inhibits a pro-inflammatory response. This inhibition results in an improved treatment of a chronic inflammation. For example, a pharmaceutical composition disclosed herein may facilitate the delivery of a therapeutic compound disclosed herein into macrophages. One possible mechanism that achieves this selective biodistribution is that the pharmaceutical compositions disclosed herein may be designed to take advantage of the activity of chylomicrons. Chylomicrons are relatively large lipoprotein particles having a diameter of 75 nm to 1,200 nm. Comprising triglycerides (85-92%), phospholipids (6-12%), cholesterol (1-3%) and apolipoproteins (1-2%), chylomicrons transport dietary lipids from the intestines to other locations in the body. Chylomicrons are one of the five major groups of lipoproteins, the others being VLDL, IDL, low-density lipoproteins (LDL), high-density lipoproteins (HDL), that enable fats and cholesterol to move within the water-based solution of the bloodstream.

During digestion, fatty acids and cholesterol undergo processing in the gastrointestinal tract by the action of pancreatic juices including lipases and emulsification with bile salts to generate micelles. These micelles allow the absorption of lipid as free fatty acids by the absorptive cells of the small intestine, known as enterocytes. Once in the enterocytes, triglycerides and cholesterol are assembled into nascent chylomicrons. Nascent chylomicrons are primarily composed of triglycerides (85%) and contain some cholesterol and cholesteryl esters. The main apolipoprotein component is apolipoprotein B-48 (APOB48). These nascent chylomicrons are released by exocytosis from enterocytes into lacteals, lymphatic vessels originating in the villi of the small intestine, and are then secreted into the bloodstream at the thoracic duct's connection with the left subclavian vein.

While circulating in lymph and blood, chylomicrons exchange components with HDL. The HDL donates apolipoprotein C-II (APOC2) and apolipoprotein E (APOE) to the nascent chylomicron and thus converts it to a mature chylomicron (often referred to simply as "chylomicron"). APOC2 is the cofactor for lipoprotein lipase (LPL) activity. Once triglyceride stores are distributed, the chylomicron returns APOC2 to the HDL (but keeps APOE), and, thus, becomes a chylomicron remnant, now only 30-50 nm. APOB48 and APOE are important to identify the chylomicron remnant in the liver for endocytosis and breakdown into lipoproteins (VLDL, LDL and HDL). These lipoproteins are processed and stored by competent cells, including, e.g., hepatocytes, adipocytes and macrophages. Thus, without wishing to be limited by any theory, upon oral administration of the pharmaceutical compositions disclosed herein are processed into micelles while in the gastrointestinal tract, absorbed by enterocytes and assembled into nascent chylomicrons, remain associated with chylomicron remnants taken up by the liver, and ultimately loaded into macrophages.

Aspects of the present specification disclose, in part, a method of preparing a pharmaceutical composition disclosed herein. A method disclosed herein comprises the step of contacting a pharmaceutically-acceptable adjuvant disclosed herein with a therapeutic compound disclosed herein under conditions which allow the therapeutic compound to dissolve in the pharmaceutically-acceptable adjuvant, thereby forming a pharmaceutical composition disclosed herein.

Aspects of the present specification disclose, in part, a method of preparing a pharmaceutical composition disclosed herein. A method disclosed herein comprises the steps of a) contacting a pharmaceutically-acceptable solvent disclosed herein with a therapeutic compound disclosed herein under conditions which allow the therapeutic compound to dissolve in the pharmaceutically-acceptable solvent, thereby forming a solution; and b) contacting the solution formed in step (a) with a pharmaceutically-acceptable adjuvant disclosed herein under conditions which allow the formation of a pharmaceutical composition. The methods of preparing disclosed herein may further comprise a step (c) of removing the pharmaceutically-acceptable solvent from the pharmaceutical composition.

The amount of a therapeutic compound that is contacted with the pharmaceutically-acceptable solvent in step (a) of the method may be in any amount desired. Factors used to determine the amount of a therapeutic compound used include, without limitation, the final amount the therapeutic compound desired in the pharmaceutical composition, the desired concentration of a therapeutic compound in the solution, the hydrophobicity of the therapeutic compound, the lipophobicity of the therapeutic compound, the temperature under which the contacting step (a) is performed, and the time under which the contacting step (a) is performed The volume of a pharmaceutically-acceptable solvent used in step (a) of the method may be any volume desired. Factors used to determine the volume of a pharmaceutically-acceptable solvent used include, without limitation, the final amount of a pharmaceutical composition desired, the desired concentration of a therapeutic compound in the solution, the hydrophobicity of the therapeutic compound, and the lipophobicity of the therapeutic compound.

In aspects of this embodiment, the amount of a therapeutic compound that is contacted with the solvent in step (a) may be, e.g., at least 10 mg, at least 20 mg, at least 30 mg, at least 40 mg, at least 50 mg, at least 60 mg, at least 70 mg, at least 80 mg, at least 90 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg. In other aspects of this embodiment, the amount of a therapeutic compound that is contacted with the solvent in step (a) may be in the range of, e.g., about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In other aspects of this embodiment, the amount of a therapeutic compound that is dissolved in the solvent in step (a) may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, or about 200 mg to about 1,500 mg.

Step (a) may be carried out at room temperature, in order to allow a therapeutic compound to dissolve fully in the pharmaceutically-acceptable solvent. However, in other embodiments of the method, step (a) may be carried out at a temperature that is greater than room temperature, e.g., greater than 21° C., greater than 25° C., greater than 30° C., greater than 35° C. or greater than 37° C. In certain cases, Step (a) may be carried out at temperatures below room temperature, in order to allow a therapeutic compound to dissolve fully in solvent. However, in other embodiments of the method, step (a) may be carried out at a temperature that is less than room temperature, e.g., less than 10° C., greater than 5° C., greater than 0° C., greater than −10° C. or greater than −20° C. The contacting in Step (a) may comprise mixing the therapeutic compound and the pharmaceutically-acceptable solvent, e.g., by stirring, inversion, sonication, or vortexing. The mixing may be carried out for, e.g., at least 1 second, at least 5 seconds, at least 10 seconds, at least 20 seconds, at least 30 seconds, at least 45 seconds, at least 60 seconds, or more, until the therapeutic compound is fully dissolved in the solvent.

After contacting, the concentration of a therapeutic compound disclosed herein in the solution may be in any concentration desired. In aspects of this embodiment, the concentration of a therapeutic compound disclosed herein in the solution may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the concentration of a therapeutic compound disclosed herein in the solution may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

The volume of a pharmaceutically-acceptable adjuvant used in step (b) of the method may be any volume desired. Factors used to determine the volume of a pharmaceutically-acceptable adjuvant used include, without limitation, the final amount of a pharmaceutical composition desired, the desired concentration of a therapeutic compound in the pharmaceutical composition, the ratio of solvent:adjuvant used, and the miscibility of solvent and adjuvant.

In aspects of this embodiment, the ratio of solution:adjuvant may be, e.g., at least 5:1, at least 4:1, at least 3:1, at least 2:1, at least 0:1, at least 1:1, at least 1:2, at least 1:3, at least 1:4, at least 1:5, at least 1:6, at least 1:7, at least 1:8, at least 1:9, at least 1:10, at least 1:15, at least 1:20, or at least 1:25. In other aspects of this embodiment, the ratio of solution:adjuvant may be in a range of, e.g., about 5:1 to about 1:25, about 4:1 to about 1:25, about 3:1 to about 1:25, about 2:1 to about 1:25, about 0:1 to about 1:25, about 1:1 to about 1:25, about 1:2 to about 1:25, about 1:3 to about 1:25, about 1:4 to about 1:25, about 1:5 to about 1:25, about 5:1 to about 1:20, about 4:1 to about 1:20, about 3:1 to about 1:20, about 2:1 to about 1:20, about 0:1 to about 1:20, about 1:1 to about 1:20, about 1:2 to about 1:20, about 1:3 to about 1:20, about 1:4 to about 1:20, about 1:5 to about 1:20, about 5:1 to about 1:15, about 4:1 to about 1:15, about 3:1 to about 1:15, about 1:15, about 0:1 to about 1:15, about 2:1 to about 1:15, about 1:1 to about 1:15, about 1:2 to about 1:15, about 1:3 to about 1:15, about 1:4 to about 1:15, about 1:5 to about 1:15, about 5:1 to about 1:12, about 4:1 to about 1:12, about 3:1 to about 1:12, about 1:12, about 2:1 to about 1:12, about 0:1 to about 1:12, about 1:1 to about 1:12, about 1:2 to about 1:12, about 1:3 to about 1:12, about 1:4 to about 1:12, about 1:5 to about 1:12, about 1:6 to about 1:12, about 1:7 to about 1:12, about 1:8 to about 1:12, about 5:1 to about 1:10, about 4:1 to about 1:10, about 3:1 to about 1:10, about 2:1 to about 1:10, about 0:1 to about 1:10, about 1:1 to about 1:10, about 1:2 to about 1:10, about 1:3 to about 1:10, about 1:4 to about 1:10, about 1:5 to about 1:10, about 1:6 to about 1:10, about 1:7 to about 1:10, or about 1:8 to about 1:10.

Step (b) may be carried out at room temperature, in order to allow the solution comprising the therapeutic compound to form the pharmaceutical composition. However, in other embodiments of the method, step (b) may be carried out at a temperature that is greater than room temperature, e.g., greater than 21° C., greater than 25° C., greater than 30° C., greater than 35° C. or greater than 37° C. In certain cases, Step (b) may be carried out at temperatures below room temperature, in order to allow a therapeutic compound to dissolve fully in a pharmaceutically-acceptable solvent. However, in other embodiments of the method, step (b) may be carried out at a temperature that is less than room temperature, e.g., less than 10° C., greater than 5° C., greater than 0° C., greater than −10° C. or greater than −20° C. The contacting in Step (b) may comprise mixing the solution and the pharmaceutically-acceptable adjuvant, e.g., by stirring, inversion, sonication, or vortexing. The mixing may be carried out for, e.g., at least 1 second, at least 5 seconds, at least 10 seconds, at least 20 seconds, at least 30 seconds, at least 45 seconds, at least 60 seconds, or more, until the pharmaceutical composition is formed.

In Step (c), the solvent removal from a pharmaceutical composition may be accomplished using one of a variety of procedures known in the art, including, without limitation, evaporation, dialyzation, distillation, lypholization, and filtration. These removal procedures may be done under conditions of ambient atmosphere, under low pressure, or under a vacuum.

In one embodiment, Step (c) may result in the complete removal of a pharmaceutically-acceptable solvent from the pharmaceutical composition disclosed herein. In aspects of this embodiment, Step (c) may result in, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 93%, at least 95%, at least 97%, or at least 99% removal of a pharmaceutically-acceptable solvent from the pharmaceutical composition disclosed herein.

Step (c) is conducted at a temperature that allows for the evaporation of a pharmaceutically-acceptable solvent disclosed herein, and as such, an evaporation temperature is solvent dependant. Factors which influence an evaporation temperature of a solvent disclosed herein include, without limitation, the particular solvent used, the amount of solvent present, the particular therapeutic compound present, the particular adjuvant present, the stability of the therapeutic compound present, the reactivity of the therapeutic compound present, the particular atmospheric pressure used, the time desired for complete evaporation. Generally, a pharmaceutical composition will require heating if the evaporation step is conducted at ambient pressure, e.g., 1 atm. However, under high vacuum conditions, the evaporation step may be conducted at temperatures below ambient temperature, e.g., less than 22° C.

In one embodiment, removal of solvent from the pharmaceutical composition disclosed herein may be carried out at ambient atmospheric pressure and at a temperature above ambient temperature. In aspects of this embodiment, removal of solvent from the pharmaceutical composition disclosed herein may be carried out at ambient atmospheric pressure and at a temperature of, e.g., more than 25° C., more than 30° C., more than 35° C., more than 40° C., more than 45° C., more than 50° C., more than 55° C., more than 60° C., more than 65° C., more than 70° C., more than 80° C., or more than 25° C. In other aspects of this embodiment, removal of solvent from the pharmaceutical composition disclosed herein may be carried out at ambient atmospheric pressure and at a temperature in a range of, e.g., about 25° C. to about 100° C., about 25° C. to about 95° C., about 25° C. to about 90° C., about 25° C. to about 85° C., about 25° C. to about 80° C., about 25° C. to about 75° C., about 25° C. to about 70° C., about 25° C. to about 65° C., or about 25° C. to about 60° C.

In another embodiment, removal of solvent from the pharmaceutical composition disclosed herein may be carried out under vacuum and at a temperature below ambient temperature. In aspects of this embodiment, removal of solvent from the pharmaceutical composition disclosed herein may be carried out under vacuum and at a temperature of, e.g., less than 20° C., less than 18° C., less than 16° C., less than 14° C., less than 12° C., less than 10° C., less than 8° C., less than 6° C., less than 4° C., less than 2° C., or less than 0° C. In other aspects of this embodiment, removal of solvent from the pharmaceutical composition disclosed herein may be carried out under vacuum and at a temperature in a range of, e.g., about −20° C. to about 20° C., about −20° C. to about 18° C., about −20° C. to about 16° C., about −20° C. to about 14° C., about −20° C. to about 12° C., about −20° C. to about 10° C., about −20° C. to about 8° C., about −20° C. to about 6° C., about −20° C. to about 4° C., about −20° C. to about 2° C., about −20° C. to about 0° C., about −15° C. to about 20° C., about −10° C. to about 20° C., about −5° C. to about 20° C., about 0° C. to about 20° C., about −10° C. to about 20° C., about −10° C. to about 18° C., about −10° C. to about 16° C., about −10° C. to about 14° C., about −10° C. to about 12° C., about −10° C. to about 10° C., about −10° C. to about 8° C., about −10° C. to about 6° C., about −10° C. to about 4° C., about −10° C. to about 2° C., or about −10° C. to about 0° C.

The final concentration of a therapeutic compound disclosed herein in a pharmaceutical composition disclosed herein may be of any concentration desired. In an aspect of this embodiment, the final concentration of a therapeutic compound in a pharmaceutical composition may be a therapeutically effective amount. In other aspects of this embodiment, the final concentration of a therapeutic compound in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the final concentration of a therapeutic compound in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

A pharmaceutical composition produced using the methods disclosed herein may be a liquid formulation or a solid or semi-solid formulation. A liquid formulation can be formed by using various lipids like oils of other fatty acids that remain as liquids in the temperature range desired. In an embodiment, a pharmaceutical composition disclosed herein is liquid at room temperature. In aspects of this embodiment, a pharmaceutical composition disclosed herein may be formulated to be a liquid at a temperature of, e.g., about 25° C. or higher, about 23° C. or higher, about 21° C. or higher, about 19° C. or higher, about 17° C. or higher, about 15° C. or higher, about 12° C. or higher, about 10° C. or higher, about 8° C. or higher, about 6° C. or higher, about 4° C. or higher, or about 0° C. or higher.

A solid or semi-solid formulation disclosed herein takes advantage of the different melting point temperatures of the various adjuvants like fatty acids. Formation of a solid or semi-solid dosage form can be by modifying the respective concentrations of the fatty acids comprising a pharmaceutical composition disclosed herein. For example, linolenic acid has a melting point temperature ($T_m$) of about −11° C., linoleic acid has a $T_m$ of about −5° C., oleic acid has a $T_m$ of about 16° C., palmitic acid has a $T_m$ of about 61–62° C., and Stearic acid has a $T_m$ of about 67–72° C. Increasing the proportion(s) of palmitic, stearic or oleic acid would increase the overall melting temperature of a composition, while, conversely, increasing the proportion(s) of linoleic and linolenic acid would decrease the melting temperature of a composition. Thus, by controlling the types and amounts of the adjuvant components added, a pharmaceutical composition disclosed herein can be made that is substantially solid or semi-solid at room temperature, but melts when it is ingested, and reaches body temperature. The resulting melted composition readily forms micelles which are absorbed by the intestine, assembled into chylomicrons, and ultimately absorbed by macrophages. The solid dosage form may be a powder, granule, tablet, capsule or suppository.

In an embodiment, a pharmaceutical composition disclosed herein is solid at room temperature. In aspects of this embodiment, a pharmaceutical composition disclosed herein may be formulated to be a solid at a temperature of, e.g., about 35° C. or lower, about 33° C. or lower, about 31° C. or lower, about 29° C. or lower, about 27° C. or lower, about 25° C. or lower, about 23° C. or lower, about 21° C. or lower, about 19° C. or lower, about 17° C. or lower, about 15° C. or lower, about 12° C. or lower, about 10° C. or lower, about 8° C. or lower, about 6° C. or lower, about 4° C. or lower, or about 0° C. or lower.

In other aspects of this embodiment, a pharmaceutical composition disclosed has a melting point temperature of, e.g., 5° C. or higher, 10° C. or higher, 15° C. or higher, 22° C. or higher, 23° C. or higher, 24° C. or higher, 25° C. or higher, 26° C. or higher, 27° C. or higher, 28° C. or higher, 29° C. or higher, 30° C. or higher, 31° C. or higher, 32° C. or higher, 33° C. or higher, 34° C. or higher, or 35° C. or higher. In other aspects of this embodiment, a pharmaceutical composition disclosed has a melting point temperature in the range of, e.g., about 5° C. to about 24° C., about 10° C. to about 24° C. about 22° C. to about 24° C., about 23° C. to about 25° C., about 24° C. to about 26° C., about 25° C. to about 27° C., about 26° C. to about 28° C., about 27° C. to about 29° C., about 28° C. to about 30° C., about 29° C. to about 31° C., about 30° C. to about 32° C., about 31° C. to about 33° C., about 32° C. to about 34° C., about 33° C. to about 35° C. In other aspects of this embodiment, a pharmaceutical composition disclosed has a melting point temperature in the range of, e.g., about 22° C. to about 26° C., about 24° C. to about 28° C., about 26° C. to about 30° C., about 28° C. to about 32° C., or about 30° C. to about 34° C.

Aspects of the present specification disclose, in part, a method of treating an individual with a chronic inflammation. In one embodiment, the method comprises the step of administering to an individual in need thereof a pharmaceutical composition disclosed herein, wherein administration reduces a symptom associated with the chronic inflammation, thereby treating the individual.

Aspects of the present specification disclose, in part, treating an individual suffering from a chronic inflammation. As used herein, the term "treating," refers to reducing or eliminating in an individual a clinical symptom of a chronic inflammation; or delaying or preventing in an individual the onset of a clinical symptom of a chronic inflammation. For example, the term "treating" can mean reducing a symptom of a condition characterized by a chronic inflammation by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with chronic inflammation are well known and can be determined by a person of ordinary skill in the art by taking into account factors, including, without limitation, the location of the chronic inflammation, the cause of the chronic inflammation, the severity of the chronic inflammation, and/or the tissue or organ affected by the chronic inflammation. Those of skill in the art will know the appropriate symptoms or indicators associated with a specific type of chronic inflammation and will know how to determine if an individual is a candidate for treatment as disclosed herein.

Chronic inflammation symptoms include, without limitation, edema, hyperemia, erythema, bruising, tenderness, stiffness, swollenness, fever, chills, stuffy nose, stuffy head, breathing problems, fluid retention, blood clots, loss of appetite, increased heart rate, formation of granulomas, fibrinous, pus, non-viscous serous fluid, or ulcer and pain. The actual symptoms associated with a chronic inflammation are well known and can be determined by a person of ordinary skill in the art by taking into account factors, including, without limitation, the location of the inflammation, the cause of the inflammation, the severity of the inflammation, the tissue or organ affected, and the associated disorder.

Specific patterns of chronic inflammation are seen during particular situations that arise in the body, such as when inflammation occurs on an epithelial surface, or pyogenic bacteria are involved. For example, granulomatous inflammation is an inflammation resulting from the formation of granulomas arising from a limited but diverse number of diseases, include, without limitation, tuberculosis, leprosy, sarcoidosis, and syphilis. Purulent inflammation is an inflammation resulting in large amount of pus, which consists of neutrophils, dead cells, and fluid. Infection by pyogenic bacteria such as staphylococci is characteristic of this kind of inflammation. Serous inflammation is an inflammation resulting from copious effusion of non-viscous serous fluid, commonly produced by mesothelial cells of serous membranes, but may be derived from blood plasma. Skin blisters exemplify this pattern of inflammation. Ulcerative inflammation is an inflammation resulting from the necrotic loss of tissue from the epithelial surface, exposing lower layers and forming an ulcer.

A chronic inflammation symptom can be associated with a large, unrelated group of disorders which underlay a variety of diseases and disorders. The immune system is often involved with chronic inflammatory disorders, demonstrated in both allergic reactions and some myopathies, with many immune system disorders resulting in abnormal inflammation. Non-immune diseases with etiological origins in chronic inflammatory processes include cancer, atherosclerosis, and ischaemic heart disease. Non-limiting examples of disorders exhibiting chronic inflammation as a symptom include, without limitation, acne, acid reflux/heartburn, age related macular degeneration (AMD), allergy, allergic rhinitis, Alzheimer's disease, amyotrophic lateral sclerosis, anemia, appendicitis, arteritis, arthritis, asthma. atherosclerosis, autoimmune disorders, balanitis, blepharitis, bronchiolitis, bronchitis, a bullous pemphigoid, burn, bursitis, cancer, cardiac arrest, carditis, celiac disease, cellulitis, cervicitis, cholangitis, cholecystitis, chorioamnionitis, chronic obstructive pulmonary disease (COPD), cirrhosis, colitis, congestive heart failure, conjunctivitis, cyclophosphamide-induced cystitis, cystic fibrosis, cystitis, common cold, dacryoadenitis, dementia, dermatitis, dermatomyositis, diabetes, diabetic neuropathy, diabetic retinopathy, diabetic nephropathy, diabetic ulcer, digestive system disease, eczema, emphysema, encephalitis, endocarditis, endometritis, enteritis, enterocolitis, epicondylitis, epididymitis, fasciitis, fibromyalgia, fibrosis, fibrositis, gastritis, gastroenteritis, gingivitis, glomerulonephritis, glossitis, heart disease, heart valve dysfunction, hepatitis, hidradenitis suppurativa, Huntington's disease, hyperlipidemic pancreatitis, hypertension, ileitis, infection, inflammatory bowel disease, inflammatory cardiomegaly, inflammatory neuropathy, insulin resistance, interstitial cystitis, interstitial nephritis, iritis, ischemia, ischemic heart disease, keratitis, keratoconjunctivitis, laryngitis, lupus nephritis, mastitis, mastoiditis, meningitis, metabolic syndrome (syndrome X), a migraine, multiple sclerosis, myelitis, myocarditis, myositis, nephritis, non-alcoholic steatohepatitis, obesity, omphalitis, oophoritis, orchitis, osteochondritis, osteopenia, osteomyelitis, osteoporosis, osteitis, otitis, pancreatitis, Parkinson's disease, parotitis, pelvic inflammatory disease, pemphigus vularis, pericarditis, peritonitis, pharyngitis, phlebitis, pleuritis, pneumonitis, polycystic nephritis, proctitis, prostatitis, psoriasis, pulpitis, pyelonephritis, pylephlebitis, renal failure, reperfusion injury, retinitis, rheumatic fever, rhinitis, salpingitis, sarcoidosis, sialadenitis, sinusitis, spastic colon, stenosis, stomatitis, stroke, surgical complication, synovitis, tendonitis, tendinosis, tenosynovitis, thrombophlebitis, tonsillitis, trauma, traumatic brain injury, transplant rejection, trigonitis, tuberculosis, tumor, urethritis, ursitis, uveitis, vaginitis, vasculitis, and vulvitis. See also, Eric R. First, Application of Botulinum Toxin to the Management of Neurogenic Inflammatory Disorders, U.S. Pat. No. 6,063,768, which is hereby incorporated by reference in its entirety.

In one embodiment, a chronic inflammation comprises a tissue inflammation. Tissue inflammation is a chronic inflammation that is confined to a particular tissue or organ. In aspect of this embodiment, a tissue inflammation comprises, e.g., a skin inflammation, a muscle inflammation, a tendon inflammation, a ligament inflammation, a bone inflammation, a cartilage inflammation, a lung inflammation, a heart inflammation, a liver inflammation, a pancreatic inflammation, a kidney inflammation, a bladder inflammation, a stomach inflammation, an intestinal inflammation, a neuron inflammation, and a brain inflammation.

In another embodiment, a chronic inflammation comprises a systemic inflammation. Although the processes involved are identical to tissue inflammation, systemic inflammation is not confined to a particular tissue but in fact overwhelms the body, involving the endothelium and other organ systems. When it is due to infection, the term sepsis is applied, with the terms bacteremia being applied specifically for bacterial sepsis and viremia specifically to viral sepsis. Vasodilation and organ dysfunction are serious problems associated with widespread infection that may lead to septic shock and death.

In another embodiment, a chronic inflammation comprises an arthritis. Arthritis includes a group of conditions involving damage to the joints of the body due to the inflammation of the synovium including, without limitation osteoarthritis, rheumatoid arthritis, juvenile idiopathic arthritis, spondyloarthropathies like ankylosing spondylitis, reactive arthritis (Reiter's syndrome), psoriatic arthritis, enteropathic arthritis associated with inflammatory bowel disease, Whipple disease and Behcet disease, septic arthritis, gout (also known as gouty arthritis, crystal synovitis, metabolic arthritis), pseudogout (calcium pyrophosphate deposition disease), and Still's disease. Arthritis can affect a single joint (monoarthritis), two to four joints (oligoarthritis) or five or more joints (polyarthritis) and can be either an auto-immune disease or a non-autoimmune disease.

In another embodiment, a chronic inflammation comprises an autoimmune disorder. Autoimmune diseases can be broadly divided into systemic and organ-specific autoimmune disorders, depending on the principal clinico-pathologic features of each disease. Systemic autoimmune diseases include, without limitation, systemic lupus erythematosus (SLE), Sjögren's syndrome, Scleroderma, rheumatoid arthritis and polymyositis. Local autoimmune diseases may be endocrinologic (Diabetes Mellitus Type 1, Hashimoto's thyroiditis, Addison's disease etc.), dermatologic (pemphigus vulgaris), hematologic (autoimmune haemolytic anemia), neural (multiple sclerosis) or can involve virtually any circumscribed mass of body tissue. Types of autoimmune disorders include, without limitation, acute disseminated encephalomyelitis (ADEM), Addison's disease, an allergy or sensitivity, amyotrophic lateral sclerosis, anti-phospholipid antibody syndrome (APS), arthritis, autoimmune hemolytic anemia, autoimmune hepatitis, autoimmune inner ear disease, autoimmune pancreatitis, bullous pemphigoid, celiac disease, Chagas disease, chronic obstructive pulmonary disease (COPD), diabetes mellitus type 1 (IDDM), endometriosis, fibromyalgia, Goodpasture's syndrome, Graves' disease, Guillain-Barre syndrome (GBS), Hashimoto's thyroiditis, hidradenitis suppurativa, idiopathic thrombocytopenic purpura, inflammatory bowel disease, interstitial cystitis, lupus (including discoid lupus erythematosus, drug-induced lupus erythematosus. lupus nephritis, neonatal lupus, subacute cutaneous lupus erythematosus and systemic lupus erythematosus), morphea, multiple sclerosis (MS), myasthenia gravis, myopathies, narcolepsy, neuromyotonia, pemphigus vulgaris, pernicious anaemia, primary biliary cirrhosis, recurrent disseminated encephalomyelitis (multiphasic disseminated encephalomyelitis), rheumatic fever, schizophrenia, scleroderma, Sjögren's syndrome, tenosynovitis, vasculitis, and vitiligo. See Pamela D. Van Schaack & Kenneth L. Tong, Treatment of Autoimmune Disorder with a Neurotoxin, U.S. Patent Publication 2006/138059, which is hereby incorporated by reference in its entirety.

In another embodiment, a chronic inflammation comprises a myopathy. Myopathies are caused when the immune system inappropriately attacks components of the muscle, leading to inflammation in the muscle. A myopathy includes an inflammatory myopathy and an auto-immune myopathy. Myopathies include, without limitation, dermatomyositis, inclusion body myositis, and polymyositis.

In another embodiment, a chronic inflammation comprises a vasculitis. Vasculitis is a varied group of disorders featuring inflammation of a vessel wall including lymphatic vessels and blood vessels like veins (phlebitis), arteries (arteritis) and capillaries due to leukocyte migration and resultant damage. The inflammation may affect any size blood vessel, anywhere in the body. It may affect either arteries and/or veins. The inflammation may be focal, meaning that it affects a single location within a vessel; or it may be widespread, with areas of inflammation scattered throughout a particular organ or tissue, or even affecting more than one organ system in the body. Vasculitis include, without limitation, Buerger's disease (thromboangiitis obliterans), cerebral vasculitis (central nervous system vasculitis), Churg-Strauss arteritis, cryoglobulinemia, essential cryoglobulinemic vasculitis, giant cell (temporal) arteritis, Golfer's vasculitis, Henoch-Schonlein purpura, hypersensitivity vasculitis (allergic vasculitis), Kawasaki disease, microscopic polyarteritis/polyangiitis, polyarteritis nodosa, polymyalgia rheumatica (PMR), rheumatoid vasculitis, Takayasu arteritis, Wegener's granulomatosis, and vasculitis secondary to connective tissue disorders like systemic lupus erythematosus (SLE), rheumatoid arthritis (RA), relapsing polychondritis, Behcet's disease, or other connective tissue disorders, vasculitis secondary to viral infection.

In another embodiment, a chronic inflammation comprises a skin disorder. Skin disorders include, without limitation, an acne, including acne vulgaris, a bullous phemigoid, a dermatitis, including atopic dermatitis and chronic actinic dermatitis, an eczema like atopic eczema, contact eczema, xerotic eczema, seborrhoeic dermatitis, dyshidrosis, discoid eczema, venous eczema, dermatitis herpetiformis, neurodermatitis, and autoeczematization, and statis dermatitis, hidradenitis suppurativa, lichen planus, psoriasis including plaqure psoriasis, nail psoriasis, guttate psoriasis, scalp psoriasis, inverse psoriasis, pustular psoriasis, erythrodermis psoriasis, and psoriatic arthritis, rosacea and scleroderma including morphea.

In another embodiment, a chronic inflammation comprises a gastrointestinal disorder. A gastrointestinal disorder includes, without limitation, irritable bowel disease, an inflammatory bowel disease including Crohn's disease and an ulcerative colitis like ulcerative proctitis, left-sided colitis, pancolitis and fulminant colitis.

In another embodiment, a chronic inflammation comprises a cardiovascular disease. When LDL cholesterol becomes embedded in arterial walls, it can invoke an immune response. Chronic inflammation eventually can damage the arteries, which can cause them to burst. Cardiovascular disease is any of a number of specific diseases that affect the heart itself and/or the blood vessel system, especially the veins and arteries leading to and from the heart. There are more than 60 types of cardiovascular disorders including, without limitation, a hypertension, endocarditis, myocarditis, heart valve dysfunction, congestive heart failure, myocardial infarction, a diabetic cardiac conditions, blood vessel inflammation like arteritis, phlebitis, vasculitis; arterial occlusive disease like arteriosclerosis and stenosis, inflammatory cardiomegaly, a peripheral arterial disease; an aneurysm; an embolism; a dissection; a pseudoaneurysm; a vascular malformation; a vascular nevus; a thrombosis; a thrombphlebitis; a varicose veins; a stroke. Symptoms of a cardiovascular disorder affecting the heart include, without limitation, chest pain or chest discomfort (angina), pain in one or both arms, the left shoulder, neck, jaw, or back, shortness of breath, dizziness, faster heartbeats, nausea, abnormal heartbeats, feeling fatigued. Symptoms of a cardiovascular disorder affecting the brain include, without limitation, sudden numbness or weakness of the face, arm, or leg, especially on one side of the body, sudden confusion or trouble speaking or understanding speech, sudden trouble seeing in one or both eyes, sudden dizziness, difficulty walking, or loss of balance or coordination, sudden severe headache with no known cause. Symptoms of a cardiovascular disorder affecting the legs, pelvis and/or arm include, without limitation, claudication, which is a pain, ache, or cramp in the muscles, and cold or numb feeling in the feet or toes, especially at night.

In another embodiment, a chronic inflammation comprises a cancer. Inflammation orchestrates the microenvironment around tumors, contributing to proliferation, survival and migration. For example, fibrinous inflammation results from a large increase in vascular permeability which allows fibrin to pass through the blood vessels. If an appropriate procoagulative stimulus is present, such as cancer cells, a fibrinous exudate is deposited. This is commonly seen in serous cavities, where the conversion of fibrinous exudate into a scar can occur between serous membranes, limiting their function. In another example, a cancer is an inflammatory cancer like a NF-κB-driven inflammatory cancer.

In another embodiment, a chronic inflammation comprises a pharmacologically-induced inflammation. Certain drugs or exogenic chemical compounds are known to affect inflammation. For example, Vitamin A deficiency causes an increase in an inflammatory response. Certain illicit drugs such as cocaine and ecstasy may exert some of their detrimental effects by activating transcription factors intimately involved with inflammation (e.g. NF-κB).

In another embodiment, a chronic inflammation comprises an infection. An infectious organism can escape the confines of the immediate tissue via the circulatory system or lymphatic system, where it may spread to other parts of the body. If an organism is not contained by the actions of acute inflammation it may gain access to the lymphatic system via nearby lymph vessels. An infection of the lymph vessels is known as lymphangitis, and infection of a lymph node is known as lymphadenitis. A pathogen can gain access to the bloodstream through lymphatic drainage into the circulatory system. Infections include, without limitation, bacterial cystitis, bacterial encephalitis, pandemic influenza, viral encephalitis, and viral hepatitis (A, B and C).

In another embodiment, a chronic inflammation comprises a tissue or organ injury. Tissue or organ injuries include, without limitation, a burn, a laceration, a wound, a puncture, or a trauma.

In another embodiment, a chronic inflammation comprises a transplant rejection. Transplant rejection occurs when a transplanted organ or tissue is not accepted by the body of the transplant recipient because the immune system of the recipient attacks the transplanted organ or tissue. An adaptive immune response, transplant rejection is mediated through both T cell mediated and humoral immune (antibodies) mechanisms. A transplant rejection can be classified as a hyperacute rejection, an acute rejection, or a chronic rejection. Chronic rejection of a transplanted organ or tissue is where the rejection is due to a poorly understood chronic inflammatory and immune response against the transplanted tissue. Also included in the term "transplant rejection" is a graft-versus-host disease (GVHD). GVHD is a common complication of allogeneic bone marrow transplantation in which functional immune cells in the transplanted marrow recognize the recipient as "foreign" and mount an immunologic attack. It can also take place in a blood transfusion under certain circumstances. GVHD is divided into acute and chronic forms. Acute and chronic GVHD appear to involve different immune cell subsets, different cytokine profiles, somewhat different host targets, and respond differently to treatment.

In another embodiment, a chronic inflammation comprises a Th1-mediated inflammatory disease. In a well-functioning immune system, an immune response should result in a well balanced pro-inflammatory Th1 response and anti-inflammatory Th2 response that is suited to address the immune challenge. Generally speaking, once a pro-inflammatory Th1 response is initiated, the body relies on the anti-inflammatory response invoked by a Th2 response to counteract this Th1 response. This counteractive response includes the release of Th2 type cytokines such as, e.g., IL-4, IL-5, and IL-13 which are associated with the promotion of IgE and eosinophilic responses in atopy, and also IL-10, which has an anti-inflammatory response. A Th1-mediated inflammatory disease involves an excessive pro-inflammatory response produced by Th1 cells that leads to chronic inflammation. The Th1-mediated disease may be virally, bacterially or chemically (e.g. environmentally) induced. For example, a virus causing the Th1-mediated disease may cause a chronic or acute infection, which may cause a respiratory disorder or influenza.

In another embodiment, a chronic inflammation comprises a chronic neurogenic inflammation. Chronic neurogenic Inflammation refers to an inflammatory response initiated and/or maintained through the release of inflammatory molecules like SP or CGRP which released from peripheral sensory nerve terminals (i.e., an efferent function, in contrast to the normal afferent signaling to the spinal cord in these nerves). Chronic neurogenic inflammation includes both primary inflammation and secondary neurogenic inflammation. As used herein, the term "primary" neurogenic inflammation refers to tissue inflammation (inflammatory symptoms) that is initiated by, or results from, the release of substances from primary sensory nerve terminals (such as C and A-delta fibers). As used herein, the term "secondary" neurogenic inflammation" refers to tissue inflammation initiated by non-neuronal sources (e.g., extravasation from vascular bed or tissue interstitium-derived, such as from mast cells or immune cells) of inflammatory mediators, such as peptides or cytokines, stimulating sensory nerve terminals and causing a release of inflammatory mediators from the nerves. The net effect of both forms (primary and secondary) of chronic neurogenic inflammation is to have an inflammatory state that is maintained by the sensitization of the peripheral sensory nerve fibers. The physiological consequence of the resulting chronic neurogenic inflammation depends on the tissue in question, producing, such as, e.g., cutaneous pain (allodynia, hyperalgesia), joint pain and/or arthritis, visceral pain and dysfunction, pulmonary dysfunction (asthma, COPD), and bladder dysfunction (pain, overactive bladder).

A composition or compound is administered to an individual. An individual is typically a human being. Typically, any individual who is a candidate for a conventional chronic inflammation treatment is a candidate for a chronic inflammation treatment disclosed herein. Pre-operative evaluation typically includes routine history and physical examination in addition to thorough informed consent disclosing all relevant risks and benefits of the procedure.

A pharmaceutical composition disclosed herein may comprise a therapeutic compound in a therapeutically effective amount. As used herein, the term "effective amount" is synonymous with "therapeutically effective amount", "effective dose", or "therapeutically effective dose" and when used in reference to treating a chronic inflammation refers to the minimum dose of a therapeutic compound disclosed herein necessary to achieve the desired therapeutic effect and includes a dose sufficient to reduce a symptom associated with a chronic inflammation. The effectiveness of a therapeutic compound disclosed herein in treating a chronic inflammation can be determined by observing an improvement in an individual based upon one or more clinical symptoms, and/or physiological indicators associated with the condition. An improvement in a chronic inflammation also can be indicated by a reduced need for a concurrent therapy.

The appropriate effective amount of a therapeutic compound disclosed herein to be administered to an individual for a particular chronic inflammation can be determined by a person of ordinary skill in the art by taking into account factors, including, without limitation, the type of chronic inflammation, the location of the chronic inflammation, the cause of the chronic inflammation, the severity of the chronic inflammation, the degree of relief desired, the duration of relief desired, the particular therapeutic compound used, the rate of excretion of the therapeutic compound used, the pharmacodynamics of the therapeutic compound used, the nature of the other compounds to be included in the composition, the particular route of administration, the particular characteristics, history and risk factors of the patient, such as, e.g., age, weight, general health and the like, or any combination thereof. Additionally, where repeated administration of a therapeutic compound is used, an effective amount of a therapeutic compound will further depend upon factors, including, without limitation, the frequency of administration, the half-life of the therapeutic compound, or any combination thereof. In is known by a person of ordinary skill in the art that an effective amount of a therapeutic compound disclosed herein can be extrapolated from in vitro assays and in vivo administration studies using animal models prior to administration to humans.

In aspects of this embodiment, a therapeutically effective amount of a therapeutic compound disclosed herein reduces a symptom associated with a chronic inflammation by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic compound disclosed herein reduces a symptom associated with a chronic inflammation by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic compound disclosed herein reduces a symptom associated with a chronic inflammation by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, a therapeutically effective amount of a therapeutic compound disclosed herein generally is in the range of about 0.001 mg/kg/day to about 100 mg/kg/day. In aspects of this embodiment, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

Dosing can be single dosage or cumulative (serial dosing), and can be readily determined by one skilled in the art. For instance, treatment of a chronic inflammation may comprise a one-time administration of an effective dose of a pharmaceutical composition disclosed herein. Alternatively, treatment of a chronic inflammation may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

In one embodiment, upon administration to an individual, a pharmaceutical composition comprising a therapeutic compound disclosed herein results in a bio-distribution of the therapeutic compound different than a bio-distribution of the therapeutic compound included in the same pharmaceutical composition, except without an adjuvant disclosed herein.

In another embodiment, upon administration to an individual, a therapeutic compound of the pharmaceutical composition disclosed herein is delivered to a macrophage. Macrophages are one of the key cell types believed to be involved in the control of the inflammation response. The resultant high level of a therapeutic compound having anti-inflammatory activity present in the macrophages results in a clinically effective treatment of chronic inflammation. In an aspect of this embodiment, upon administration to an individual, a therapeutically effective amount of a therapeutic compound of the pharmaceutical composition disclosed herein is preferentially delivered to a macrophage. In other aspect of this embodiment, upon administration to an individual, a therapeutic compound of the pharmaceutical composition disclosed herein is substantially delivered to a macrophage. In yet other aspect of this embodiment, upon administration to an individual, the amount of a therapeutic compound of the pharmaceutical composition disclosed herein delivered to a macrophage is, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the total amount of the therapeutic compound contained in the administered pharmaceutical composition. In still other aspects of this embodiment, upon administration to an individual, the amount of a therapeutic compound of the pharmaceutical composition disclosed herein delivered to a macrophage is in a range of, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70% of the total amount of the therapeutic compound contained in the administered pharmaceutical composition.

In another embodiment, upon administration to an individual, a pharmaceutical composition disclosed herein reduces gastric irritation. In an aspect of this embodiment, a pharmaceutical composition disclosed herein substantially reduces gastric irritation. In yet another embodiment, upon administration to an individual, a pharmaceutical composition disclosed herein reduces gastric irritation when compared to the same pharmaceutical composition disclosed herein, except without the pharmaceutically-acceptable adjuvant. In an aspect of this embodiment, a pharmaceutical composition disclosed herein substantially reduces gastric irritation when compared to the same pharmaceutical composition disclosed herein, except without the pharmaceutically-acceptable adjuvant. In other aspects of this embodiment, a pharmaceutical composition disclosed herein reduces gastric irritation by, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In yet other aspects of this embodiment, a pharmaceutical composition disclosed herein reduces gastric irritation in a range of, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70%.

In another embodiment, upon administration to an individual, a pharmaceutical composition disclosed herein reduces intestinal irritation. In an aspect of this embodiment, a pharmaceutical composition disclosed herein substantially reduces intestinal irritation. In yet another embodiment, upon administration to an individual, a pharmaceutical composition disclosed herein reduces intestinal irritation when compared to the same pharmaceutical composition disclosed herein, except without the pharmaceutically-acceptable adjuvant. In an aspect of this embodiment, a pharmaceutical composition disclosed herein substantially reduces intestinal irritation when compared to the same pharmaceutical composition disclosed herein, except without the pharmaceutically-acceptable adjuvant. In other aspects of this embodiment, a pharmaceutical composition disclosed herein reduces intestinal irritation by, e.g., at least 5%, at least 10%, at least 20%, at least 30%, at least 40%, at least 50%, at least 60%, at least 70%, at least 80%, at least 90%, or at least 100% when compared to the same pharmaceutical composition disclosed herein, except without the pharmaceutically-acceptable adjuvant. In yet other aspects of this embodiment, a pharmaceutical composition disclosed herein reduces intestinal irritation by, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70% when compared to the same pharmaceutical composition disclosed herein, except without the pharmaceutically-acceptable adjuvant.

A pharmaceutical composition disclosed herein can also be administered to an individual in combination with other therapeutic compounds to increase the overall therapeutic effect of the treatment. The use of multiple compounds to treat an indication can increase the beneficial effects while reducing the presence of side effects.

Aspects of the present invention can also be described as follows:

1. A pharmaceutical composition comprising: a) a therapeutic compound, wherein the therapeutic compound has an anti-inflammatory activity; and b) a pharmaceutically-acceptable adjuvant.
2. The pharmaceutical composition according to embodiment 1, wherein the composition further comprises a pharmaceutically-acceptable solvent.
3. A pharmaceutical composition comprising: a) a therapeutic compound, wherein the therapeutic compound has an anti-inflammatory activity; b) a pharmaceutically-acceptable solvent; and c) a pharmaceutically-acceptable adjuvant.
4. A pharmaceutical composition comprising: a) a therapeutic compound, wherein the therapeutic compound has an anti-inflammatory activity; b) a pharmaceutically-acceptable solvent; and c) a pharmaceutically-acceptable adjuvant, wherein the ratio of the pharmaceutically-acceptable solvent to pharmaceutically-acceptable adjuvant is in a range from about 0:1 to about 1:25.
5. The pharmaceutical composition according to embodiment 2 or 3, wherein the ratio of the pharmaceutically-acceptable solvent to pharmaceutically-acceptable adjuvant is in a range from about 0:1 to about 1:25.
6. The pharmaceutical composition according to embodiments 1-5, wherein the anti-inflammatory activity reduces the level of an inflammation inducing molecule.
7. The pharmaceutical composition according to embodiment 6, wherein the inflammation inducing molecule comprises substance P (SP), calcitonin gene-related peptide (CGRP), glutamate, or a combination thereof.

8. The pharmaceutical composition according to embodiment 7, wherein the anti-inflammatory activity reduces the level of SP, CGRP, glutamate, or a combination thereof by at least 10%.
9. The pharmaceutical composition according to embodiments 1-8, wherein the anti-inflammatory activity reduces the level of an inflammation inducing prostaglandin.
10. The pharmaceutical composition according to embodiment 9, wherein the level of the inflammation inducing prostaglandin is reduced by at least 10%.
11. The pharmaceutical composition according to embodiments 1-10, wherein the anti-inflammatory activity stimulates a PPAR signaling pathway.
12. The pharmaceutical composition according to embodiment 11, wherein the PPAR signaling pathway is stimulated by at least 10%.
13. The pharmaceutical composition according to embodiments 1-12, wherein the anti-inflammatory activity induces apoptosis of Macrophage M1 cells, promotes differentiation of Macrophage M2 cells, or both.
14. The pharmaceutical composition according to embodiments 1-13, wherein the anti-inflammatory activity reducing the levels of Interferon-gamma (IFNγ), Tumor necrosis factor-alpha (TNF-α), Interleukin-12 (IL-12), or a combination thereof released from Th1 cells, increases the levels of IL-10 released from a Th2 cell, or both.
15. The pharmaceutical composition according to embodiment 14, wherein the levels of IFNγ, TNF-α, IL-12, or a combination thereof released from a Th1 cell are reduced by at least 10%.
16. The pharmaceutical composition according to embodiment 14, wherein the levels of IL-10 released from a Th2 cell are increased by at least 10%.
17. The pharmaceutical composition according to embodiments 1-16, wherein the therapeutic compound has a log P value indicating that the compound is soluble in an organic solvent.
18. The pharmaceutical composition according to embodiments 1-17, wherein the therapeutic compound has a log P value of more than 1.0.
19. The pharmaceutical composition according to embodiments 1-17, wherein the therapeutic compound has a log P value of more than 2.0.
20. The pharmaceutical composition according to embodiments 1-19, wherein the therapeutic compound has a polar surface area that is hydrophobic.
21. The pharmaceutical composition according to embodiments 1-20, wherein the therapeutic compound has a polar surface area that is less than 8.0 nm$^2$.
22. The pharmaceutical composition according to embodiments 1-20, wherein the therapeutic compound has a polar surface area that is less than 6.0 nm$^2$.
23. The pharmaceutical composition according to embodiments 1-22, wherein the therapeutic compound comprises a non-steroidal anti-inflammatory drug (NSAID).
24. The pharmaceutical composition according to embodiment 23, wherein the NSAID comprises a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor or a combination thereof.
25. The pharmaceutical composition according to embodiments 1-24, wherein the therapeutic compound comprises a PPARγ agonist.
26. The pharmaceutical composition according to embodiment 25, wherein the PPARγ agonist comprises Monascin, Irbesartan, Telmisartan, mycophenolic acid, Resveratrol, Delta(9)-tetrahydrocannabinol, a cannabidiol, Curcumin, Cilostazol, Benzbromarone, 6-shogaol, glycyrrhetinic acid, a thiazolidinedione, a NSAID, a fibrate, or a combination thereof.
27. The pharmaceutical composition according to embodiments 1-26, wherein the therapeutic compound comprises a nuclear receptor binding agent.
28. The pharmaceutical composition according to embodiment 27, wherein the nuclear receptor binding agent comprises a Retinoic Acid Receptor (RAR) binding agent, a Retinoid X Receptor (RXR) binding agent, a Liver X Receptor (LXR) binding agent, a Vitamin D binding agent, or a combination thereof.
29. The pharmaceutical composition according to embodiments 1-28, wherein the therapeutic compound comprises an anti-hyperlipidemic agent.
30. The pharmaceutical composition according to embodiment 29, wherein the anti-hyperlipidemic agent comprises a fibrate, a statin, a tocotrienol, a niacin, a bile acid sequestrants (resin), a cholesterol absorption inhibitor, a pancreatic lipase inhibitor, a sympathomimetic amine, or a combination thereof.
31. The pharmaceutical composition according to embodiment 29, wherein the fibrate comprises Bezafibrate, Ciprofibrate, Clofibrate, Gemfibrozil, Fenofibrate, or a combination thereof.
32. The pharmaceutical composition according to embodiment 29, wherein the statin comprises Atorvastatin, Fluvastatin, Lovastatin, Pitavastatin, Pravastatin, Rosuvastatin, Simvastatin, or a combination thereof.
33. The pharmaceutical composition according to embodiment 29, wherein the niacin comprises acipimox, niacin, nicotinamide, vitamin B3, or a combination thereof.
34. The pharmaceutical composition according to embodiment 29, wherein the bile acid sequestrant comprises Cholestyramine, Colesevelam, Colestipol, or a combination thereof.
35. The pharmaceutical composition according to embodiment 29, wherein the cholesterol absorption inhibitor comprises Ezetimibe, a phytosterol, a sterol, a stanol, or a combination thereof.
36. The pharmaceutical composition according to embodiment 29, wherein the fat absorption inhibitor comprises Orlistat
37. The pharmaceutical composition according to embodiment 29, wherein the sympathomimetic amine comprises Clenbuterol, Salbutamol, ephedrine, pseudoephedrine, methamphetamine, amphetamine, phenylephrine, isoproterenol, dobutamine, methylphenidate, lisdexamfetamine, cathine, cathinone, methcathinone, cocaine, benzylpiperazine (BZP), methylenedioxypyrovalerone (MDPV), 4-methylaminorex, pemoline, phenmetrazine, propylhexedrine, or a combination thereof.
38. The pharmaceutical composition according to embodiments 1-37, wherein the therapeutic compound comprises an ester of a therapeutic compound.
39. The pharmaceutical composition according to embodiments 1-38, wherein the therapeutic compound comprises an ester of a therapeutic compound according to embodiments 23-37.
40. The pharmaceutical composition according to embodiments 1-39, wherein the pharmaceutically-acceptable solvent is less than about 20% (v/v).

41. The pharmaceutical composition according to embodiments 1-40, wherein the pharmaceutically-acceptable solvent comprises a pharmaceutically-acceptable polar aprotic solvent, a pharmaceutically-acceptable polar protic solvent, a pharmaceutically-acceptable non-polar solvent, or a combination thereof.

42. The pharmaceutical composition according to embodiments 1-41, wherein the pharmaceutically-acceptable solvent comprises a pharmaceutically-acceptable alcohol.

43. The pharmaceutical composition according to embodiment 42, wherein the pharmaceutically-acceptable alcohol comprises an acyclic alcohol, a monohydric alcohol, a polyhydric alcohol, an unsaturated aliphatic alcohol, an alicyclic alcohol, or a combination thereof.

44. The pharmaceutical composition according to embodiment 42, wherein the pharmaceutically-acceptable alcohol comprises a $C_{1-20}$ alcohol.

45. The pharmaceutical composition according to embodiment 42, wherein the pharmaceutically-acceptable alcohol comprises methanol, ethanol, propanol, butanol, pentanol, 1-hexadecanol, or a combination thereof.

46. The pharmaceutical composition according to embodiments 1-45, wherein the pharmaceutically-acceptable solvent comprises a pharmaceutically-acceptable ester of pharmaceutically-acceptable alcohol and an acid.

47. The pharmaceutical composition according to embodiment 46, wherein the pharmaceutically-acceptable ester comprises methyl acetate, methyl buterate, methyl formate, ethyl acetate, ethyl buterate, ethyl formate, propyl acetate, propyl buterate, propyl formate, butyl acetate, butyl buterate, butyl formate, isobutyl acetate, isobutyl buterate, isobutyl formate, pentyl acetate, pentyl buterate, pentyl formate, and 1-hexadecyl acetate, 1-hexadecyl buterate, and 1-hexadecyl formate, or a combination thereof.

48. The pharmaceutical composition according to embodiments 1-47, wherein the pharmaceutically-acceptable solvent comprises a pharmaceutically-acceptable polyethylene glycol (PEG) polymer.

49. The pharmaceutical composition according to embodiment 48, wherein the pharmaceutically-acceptable polyethylene glycol (PEG) polymer is less than about 2,000 g/mol.

50. The pharmaceutical composition according to embodiment 48, wherein the pharmaceutically-acceptable polyethylene glycol (PEG) polymer is more than about 2,000 g/mol.

51. The pharmaceutical composition according to embodiments 1-50, wherein the pharmaceutically-acceptable solvent comprises a pharmaceutically-acceptable glyceride.

52. The pharmaceutical composition according to embodiment 51, wherein the pharmaceutically-acceptable glyceride comprises a monoglyceride, a diglyceride, a triglyceride, an acetylated monoglyceride, an acetylated diglyceride, an acetylated triglyceride, or a combination thereof.

53. The pharmaceutical composition according to embodiments 1-52, wherein the pharmaceutically-acceptable solvent is a liquid at 20° C.

54. The pharmaceutical composition according to embodiments 1-52, wherein the pharmaceutically-acceptable solvent is a solid at 20° C.

55. The pharmaceutical composition according to embodiment 54, wherein the pharmaceutically-acceptable solid solvent comprises menthol.

56. The pharmaceutical composition according to embodiments 1-55, wherein the adjuvant is at least 80% (v/v).

57. The pharmaceutical composition according to embodiments 1-56, wherein the pharmaceutically-acceptable adjuvant is a liquid at 20° C.

58. The pharmaceutical composition according to embodiments 1-56, wherein the pharmaceutically-acceptable adjuvant is a solid at 20° C.

59. The pharmaceutical composition according to embodiments 1-58, wherein the pharmaceutically-acceptable adjuvant comprises a pharmaceutically-acceptable lipid.

60. The pharmaceutical composition according to embodiment 59, wherein the pharmaceutically-acceptable lipid comprises a saturated fatty acid, an unsaturated fatty acid, or a combination thereof.

61. The pharmaceutical composition according to embodiment 59 or 60, wherein the pharmaceutically-acceptable lipid comprises two or more saturated or unsaturated fatty acids.

62. The pharmaceutical composition according to embodiment 61, wherein the two or more saturated or unsaturated fatty acids includes palmitic acid, stearic acid, oleic acid, linoleic acid, linolenic acid, or a combination thereof.

63. The pharmaceutical composition according to embodiments 60-62, wherein the unsaturated fatty acid has a melting point temperature of 20° C. or below.

64. The pharmaceutical composition according to embodiments 60-62, wherein the unsaturated fatty acid is a solid at 20° C.

65. The pharmaceutical composition according to embodiments 60-62, wherein the unsaturated fatty acid comprises an omega fatty acid.

66. The pharmaceutical composition according to embodiment 59, wherein the pharmaceutically-acceptable lipid comprises a pharmaceutically-acceptable oil.

67. The pharmaceutical composition according to embodiment 66, wherein the pharmaceutically-acceptable oil comprises almond oil, arachis oil, avocado oil, canola oil, castor oil, coconut oil, corn oil, cottonseed oil, grape seed oil, hazelnut oil, hemp oil, linseed oil, olive oil, palm oil, peanut oil, rapeseed oil, rice bran oil, safflower oil, sesame oil, soybean oil, soya oil, sunflower oil, walnut oil, wheat germ oil, or a combination thereof.

68. The pharmaceutical composition according to embodiments 1-67, wherein the pharmaceutical composition further comprises a pharmaceutically-acceptable stabilizing agent.

69. The pharmaceutical composition according to embodiment 68, wherein the pharmaceutically-acceptable stabilizing agent comprises water, a sacrificial acid comprising a fatty acid component and acetic acid, ethyl acetate, a sodium acetate/acetic acid, a monoglyceride, an acetylated monoglyceride, a diglyceride, an acetylated diglyceride, a fatty acid, a fatty acid salt, or a combination thereof.

70. The pharmaceutical composition according to embodiment 68, wherein the pharmaceutically-acceptable stabilizing agent comprises a pharmaceutically-acceptable emulsifying agent.

71. The pharmaceutical composition according to embodiment 70, wherein the pharmaceutically-acceptable emulsifying agent comprises a surfactant, a polysaccharide, a lectin, a phospholipid, or a combination thereof.

72. The pharmaceutical composition according to embodiments 1-69, wherein the pharmaceutical composition does not comprise a pharmaceutically-acceptable emulsifying agent. 73. A method of preparing a pharmaceutical composition, the method comprising the step of contacting a therapeutic compound with a pharmaceutically-acceptable adjuvant under conditions which allow the formation of the pharmaceutical composition.

74. A method of preparing a pharmaceutical composition, the method comprising the steps: a) contacting a pharmaceutically-acceptable solvent with a therapeutic compound under conditions which allow the therapeutic compound to dissolve in the pharmaceutically-acceptable solvent, thereby forming a solution, wherein the therapeutic compound has anti-inflammatory activity, and b) contacting the solution formed in step (a) with a pharmaceutically-acceptable adjuvant under conditions which allow the formation of the pharmaceutical composition.

75. A method of preparing a pharmaceutical composition, the method comprising the steps: a) contacting a pharmaceutically-acceptable solvent with a therapeutic compound under conditions which allow the therapeutic compound to dissolve in the pharmaceutically-acceptable solvent, thereby forming a solution, wherein the therapeutic compound has anti-inflammatory activity, and b) contacting the solution formed in step (a) with a pharmaceutically-acceptable adjuvant under conditions which allow the formation of the pharmaceutical composition, wherein the ratio of the pharmaceutically-acceptable solvent to pharmaceutically-acceptable adjuvant is in a range from about 0:1 to about 1:25.

76. The method according to embodiments 73-75, wherein the therapeutic compound has a log P value indicating that the compound is soluble in an organic solvent.

77. The method according to embodiment 73-76, wherein the therapeutic compound has a log P value of more than 1.0.

78. The method according to embodiment 73-76, wherein the therapeutic compound has a log P value of more than 2.0.

79. The method according to embodiments 73-78, wherein the therapeutic compound has a polar surface area that is hydrophobic.

80. The method according to embodiments 73-79, wherein the therapeutic compound has a polar surface area that is less than 8.0 nm$^2$.

81. The method according to embodiments 73-79, wherein the therapeutic compound has a polar surface area that is less than 6.0 nm$^2$.

82. The method according to embodiments 73-81, wherein the therapeutic compound comprises a non-steroidal anti-inflammatory drug (NSAID).

83. The method according to embodiment 82, wherein the NSAID comprises a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a combination thereof.

84. The method according to embodiments 73-83, wherein the therapeutic compound comprises a PPARγ agonist.

85. The method according to embodiment 84, wherein the PPARγ agonist comprises Monascin, Irbesartan, Telmisartan, mycophenolic acid, Resveratrol, Delta(9)-tetrahydrocannabinol, a cannabidiol, Curcumin, Cilostazol, Benzbromarone, 6-shogaol, glycyrrhetinic acid, a thiazolidinedione, a NSAID, a fibrate, or a combination thereof.

86. The method according to embodiments 73-85, wherein the therapeutic compound comprises a nuclear receptor binding agent.

87. The method according to embodiment 86, wherein the nuclear receptor binding agent comprises a Retinoic Acid Receptor (RAR) binding agent, a Retinoid X Receptor (RXR) binding agent, a Liver X Receptor (LXR) binding agent, a Vitamin D binding agent, or a combination thereof.

88. The method according to embodiments 73-87, wherein the therapeutic compound comprises an anti-hyperlipidemic agent.

89. The method according to embodiment 88, wherein the anti-hyperlipidemic agent comprises a fibrate, a statin, a tocotrienol, a niacin, a bile acid sequestrants (resin), a cholesterol absorption inhibitor, a pancreatic lipase inhibitor, a sympathomimetic amine, or a combination thereof.

90. The method according to embodiment 89, wherein the fibrate comprises Bezafibrate, Ciprofibrate, Clofibrate, Gemfibrozil, Fenofibrate, or a combination thereof.

91. The method according to embodiment 89, wherein the statin comprises Atorvastatin, Fluvastatin, Lovastatin, Pitavastatin, Pravastatin, Rosuvastatin, Simvastatin, or a combination thereof.

92. The method according to embodiment 89, wherein the niacin comprises acipimox, niacin, nicotinamide, vitamin B3, or a combination thereof.

93. The method according to embodiment 89, wherein the bile acid sequestrant comprises Cholestyramine, Colesevelam, Colestipol, or a combination thereof. 94. The method according to embodiment 89, wherein the cholesterol absorption inhibitor comprises Ezetimibe, a phytosterol, a sterol, a stanol, or a combination thereof.

95. The method according to embodiment 89, wherein the fat absorption inhibitor comprises Orlistat 96. The method according to embodiment 89, wherein the sympathomimetic amine comprises Clenbuterol, Salbutamol, ephedrine, pseudoephedrine, methamphetamine, amphetamine, phenylephrine, isoproterenol, dobutamine, methylphenidate, lisdexamfetamine, cathine, cathinone, methcathinone, cocaine, benzylpiperazine (BZP), methylenedioxypyrovalerone (MDPV), 4-methylaminorex, pemoline, phenmetrazine, propylhexedrine, or a combination thereof.

97. The method according to embodiments 73-96, wherein the therapeutic compound comprises an ester of a therapeutic compound.

98. The method according to embodiments 73-97, wherein the therapeutic compound comprises an ester of a therapeutic compound according to embodiments 76-97.

99. The method according to embodiments 74-98, wherein the pharmaceutically-acceptable solvent is less than about 20% (v/v).

100. The method according to embodiments 74-99, wherein the pharmaceutically-acceptable solvent comprises a pharmaceutically-acceptable polar aprotic solvent, a pharmaceutically-acceptable polar protic solvent, a pharmaceutically-acceptable non-polar solvent, or a combination thereof.

101. The method according to embodiments 74-100, wherein the pharmaceutically-acceptable solvent comprises a pharmaceutically-acceptable alcohol.

102. The method according to embodiment 101, wherein the pharmaceutically-acceptable alcohol comprises an acyclic alcohol, a monohydric alcohol, a polyhydric alcohol, an unsaturated aliphatic alcohol, an alicyclic alcohol, or a combination thereof.

103. The method according to embodiment 101, wherein the pharmaceutically-acceptable alcohol comprises a $C_{1-20}$ alcohol.

104. The method according to embodiment 101, wherein the pharmaceutically-acceptable alcohol comprises methanol, ethanol, propanol, butanol, pentanol, 1-hexadecanol, or a combination thereof.

105. The method according to embodiment 101, wherein the pharmaceutically-acceptable solvent comprises a pharmaceutically-acceptable ester of pharmaceutically-acceptable alcohol and an acid.

106. The method according to embodiment 105, wherein the pharmaceutically-acceptable ester comprises methyl acetate, methyl buterate, methyl formate, ethyl acetate, ethyl buterate, ethyl formate, propyl acetate, propyl buterate, propyl formate, butyl acetate, butyl buterate, butyl formate, isobutyl acetate, isobutyl buterate, isobutyl formate, pentyl acetate, pentyl buterate, pentyl formate, and 1-hexadecyl acetate, 1-hexadecyl buterate, and 1-hexadecyl formate, or a combination thereof.

107. The method according to embodiments 74-106, wherein the pharmaceutically-acceptable solvent is a pharmaceutically-acceptable polyethylene glycol (PEG) polymer.

108. The method according to embodiment 107, wherein the pharmaceutically-acceptable polyethylene glycol (PEG) polymer is less than about 2,000 g/mol.

109. The method according to embodiment 107, wherein the pharmaceutically-acceptable polyethylene glycol (PEG) polymer is more than about 2,000 g/mol.

110. The method according to embodiments 74-109, wherein the pharmaceutically-acceptable solvent comprises a pharmaceutically-acceptable glyceride.

111. The method according to embodiments 110, wherein the pharmaceutically-acceptable glyceride is a monoglyceride, a diglyceride, a triglyceride, an acetylated monoglyceride, an acetylated diglyceride, an acetylated triglyceride, or a combination thereof.

112. The method according to embodiments 74-111, wherein the pharmaceutically-acceptable solvent is a liquid at 20° C.

113. The method according to embodiments 74-111, wherein the pharmaceutically-acceptable solvent is a solid at 20° C.

114. The method according to embodiment 113, wherein the pharmaceutically-acceptable solid solvent is menthol.

115. The method according to embodiments 73-114, wherein the pharmaceutically-acceptable adjuvant is at least 80% (v/v).

116. The method according to embodiments 73-115, wherein the pharmaceutically-acceptable adjuvant is a liquid at 20° C.

117. The method according to embodiments 73-115, wherein the pharmaceutically-acceptable adjuvant is a solid at 20° C.

118. The method according to embodiments 73-117, wherein the pharmaceutically-acceptable adjuvant comprises a pharmaceutically-acceptable lipid.

119. The method according to embodiment 118, wherein the pharmaceutically-acceptable lipid comprises a pharmaceutically-acceptable saturated fatty acid, an unsaturated fatty acid, or a combination thereof.

120. The method according to embodiment 118 or 119, wherein the pharmaceutically-acceptable lipid comprises two or more pharmaceutically-acceptable saturated or unsaturated fatty acids.

121. The method according to embodiments 120, wherein the two or more pharmaceutically-acceptable saturated or unsaturated fatty acids include palmitic acid, stearic acid, oleic acid, linoleic acid, linolenic acid, or a combination thereof.

122. The method according to embodiments 119-121, wherein the pharmaceutically-acceptable unsaturated fatty acid has a melting point temperature of 20° C. or below.

123. The method according to embodiments 119-121, wherein the pharmaceutically-acceptable unsaturated fatty acid is a solid at 20° C.

124. The method according to embodiments 119-123, wherein the pharmaceutically-acceptable unsaturated fatty acid comprises an omega fatty acid.

125. The method according to embodiments 118-124, wherein the pharmaceutically-acceptable lipid comprises a pharmaceutically-acceptable oil.

126. The method according to embodiment 125, wherein the pharmaceutically-acceptable oil comprises almond oil, arachis oil, avocado oil, canola oil, castor oil, coconut oil, corn oil, cottonseed oil, grape seed oil, hazelnut oil, hemp oil, linseed oil, olive oil, palm oil, peanut oil, rapeseed oil, rice bran oil, safflower oil, sesame oil, soybean oil, soya oil, sunflower oil, walnut oil, wheat germ oil, or a combination thereof.

127. The method according to embodiments 74 or 76-126, wherein in step(b) the ratio of the pharmaceutically-acceptable solvent to pharmaceutically-acceptable adjuvant is in a range from about 0:1 to about 1:25.

128. The method according to embodiments 73-127, wherein the step (a) further comprising contacting a pharmaceutically-acceptable stabilizing agent with the pharmaceutically-acceptable solvent and the therapeutic compound.

129. The method according to embodiment 128, wherein the pharmaceutically-acceptable stabilizing agent comprises water, a sacrificial acid comprising a fatty acid component and acetic acid, ethyl acetate, a sodium acetate/acetic acid, a monoglyceride, an acetylated monoglyceride, a diglyceride, an acetylated diglyceride, a fatty acid, a fatty acid salt, or a combination thereof.

130. The method according to embodiment 128 or 129, wherein the pharmaceutically-acceptable stabilizing agent comprises a pharmaceutically-acceptable emulsifying agent.

131. The method according to embodiment 130, wherein the pharmaceutically-acceptable emulsifying agent comprises a surfactant, a polysaccharide, a lectin, a phospholipid, or a combination thereof.

132. The method according to embodiments 73-129, wherein the pharmaceutical composition does not comprise a pharmaceutically-acceptable emulsifying agent.

133. The method according to embodiments 74-132, wherein the method further comprises removing the pharmaceutically-acceptable solvent from the pharmaceutical composition.

134. The method according to embodiment 133, wherein at least 5% the pharmaceutically-acceptable solvent is removed from the pharmaceutical composition.

135. The method according to embodiment 133 or 134, wherein at, removal of solvent from the pharmaceutical composition disclosed herein is carried out at a temperature of less than 20° C.

136. The method according to embodiments 73-135, wherein the pharmaceutical composition made is according to embodiments 1-72.

137. A method of treating an individual with a chronic inflammation, the method comprising the step of: administering to the individual in need thereof a pharmaceutical composition according to embodiments 1-72, wherein administration results in a reduction in a symptom associated with the chronic inflammation, thereby treating the individual.

138. Use of a pharmaceutical composition according to embodiments 1-72 in the manufacture of a medicament for the treatment of a chronic inflammation.

139. Use of a pharmaceutical composition according to embodiments 1-72 for the treatment of a chronic inflammation.

140. The method according to embodiment 137 or the use according to embodiment 138 or 139, wherein the chronic inflammation is associated with acne, acid reflux/heartburn, age related macular degeneration (AMD), allergy, allergic rhinitis, Alzheimer's disease, amyotrophic lateral sclerosis, anemia, appendicitis, arteritis, arthritis, asthma. atherosclerosis, autoimmune disorders, balanitis, blepharitis, bronchiolitis, bronchitis, a bullous pemphigoid, burn, bursitis, cancer, cardiac arrest, carditis, celiac disease, cellulitis, cervicitis, cholangitis, cholecystitis, chorioamnionitis, chronic obstructive pulmonary disease (COPD), cirrhosis, colitis, congestive heart failure, conjunctivitis, cyclophosphamide-induced cystitis, cystic fibrosis, cystitis, common cold, dacryoadenitis, dementia, dermatitis, dermatomyositis, diabetes, diabetic neuropathy, diabetic retinopathy, diabetic nephropathy, diabetic ulcer, digestive system disease, eczema, emphysema, encephalitis, endocarditis, endometritis, enteritis, enterocolitis, epicondylitis, epididymitis, fasciitis, fibromyalgia, fibrosis, fibrositis, gastritis, gastroenteritis, gingivitis, glomerulonephritis, glossitis, heart disease, heart valve dysfunction, hepatitis, hidradenitis suppurativa, Huntington's disease, hyperlipidemic pancreatitis, hypertension, ileitis, infection, inflammatory bowel disease, inflammatory cardiomegaly, inflammatory neuropathy, insulin resistance, interstitial cystitis, interstitial nephritis, iritis, ischemia, ischemic heart disease, keratitis, keratoconjunctivitis, laryngitis, lupus nephritis, mastitis, mastoiditis, meningitis, metabolic syndrome (syndrome X), a migraine, multiple sclerosis, myelitis, myocarditis, myositis, nephritis, non-alcoholic steatohepatitis, obesity, omphalitis, oophoritis, orchitis, osteochondritis, osteopenia, osteomyelitis, osteoporosis, osteitis, otitis, pancreatitis, Parkinson's disease, parotitis, pelvic inflammatory disease, pemphigus vularis, pericarditis, peritonitis, pharyngitis, phlebitis, pleuritis, pneumonitis, polycystic nephritis, proctitis, prostatitis, psoriasis, pulpitis, pyelonephritis, pylephlebitis, renal failure, reperfusion injury, retinitis, rheumatic fever, rhinitis, salpingitis, sarcoidosis, sialadenitis, sinusitis, spastic colon, stenosis, stomatitis, stroke, surgical complication, synovitis, tendonitis, tendinosis, tenosynovitis, thrombophlebitis, tonsillitis, trauma, traumatic brain injury, transplant rejection, trigonitis, tuberculosis, tumor, urethritis, ursitis, uveitis, vaginitis, vasculitis, or vulvitis.

141. The method according to embodiment 137 or the use according to embodiment 138 or 139, wherein the chronic inflammation is a tissue inflammation.

142. The method according to embodiment 137 or the use according to embodiment 138 or 139, wherein the chronic inflammation is a systemic inflammation.

143. The method according to embodiment 137 or the use according to embodiment 138 or 139, wherein the chronic inflammation is an arthritis.

144. The method or use according to embodiment 140 or 143, wherein the arthritis is a monoarthritis, an oligoarthritis, or a polyarthritis.

145. The method or use according to embodiment 140 or 143, wherein the arthritis is an auto-immune disease or a non-autoimmune disease.

146. The method or use according to embodiment 140 or 143, wherein the arthritis is an osteoarthritis, a rheumatoid arthritis, a juvenile idiopathic arthritis, a septic arthritis, a spondyloarthropathy, a gout, a pseudogout, or Still's disease.

147. The method or use according to embodiment 146, wherein the spondyloarthropathy is an ankylosing spondylitis, a reactive arthritis (Reiter's syndrome), a psoriatic arthritis, an enteropathic arthritis associated with inflammatory bowel disease, a Whipple disease or a Behcet disease.

148. The method according to embodiment 137 or the use according to embodiment 138 or 139, wherein the chronic inflammation is an autoimmune disorder.

149. The method or use according to embodiment 140 or 148, wherein the autoimmune disorder is a systemic autoimmune disorder or an organ-specific autoimmune disorder.

150. The method or use according to embodiment 140 or 148, wherein the autoimmune disorder is an acute disseminated encephalomyelitis (ADEM), an Addison's disease, an allergy, an anti-phospholipid antibody syndrome (APS), an autoimmune hemolytic anemia, an autoimmune hepatitis, an autoimmune inner ear disease, a bullous pemphigoid, a celiac disease, a Chagas disease, a chronic obstructive pulmonary disease (COPD), a diabetes mellitus type 1 (IDDM), an endometriosis, a Goodpasture's syndrome, a Graves' disease, a Guillain-Barre syndrome (GBS), a Hashimoto's thyroiditis, a hidradenitis suppurativa, an idiopathic thrombocytopenic purpura, an inflammatory bowel disease, an interstitial cystitis, a lupus (including a discoid lupus erythematosus, a drug-induced lupus erythematosus. a lupus nephritis, a neonatal lupus, a subacute cutaneous lupus erythematosus, a systemic lupus erythematosus, a morphea, a multiple sclerosis (MS), a myasthenia gravis, a myopathy, a narcolepsy, a neuromyotonia, a pemphigus vulgaris, a pernicious anaemia, a primary biliary cirrhosis, a recurrent disseminated encephalomyelitis, a rheumatic fever, a schizophrenia, a scleroderma, a Sjögren's syndrome, a tenosynovitis, a vasculitis, or a vitiligo.

151. The method according to embodiment 137 or the use according to embodiment 138 or 139, wherein the chronic inflammation is a myopathy.

152. The method or use according to embodiment 137 or 148, wherein the myopathy is a dermatomyositis, an inclusion body myositis, or a polymyositis.

153. The method according to embodiment 137 or the use according to embodiment 138 or 139, wherein the chronic inflammation is a vasculitis.

154. The method or use according to embodiment 140 or 153, wherein the vasculitis is vasculitis is a Buerger's disease, an arteritis, a cerebral vasculitis, a Churg-Strauss arteritis, a cryoglobulinemia, an essential cryoglobulinemic vasculitis, a giant cell arteritis, a Golfers vasculitis, a Henoch-Schonlein purpura, a hypersensitivity vasculitis, a Kawasaki disease, a phlebitis, a microscopic polyarteritis/polyangiitis, a polyarteritis nodosa, a polymyalgia rheumatica (PMR), a rheumatoid vasculitis, a Takayasu arteritis, a thrombophlebitis, a Wegener's granulomatosis, or a vasculitis secondary to connective tissue disorder, or vasculitis secondary to viral infection.
155. The method according to embodiment 137 or the use according to embodiment 138 or 139, wherein the chronic inflammation is associated with a skin disorder.
156. The method or use according to embodiment 140 or 155, wherein the skin disorder is a dermatitis, an eczema, a statis dermatitis, a hidradenitis suppurativa, a psoriasis, a rosacea or a scleroderma.
157. The method or use according to embodiment 156, wherein the eczema is an atopic eczema, a contact eczema, a xerotic eczema, a seborrhoeic dermatitis, a dyshidrosis, a discoid eczema, a venous eczema, a dermatitis herpetiformis, a neurodermatitis, or an autoeczematization.
158. The method or use according to embodiment 156, wherein the psoriasis is a plaqure psoriasis, a nail psoriasis, a guttate psoriasis, a scalp psoriasis, an inverse psoriasis, a pustular psoriasis, or an erythrodermis psoriasis.
159. The method according to embodiment 137 or the use according to embodiment 138 or 139, wherein the chronic inflammation is associated with a gastrointestinal disorder.
160. The method or use according to embodiment 140 or 159, wherein the gastrointestinal disorder is an irritable bowel disease or an inflammatory bowel.
161. The method or use according to embodiment 160, wherein the inflammatory bowel is a Crohn's disease or an ulcerative colitis.
162. The method according to embodiment 137 or the use according to embodiment 138 or 139, wherein the chronic inflammation is associated with a cardiovascular disease.
163. The method or use according to embodiment 140 or 162, wherein the cardiovascular disease is a hypertension, heart valve dysfunction, congestive heart failure, myocardial infarction, a diabetic cardiac conditions, a blood vessel inflammation, arterial occlusive disease, a peripheral arterial disease, an aneurysm, an embolism, a dissection, a pseudoaneurysm, a vascular malformation, a vascular nevus, a thrombosis, a thrombphlebitis, a varicose veins, or a stroke.
164. The method according to embodiment 137 or the use according to embodiment 138 or 139, wherein the chronic inflammation is associated with a cancer.
165. The method according to embodiment 137 or the use according to embodiment 138 or 139, wherein the chronic inflammation is associated with a pharmacologically-induced inflammation.
166. The method according to embodiment 137 or the use according to embodiment 138 or 139, wherein the chronic inflammation is associated with an infection.
167. The method or use according to embodiment 140 or 166, wherein the infection is a bacterial cystitis, a bacterial encephalitis, a pandemic influenza, a viral encephalitis, a viral hepatitis A, a viral hepatitis B, or a viral hepatitis C.
168. The method according to embodiment 137 or the use according to embodiment 138 or 139, wherein the chronic inflammation is associated with a tissue or organ injury.
169. The method according to embodiment 137 or the use according to embodiment 138 or 139, wherein the chronic inflammation is associated with a transplant rejection or a graft-versus-host disease.
170. The method according to embodiment 137 or the use according to embodiment 138 or 139, wherein the chronic inflammation is associated with a Th1-mediated inflammatory disease.
171. The method according to embodiment 137 or the use according to embodiment 138 or 139, wherein the chronic inflammation is associated with chronic neurogenic inflammation.
172. The method according to embodiments 137 or 140-171 or the use according to embodiments 138-171, wherein upon administration to an individual, the pharmaceutical composition comprising the therapeutic compound according to embodiments 1-72 results in a bio-distribution of the therapeutic compound different than a bio-distribution of the therapeutic compound included in the same pharmaceutical composition, except without the pharmaceutically-acceptable adjuvant.
173. The method according to embodiments 137 or 140-172 or the use according to embodiments 138-172, wherein upon administration to an individual, the amount of the therapeutic compound of the pharmaceutical composition according to embodiments 1-72 delivered to a macrophage is at least 5% of the total amount of the therapeutic compound contained in the administered pharmaceutical composition.
174. The method according to embodiments 137 or 140-173 or the use according to embodiments 138-173, wherein upon administration to an individual, the pharmaceutical composition according to embodiments 1-72 reduces intestinal irritation by at least 5% when compared to the pharmaceutical composition according to embodiments 1-72, except without the pharmaceutically-acceptable adjuvant.
175. The method according to embodiments 137 or 140-171 or the use according to embodiments 138-174, wherein upon administration to an individual, the pharmaceutical composition according to embodiments 1-72 reduces gastric irritation by at least 5% when compared to the pharmaceutical composition according to embodiments 1-72, except without the pharmaceutically-acceptable adjuvant.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, alcohols, lipids, pharmaceutical compositions, methods of preparing pharmaceutical compositions, or methods or uses of treating a chronic inflammation or disease associated with chronic inflammation.

Example 1

Liquid Formulations of Pharmaceutical Composition

This example illustrates how to make a pharmaceutical composition as disclosed herein as a liquid formulation.

Initially, 2,400 mg of ibuprofen was contacted directly with 2.0 mL of rapeseed oil in an attempt to dissolve a therapeutic compound directly into an adjuvant at a concentration of 1,200 mg/mL. However, ibuprofen remained insoluble in the oil and did not dissolve to substantially measureable degree. Ibuprofen remained insolubility even if the mixture was mixed by vortexing for 20 seconds, the contacting was done at 20° C. or 37° C., and/or the mixture was allowed to incubate for 24 hours at 20° C. or 37° C. The insolubility of ibuprofen in rapeseed oil was surprising given that ibuprofen has a log P value of 3.6; such a high log P value is indicative of a compound that would readily soluble in an adjuvant like oil.

Since, it was not possible to dissolve ibuprofen directly into oil, despite its high log P value, it was next tried to dissolve a therapeutic drug in a solvent to first create a solution comprising the compound. As a first step, experiments were conducted to the miscibility of a solvent in an adjuvant like oil in the absence of a therapeutic compound. In these experiments 0.5 mL ethanol was contacted with ten different volumes of rapeseed oil (Table 1). Each mixture was tested at 22° C. and at 37° C. in which the ethanol and oil were initially heated in a water bath before being mixed together. Mixing was attempted by vortex mixing for 20 seconds, and the containers were allowed to settle before visual assessment, either immediately, or after 24 hours. Each mixture was evaluated to determine whether or not the ethanol and rapeseed oil form immiscible layers, or a homogeneous mixture. The results are summarized in Table 1. Mixtures comprising solvent:adjuvant ratios of 1:1, 1:2, 1:3, 1:4, 1:5, and 1:6 formed immiscible layers at either 22° C. or at 37° C., either immediately or after 24 hours of incubation, indicating that the ethanol and oil did not mix well at these ratios. However, in solvent:adjuvant ratios above 1:7 a homogeneous mixture was formed under all conditions tested.

TABLE 1

Liquid Formulations without Therapeutic compound

| Components | | | Temperature | | | |
|---|---|---|---|---|---|---|
| Solvent (mL) | Adjuvant (mL) | Ratio | 22° C. | | 37° C. | |
| | | | Immediate | 24 hours | Immediate | 24 hours |
| 0.5 | 0.5 | 1:1 | IL | IL | IL | IL |
| 0.5 | 1.0 | 1:2 | IL | IL | IL | IL |
| 0.5 | 1.5 | 1:3 | IL | IL | IL | IL |
| 0.5 | 2.0 | 1:4 | IL | IL | IL | IL |
| 0.5 | 2.5 | 1:5 | IL | IL | IL | IL |
| 0.5 | 3.0 | 1:6 | IL | IL | IL | IL |
| 0.5 | 3.5 | 1:7 | HM | HM | HM | HM |
| 0.5 | 4.0 | 1:8 | HM | HM | HM | HM |
| 0.5 | 4.5 | 1:9 | HM | HM | HM | HM |
| 0.5 | 5.0 | 1:10 | HM | HM | HM | HM |

IL, Immiscible layers.
HM, Homogeneous mixture.

Once the appropriate ratios of alcohol and lipid necessary to form a homogenous mixture were determined, it was next determined whether contacting a therapeutic compound first in a solvent before contacting with an adjuvant would result in the compound dissolving in the solvents. To conduct these experiments, either 1,000 mg or 1,200 mg of ibuprofen was dissolved into 0.5 mL of ethanol. The resulting alcohol solution was then contacted with rapeseed oil at two different solvent:adjuvant ratios (1:2 and 1:9). Each mixture was tested at 20° C. and at 37° C. in which the ethanol solution and oil were initially heated in a water bath before being mixed together. Mixing was attempted by vortex mixing for 20 seconds, and the containers were allowed to settle before visual assessment, either immediately, or after 24 hours. Each mixture was evaluated to determine whether or not the ethanol solution and rapeseed oil form immiscible layers, or a homogeneous mixture. The results are summarized in Table 2. In contrast to the situation in the absence of a therapeutic compound, when ibuprofen is present in the ethanol, it caused the ethanol and oil to form a homogeneous mixture under all conditions tested in solvent:adjuvant ratios above 1:2. This observation was very surprising because, although not wish to be bound by any theory, it appears that a therapeutic compound may be having some effect on the manner in which an adjuvant and solvent interact with each other, such that a homogeneous mixture is formed in a way that does not occur when the therapeutic compound is absent. In addition, the results indicate that a therapeutic compound can be formulated at clinically useful concentrations.

TABLE 2

Liquid Formulations with Therapeutic Compound

| Components | | | | Temperature | | | |
|---|---|---|---|---|---|---|---|
| Compound (mg) | Solvent (mL) | Adjuvant (mL) | Ratio | 22° C. | | 37° C. | |
| | | | | Immediate | 24 hours | Immediate | 24 hours |
| 500 | 0.5 | 1.0 | 1:2 | HM | HM | HM | HM |
| 600 | 0.5 | 1.0 | 1:2 | HM | HM | HM | HM |
| 500 | 0.5 | 4.5 | 1:9 | HM | HM | HM | HM |
| 600 | 0.5 | 4.5 | 1:9 | HM | HM | HM | HM |

IL, Immiscible layers.
HM, Homogeneous mixture.

Example 2

Liquid Formulations of Pharmaceutical Composition

This example illustrates how to make a pharmaceutical composition as disclosed herein as a liquid formulation.

To prepare a pharmaceutical composition disclosed herein using gemfibrozil, the following formulations were examined. In these experiments, 600 mg gemfibrozil was contacted with different volumes of ethanol, as the solvent, warmed to 37° C., and the resulting solution was then contacted with different volumes of linseed oil, as the adjuvant, warmed to 37° C. (Table 3). Each formulation was evaluated to determine whether or not the ethanol and linseed oil form immiscible layers, a clear homogeneous mixture, as well as whether or not the gemfibrozil crystallized out of solution. The results are summarized in Table 3.

Like ibuprofen in Example 1 above, gemfibrozil remained insoluble in the oil alone and did not dissolve to substantially measureable degree. The formulation comprising 0.2 mL ethanol was unable to completely dissolve gemfibrozil. In addition, although the formulation comprising 0.3 mL ethanol was capable of dissolving gemfibrozil, the therapeutic compound began to crystallizing out of solution within 3 hours and complete crystallization occurred within 48 hours. All other formulations tested were capable of dissolving gemfibrozil and forming a pharmaceutical composition disclosed herein. However, only the formulation comprising 0.5 mL ethanol appeared to for a stable pharmaceutical composition in that gemfibrozil remained completely dissolved after three weeks.

TABLE 3

Liquid Formulations with Therapeutic Compound

| Components | | | | Temperature | |
|---|---|---|---|---|---|
| Compound | Solvent | Adjuvant | | 22° C. | |
| (mg) | (mL) | (mL) | Ratio | Immediate | 3 weeks |
| 600 | 0 | 1.0 | — | IM | N/A |
| 600 | 0.2 | — | — | IM | N/A |
| 600 | 0.3 | 0.6 | 1:2 | CR | CR |
| 600 | 0.4 | 0.4 | 1:1 | HM | CR |
| 600 | 0.4 | 0.8 | 1:2 | HM | CR |
| 600 | 0.5 | 1.0 | 1:2 | HM | HM |

HM, Clear homogeneous mixture.
CR, Crystallization.
IM, Immiscible.

Example 3

Liquid Formulations of Pharmaceutical Composition

This example illustrates how to make a pharmaceutical composition as disclosed herein as a liquid formulation.

To prepare a pharmaceutical composition disclosed herein using ibuprofen, the following formulation was performed. In these experiments, 4 g ibuprofen was contacted with 3.6 mL of ethyl acetate, as the solvent, and the resulting solution was then contacted with 76.4 mL of rapeseed oil, as the adjuvant. The resulting pharmaceutical composition had a solvent:adjuvant ratio of about 1:21. This pharmaceutical composition was then placed in a round bottom flask and subjected to low pressure on a rotary evaporator. The temperature was kept low and evaporation continued to constant weight. The total volume lost was 3.65% of the total weight. The resulting liquid no longer retained the characteristic ethyl acetate odor/taste, indicating that there was a substantial removal of ethyl acetate form the pharmaceutical composition.

Example 4

Solid Formulation of Pharmaceutical Composition

This example illustrates how to make a pharmaceutical composition as disclosed herein as a solid formulation.

Since certain fatty acids are liquid at room temperature, while others are solid, an examination of the different fatty acids was undertaken in an effort to evaluate the potential of each fatty acid in the manufacture of a solid formulation. This understanding would enable the development of a wide array of solid formulation by adjusting the relative ratios of each fatty acid. As an initial experiment, linolenic acid, linoleic acid, palmitic acid and stearic acid were evaluated to assess whether it was possible to prepare a pharmaceutical composition disclosed herein that could be formulated using only one of these fatty acids to be a solid or semi-solid at 22° C. (simulating room temperature conditions), but melt into a liquid at 37° C. (simulating internal body temperature conditions after ingestion).

Four different test formulations were prepared and evaluated on their ability to form a solid dose formulation at 22° C. and melt into a homogeneous solution at 37° C. without forming a suspension (Table 4). Formulation 1 was prepared by dissolving 200 mg of Ibuprofen into 400 mg of menthol, and the resulting solution was then mixed with 200 mg of stearic acid ($T_m$ of about 67-72° C.) and heated at 60° C. for 30 minutes to form a homogeneous solution. Formulation 1 solidified immediately upon cooling to 22° C. Formulation 1 remained a solid even after incubating at 37° C. overnight. Formulation 2 was prepared by dissolving 200 mg of Ibuprofen into 400 mg of menthol, and the resulting solution was then mixed with 200 mg of palmitic acid ($T_m$ of about 61-62° C.) and heated at 60° C. for 30 minutes to form a homogeneous solution. Formulation 2 solidified about 1 hour after cooling to 22° C. Incubating at 37° C. overnight cause Formulation 2 to completely melt into a clear homogenous liquid. However, Formulation 2 once again solidified about 1 hour after cooling to 22° C. Formulation 3 was prepared by dissolving 200 mg of Ibuprofen into 400 mg of menthol, and the resulting solution was then mixed with 200 mg of linoleic acid ($T_m$ of about −5° C.) and heated at 37° C. for 2 hours to form a homogeneous solution. Formulation 3 remained a liquid, even after cooling to 22° C. for 72 hours. Formulation 4 was prepared by dissolving 200 mg of Ibuprofen into 400 mg of menthol, and the resulting solution was then mixed with 200 mg of linolenic acid ($T_m$ of about −11° C.) and heated at 37° C. for 2 hours to form a homogeneous solution. Formulation 4 remained a liquid, even after cooling to 22° C. for 72 hours.

TABLE 4

Solid Formulations with Therapeutic Compound

| Components | | | | Temperature | | |
|---|---|---|---|---|---|---|
| Compound | Solvent | Adjuvant | | 22° C. | 37° C. | |
| (mg) | (mg) | (mg) | Ratio | Upon Cooling | 24 hours | 72 hours |
| 200 | 400 | 200 (stearic acid) | 2:1 | Solid | Solid | — |
| 200 | 400 | 200 (palmitic acid) | 2:1 | Solid | Liquid | — |
| 200 | 400 | 200 (linoleic acid) | 2:1 | Liquid | Liquid | Liquid |
| 200 | 400 | 200 (linolenic acid) | 2:1 | Liquid | Liquid | Liquid |

Based on these data, a solid dosage form of a pharmaceutical composition disclosed herein can be made. For example, a pharmaceutical composition will be formulated to be solid or semi-solid at 22° C., but melt into a proper clear solution (and not a suspension) at 37° C. (Table 5).

TABLE 5

Solid Formulations of Pharmaceutical Compositions

| | |
|---|---|
| Compound | 600 mg Ibuprofen |
| Solvent | 500 mg Methanol |
| Adjuvant | 2000 mg Palmitic acid |
| | 2000 mg Stearic acid |
| | 250 mg Linolenic acid |
| | 250 mg Linoleic acid |
| Ratio | 1:9 |
| Volume | 5 mL |
| Concentration | 120 mg/mL |

Example 5

Animal Model for Intestinal Erosion

To assess whether a pharmaceutical composition disclosed herein reduced gastric irritation, experiments were conducted using an intestinal erosion murine model.

Sprague-Dawley rats were divided into seven experimental groups containing five animals each. After fasting overnight, the animals were challenged with one with one of seven different treatments. Group A was a control in which each mouse was orally administered 1% methylcellulose/ 0.5% polysorbate 80 vehicle only. Group B was a control in which each mouse was orally administered solvent/adjuvant vehicle only (gavage of 10% ethanol and 90% linseed oil). Group C was a control in which each mouse was orally administered 150 mg/kg aspirin. Group D was a control in which each mouse was orally administered 100 mg/kg ibuprofen suspended in 1% methylcellulose/0.5% polysorbate 80. Group E was the experimental group in which each mouse was administered a pharmaceutical composition disclosed herein (BC1054-100) comprising 100 mg/kg of ibuprofen, 10% ethanol, and 90% linseed oil. Group F was a control in which each mouse was orally administered 100 mg/kg ibuprofen suspended in 1% methylcellulose/0.5% polysorbate 80. Group G was the experimental group in which each mouse was administered a pharmaceutical composition disclosed herein (BC1054-200) comprising 200 mg/kg of ibuprofen, 10% ethanol, and 90% linseed oil. Animals were sacrificed 4 hours after treatment and the stomachs were examined for degree of hemorrhage and severity of mucosal erosive lesions. Gastric irritation was scored as follows: 0, no lesions; 1, hyperemia; 2, one or two slight lesions; 3, more than two slight lesions or severe lesions; and 4, very severe lesions. A score of 50% or more relative to Group C (aspirin-treated control group), which was set to 100%, was considered a positive score for gastric irritation.

Results are shown in Table 6. Group D (100 mg/kg of ibuprofen-treated control group) and Group F (200 mg/kg of ibuprofen-treated control group) produced gastric lesions that were 75% and 95%, respectively, severe as those induced by Group C (aspirin-treated control group). However, Group E (BC1054-100-treated experimental group) and Group G (BC1054-200-treated experimental group) produced gastric lesions that were 20% and 40%, respectively, as severe as those associated with Group C (aspirin-treated control group). These results demonstrate that that a pharmaceutical composition disclosed herein reduced the extent to which a therapeutic compound may cause mucosal lesions and cause gastric irritation.

TABLE 6

Results from Intestinal Erosion Assay

| Group | Mean Ulceration Score | % Aspirin Erosion |
|---|---|---|
| A | 0 | 0 |
| B | 0 | 0 |
| C | 4 | (100) |
| D | 3 | 75[1] |
| E | 0.8 | 20 |
| F | 3.8 | 95[1] |
| G | 1.6 | 40 |

[1]Positive score for gastric erosion.

Example 6

Animal Model for a Respiratory Inflammation

To assess the effectiveness of a pharmaceutical composition disclosed herein in treating a respiratory inflammation, experiments were conducted using a viral-induce influenza murine model.

C57BLK/6 female mice (6-7 weeks old) were divided into three experimental groups containing ten animals each. On day 1, animals received an intranasal lethal dose (50 μL total, 25 μL/nostril) of Influenza A/PR/8/34 under halothane-induced anaesthesia. On day 3, post-challenge with the virus, the animals received one of three treatments. Group A was a control in which each mouse was orally administered 335.6 μg of ibuprofen dissolved in 10 μL DMSO (no adjuvant). Group B was a control in which each mouse was orally administered solvent/adjuvant vehicle only (gavage of 10% ethanol and 90% linseed oil). Group C was the experimental group in which each mouse was administered a pharmaceutical composition disclosed herein (BC1054) comprising 335.6 μg of ibuprofen, 10% ethanol, and 90% linseed oil. A dose of 335.6 μg of ibuprofen in the mouse is equivalent to 20 mg/kg/day, or 1200 mg/day for a human (the maximum standard dose for ibuprofen). Animals were weighed, and monitored for signs of infection daily for up to day 6 when all animals were culled. FIG. 1 clearly shows that oral administration of the solvent/adjuvant vehicle only (Group B) had an 80% mortality rate and that oral administration of ibuprofen only (Group A) exhibited a mortality rate of 60%. However, a single oral administration of BC1054 reduced the mortality rate to only 20%.

To determination of levels of IL-10 and IL-4, an ELISA was performed using a 96-well plate coated with a capture antibody for IL-10 or IL-4. Lungs collected from the culled mice were homogenized at 4° C., and the supernatant collected and stored at −70° C. until needed. Thawed samples were vortexed for 30 seconds immediately before adding to the ELISA plate. Serial dilutions were performed within the plate with both the sample and the standards by pipetting 60 μL of assay diluent into each well. The plate was sealed and incubated for 2 hours at room temperature. For IL-4, 60 μL of working detector was added (Detection Antibody+SAv-HRP reagent) to each well. The plate was sealed and incubated for 1 hour at room temperature. For IL-10, 60 μL of detection antibody was diluted in assay diluent to each well. Plates were washed and 60 μL of SAv-HRP enzyme was diluted in assay diluent and added to the plate. The plate was sealed and incubated for 20 minutes at room temperature. Plates were then washed ten times. 60 μL of substrate solution were added to each well and the plate was incubated for 30 minutes at room temperature in the dark. 60 μL of stop solution was added to each well and absorbance was read at 450 nm. IL-10 and IL-4 concentrations were expressed as pg/mg of lung tissue. These results indicate that a pharmaceutical composition disclosed herein was effective in treating a respiratory inflammation.

Figure 2A:
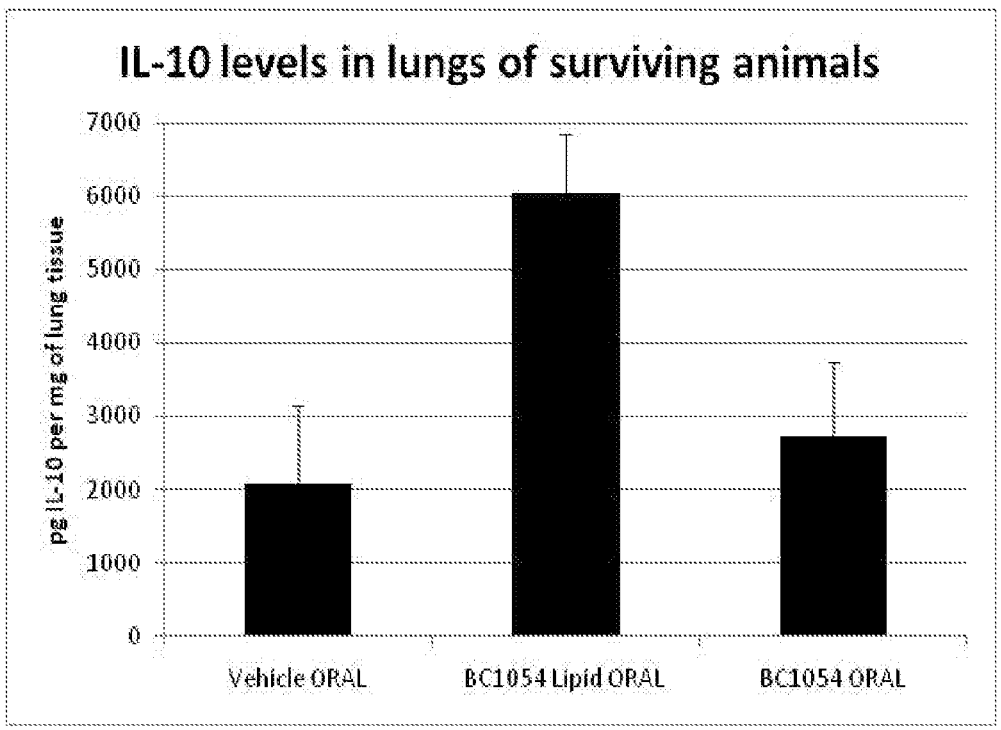
FIG. 2A-B show the effects of a pharmaceutical composition disclosed herein on in vivo levels of Th2 cytokines in the lungs of surviving mice.
Figure 2B:
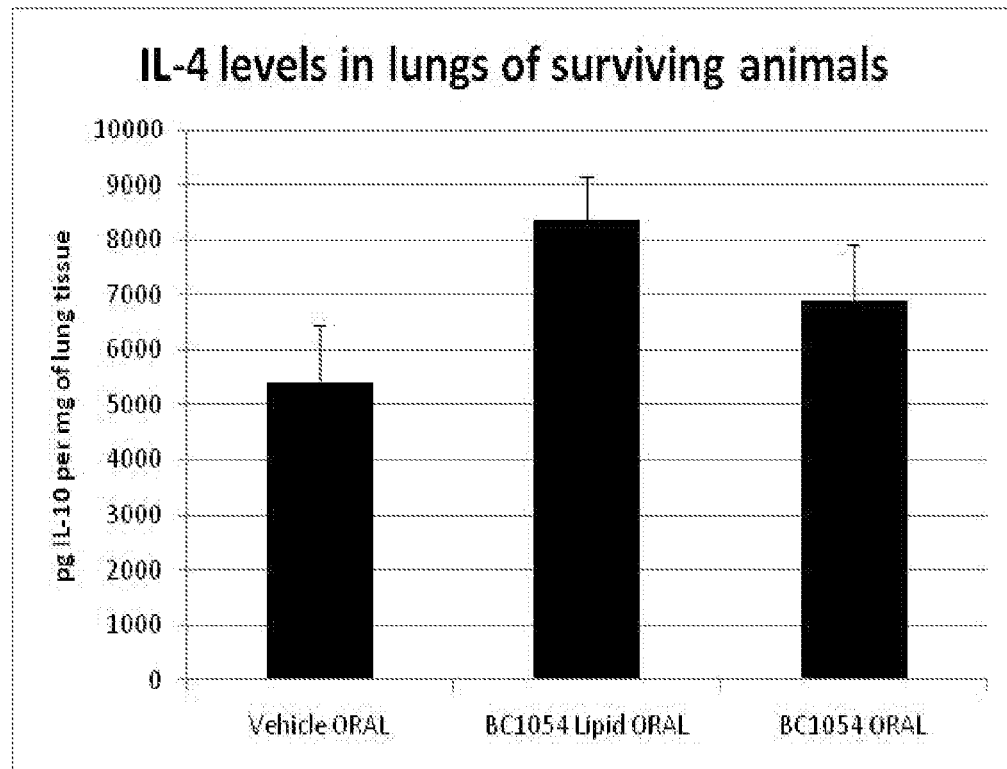

Results show that animals from the Group A (ibuprofen-treated control group) and Group B (solvent/adjuvant vehicle-treated control group) controls exhibited 2600 pg/mg and 2000 pg/mg of IL-10, respectively (FIG. 2A). However, Group C (BC1054-treated experimental group) revealed an IL-10 concentration of 6000 pg/mg, 3-fold higher than that seen in the control animals. These result also shows that animals from the Group A (ibuprofen-treated control group) and Group B (solvent/adjuvant vehicle-treated control group) controls exhibited 6900 pg/mg and 5400 pg/mg of IL-4, respectively, while Group C (BC1054-treated experimental group) exhibited an IL-4 concentration of 8300 pg/mg (FIG. 2B). Taken together, synergistic increase in IL-10 levels and/or the increase in IL-4 levels suggest that at least part of the efficacy observed for BC1054 was by inducing a switch from a Th1 to a Th2 response.

Further experiments were done to further determine which cell types were stimulated to release cytokines upon administration of a BC1054. C57BLK/6 female mice (6-7 weeks old) were divided into three experimental groups containing ten animals each. On day 1, animals received an intranasal lethal dose (50 μL total, 25 μL/nostril) of Influenza H1N1 under halothane-induced anaesthesia. On day 3, post-challenge with the virus, the animals received one of three treatments. Group A was a control in which each mouse was orally administered 335.6 μg of ibuprofen dissolved in 10 μL DMSO (no adjuvant). Group B was a control in which each mouse was orally administered solvent/adjuvant vehicle only (gavage of 10% ethanol and 90% linseed oil) (no ibuprofen). Group C was the experimental group in which each mouse was administered a pharmaceutical composition disclosed herein (BC1054) comprising 335.6 µg of ibuprofen, 10% ethanol, and 90% linseed oil. Lungs collected from fatally-infected mice were homogenized at 4° C., and the supernatant collected, stored, and IL-10, TNFα and IFNγ levels measured using an ELISA.

Figure 3A:
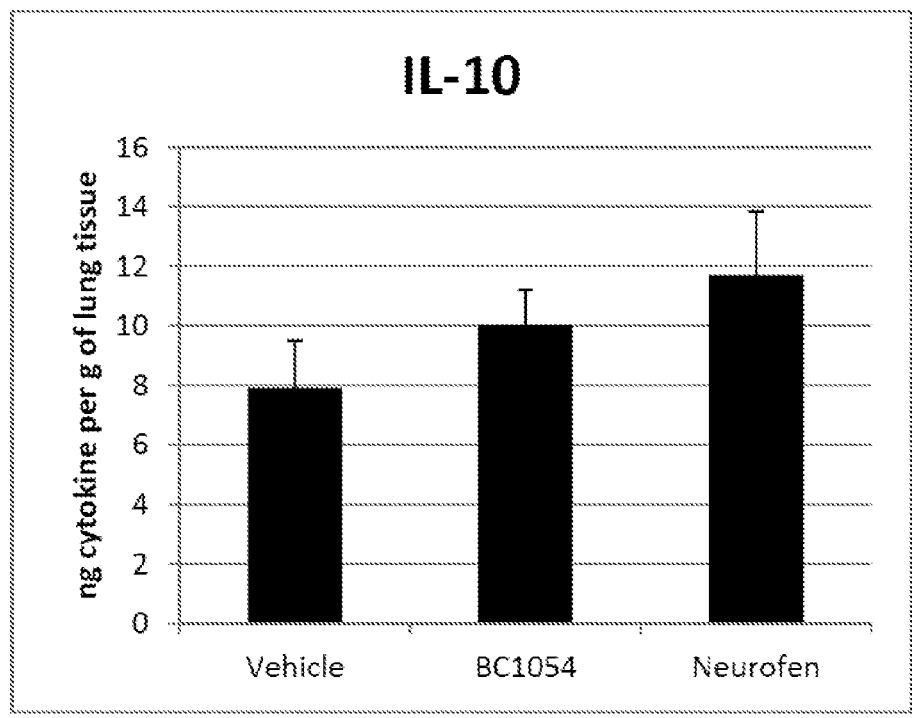
FIG. 3A-C show the effects of a pharmaceutical composition disclosed herein on in vivo levels of Th2 cytokines in the lungs of surviving mice.
Figure 3B:
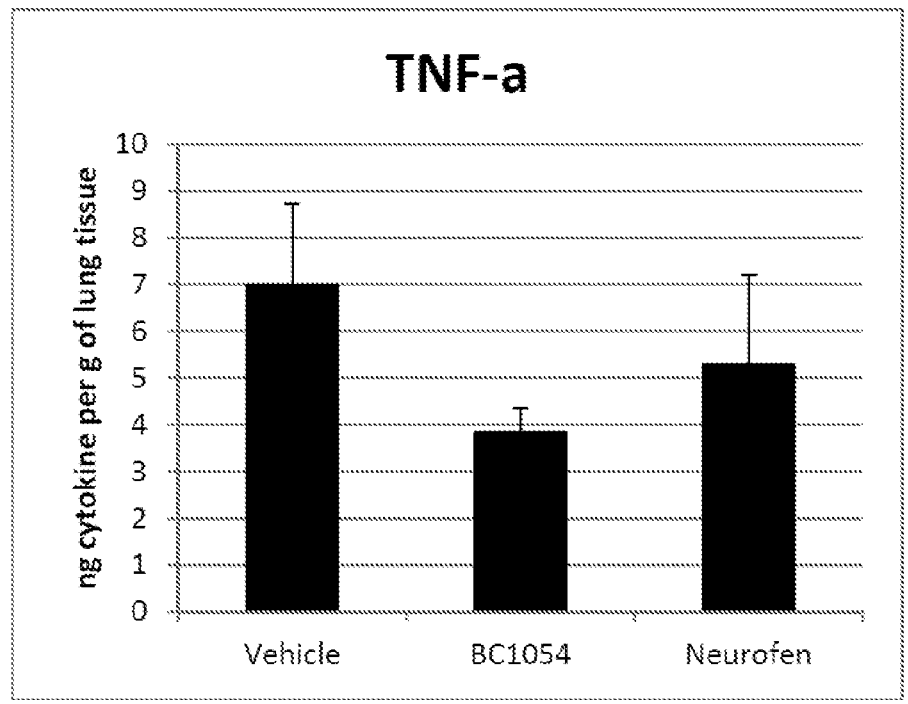
Figure 3C:
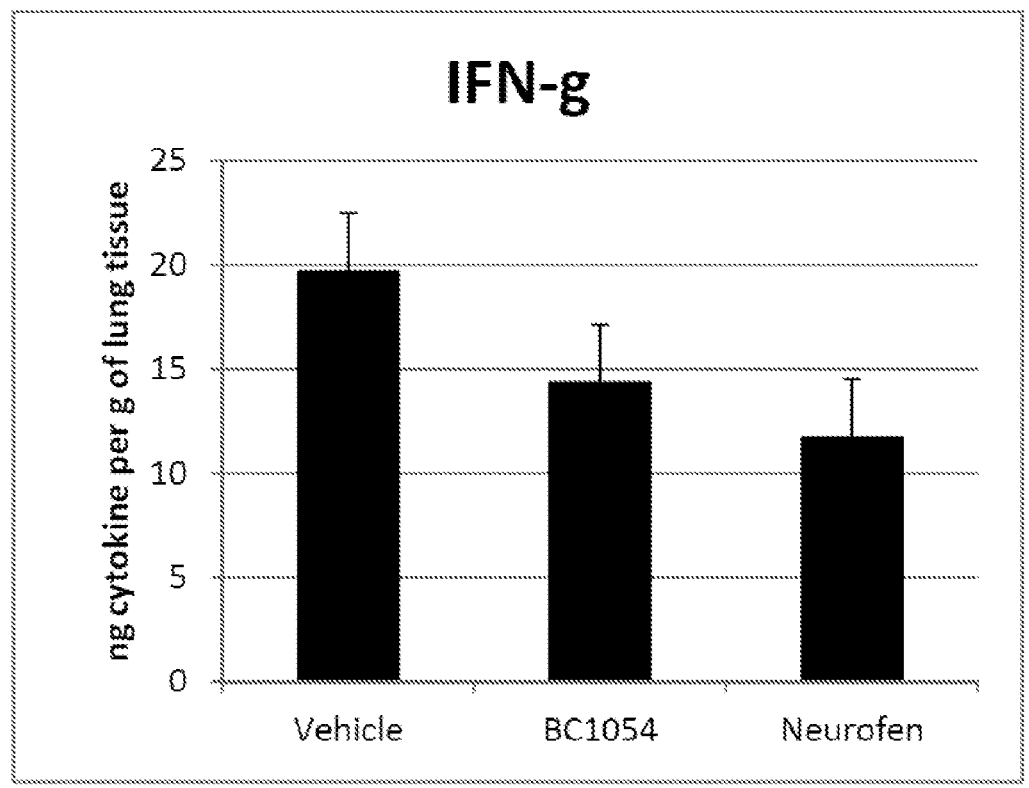

The results show that Group A (ibuprofen-treated control group) and Group C (BC1054-treated experimental group) animals exhibited an increased IL-10 levels (FIG. 3A). However, these IL-10 increases were associated with very different pharmacodynamic effects, and the pattern of pro-inflammatory cytokine reduction highlights the source of the IL-10 and its relevance to the effect on survival. For example, TNFα (which is macrophage-related cytokine) was not as markedly inhibited (FIG. 3B) in Group A (ibuprofen-treated control group) animals, whereas the levels of IFNγ (which is a lymphocyte-derived cytokine) were markedly lowered in this group when compared to Group C (BC1054-treated experimental group) animals (FIG. 3C). This cytokine release pattern was associated with a poor outcome. However, in Group C (BC1054-treated experimental group) animals, TNFα levels were markedly lowered (FIG. 3B), while IFNγ levels were largely unaffected (FIG. 3C). This demonstrates that a pharmaceutical composition disclosed herein shows a protective effect on the H1N1-induced lethality through, in part, a macrophage-derived IL-10 levels rather than lymphocyte-derived IL10.

Example 7

Animal Model for Inflammatory Bowel Disease

To assess the effectiveness of a pharmaceutical composition disclosed herein in treating an inflammatory bowel disease, experiments were conducted using a TBS-induced colitis murine model.

C57Bl/6 male mice (6-7 weeks old) were divided into seven experimental groups containing at least ten animals each. On day 0, colitis was induced in mice from Groups B-G by intrarectal administration of 100 µL of TNBS (4 mg) in 50% ethanol under isoflurane anesthesia. Animals were dosed either once or three times a day from day −1 to day 5 with one of seven different treatments. Group A was a control in which each mouse was orally administered ethanol vehicle only. Group B was a control in which each mouse was orally administered 1% methylcellulose vehicle only. Group C was a control in which each mouse was orally administered solvent/adjuvant vehicle only (gavage of 10% ethanol and 90% linseed oil). Group D was a control in which each mouse was orally administered 3 mg/kg of Prednisolone. Group E was a control in which each mouse was orally administered 20 mg/kg of ibuprofen suspended in 1% methylcellulose (1 mL/kg) (no adjuvant). Group F was the experimental group in which each mouse was administered a pharmaceutical composition disclosed herein (BC1054-20) comprising 20 mg/kg of ibuprofen, 10% ethanol, and 90% linseed oil. Group G was the experimental group in which each mouse was administered a pharmaceutical composition disclosed herein (BC1054-30) comprising 30 mg/kg of ibuprofen, 10% ethanol, and 90% linseed oil. All animals were weighed daily and assessed visually for the presence of diarrhea and/or bloody stool. On day 3 and on day 5 colitis severity was assessed in all animals using video endoscopy, where images were taken and colitis severity scored visually by a blinded observer on a scale from 0 to 4 as follows: 0, normal; 1, loss of vascularity; 2, loss of vascularity and friability; 3, friability and erosions; and 4, ulcerations and bleeding. Following endoscopy on day 5, animals were sacrificed and the colon removed and its length and weight measured. Serum samples were obtained and the colon was fixed in 10% formalin. An additional piece of colon tissue was collected, weighed, and snap frozen in liquid nitrogen.

Results from these experiments are shown in Table 7. Group B (TNBS-treated control group) showed a statistically significant difference in mean weight change when compared to Group A (untreated ethanol control group), all other group comparisons showed no difference in mean weight change. Group B (TNBS-treated control group) showed a statistically significant decrease in mean colon length when compared to Group A (untreated ethanol control group). Additionally, Group D (Prednisolone-treated control group), Group F (BC1054-20-treated experimental group), and Group G (BC1054-30-treated experimental group) all showed a statistically significant increase in mean colon length when compared to Group B (TNBS-treated control group). Although Group B (TNBS-treated control group) showed a statistically significant increase in mean colon weight when compared to Group A (untreated ethanol control group), all other group comparisons showed no difference in mean colon weight. With regards to the endoscopy colitis score, Group D (Prednisolone-treated control group) showed a statistically significant reduced mean colitis scores on both day 3 and day 5 when compared to Group B (TNBS-treated control group). In a similar manner, both Group F (BC1054-20-treated experimental group) and Group G (BC1054-30-treated experimental group) showed a statistically significant reduced mean colitis scores on day 5 when compared to Group B (TNBS-treated control group). These results indicate that a pharmaceutical composition disclosed herein was effective in treating an inflammatory bowel disease.

TABLE 7

Results from Inflammatory Bowel Disease

| Group | Mean Animal Weight | Mean Colon Length | Mean Colon Weight | Endoscopy Colitis Severity Score Day 3 | Endoscopy Colitis Severity Score Day 5 |
|---|---|---|---|---|---|
| A | 23.93 g | 8.5 cm | 215 mg | 0.2 | 0 |
| B | 21.98 g[1] | 7.3 cm[2] | 295 mg[6] | 3.1 | 2.7 |
| C | 23.64 g | 7.8 cm | 239 mg | 2.9 | 2.4 |
| D | 23.33 g | 8.4 cm[3] | 267 mg | 2.3[7] | 1.7[8] |
| E | 23.82 g | 7.9 cm | 267 mg | 2.7 | 2.2 |
| F | 23.69 g | 8.4 cm[4] | 258 mg | 2.6 | 1.9[9] |
| G | 24.25 g | 7.9 cm[5] | 284 mg | 2.4 | 1.4[10] |

[1]Statistically significance difference compared to Group A (p = 0.029).
[2]Statistically significance difference compared to Group A (p = 0.001).
[3]Statistically significance difference compared to Group B (p = 0.001).
[4]Statistically significance difference compared to Group B (p = 0.001).
[5]Statistically significance difference compared to Group B (p = 0.034).
[6]Statistically significance difference compared to Group A (p = 0.009).
[7]Statistically significance difference compared to Group B (p = 0.005).
[8]Statistically significance difference compared to Group B (p = 0.002).
[9]Statistically significance difference compared to Group B (p = 0.045).
[10]Statistically significance difference compared to Group B (p = 0.002).

Example 8

Animal Model for a Systemic Arthritis

To assess the effectiveness of a pharmaceutical composition disclosed herein in treating arthritis, experiments were conducted using an α-collagen antibody induced arthritis (ACAIA) murine model that mimics a systemic arthritis like rheumatoid arthritis.

BALB/c mice, on day 0, were intravenously injected with a single inoculation with 2 mg/200 μL of an α-collagen II monoclonal antibody, followed by an intraperitoneal injection of 50 μg/200 μL of lipopolysaccharide (LPS) at day 3. From day 3 and daily until day 8 and then on days 10 and 12, paw volumes (plethysmography) and arthritis scores were taken. The same animals were also treated daily from days 0 to day 11, the animals received one of six treatments. Group A was a control in which each mouse was orally administered phosphor-buffered saline (PBS) vehicle only. Group B was a control in which each mouse was intraperitoneally administered 10 mg/kg of Enbrel in PBS. Group C was a control in which each mouse was orally administered 1% methylcellulose vehicle only. Group D was a control in which each mouse was orally administered 40 mg/kg of ibuprofen suspended in 1% methylcellulose (1 mL/kg) (no adjuvant). Group E was a control in which each mouse was orally administered solvent/adjuvant vehicle only (gavage of 10% ethanol and 90% linseed oil). Group F was the experimental group in which each mouse was orally administered a pharmaceutical composition disclosed herein (BC1054-20) comprising 20 mg/kg of ibuprofen, 10% ethanol, and 90% linseed oil. Group G was the experimental group in which each mouse was orally administered a pharmaceutical composition disclosed herein (BC1054-30) comprising 30 mg/kg of ibuprofen, 10% ethanol, and 90% linseed oil. Through the entire experiment (12 days), animals were checked daily for clinical signs (general observations of the health of the animal) and body weights. Total arthritis scores are determined by summing the arthritis scores of individual paws using the following grades: 0=no signs of arthritis, 1=mild but definite redness and swelling of the ankle/wrist or apparent redness or swelling limited to individual digits, regardless of the number of affected digits, 2=moderate to severe redness and swelling of the ankle/wrist, 3=redness and swelling of the entire paw including digits, 4=maximally inflamed limb with involvement of multiple joints.

Figure 4:
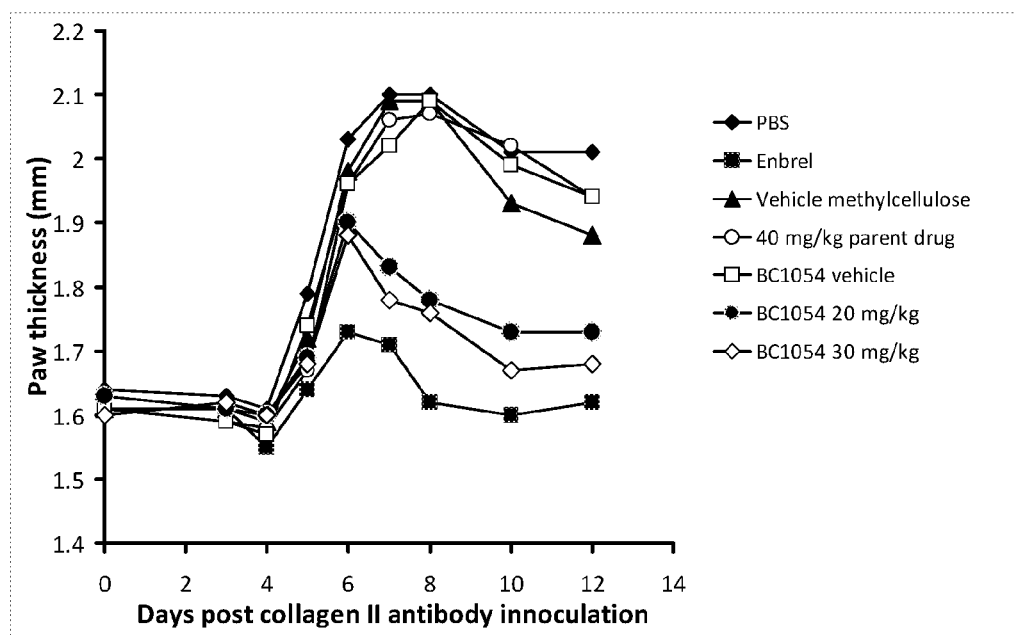
FIG. 4 shows the effects of a pharmaceutical composition disclosed herein on arthritis using an α-collagen antibody induced arthritis (ACAIA) murine model. PBS=Group A; Enbrel=Group B; Vehicle methylcellulose=Group C; 40 mg/kg parent drug=Group D; BC1054 vehicle=Group E; BC1054 20 mg/kg=Group F; and BC1054 30 mg/kg=Group G.

The results of this experiment are shown in FIG. 4. As expected, Group B (Enbrel-treated control group) animals showed the best results, with the lowest paw thicknesses at about 1.6 mm on day 12. The two pharmaceutical compositions, Group F (BC1054-20-treated experimental group) and Group G (BC1054-30-treated experimental group) animals displayed the next best results, with Group G mice producing a paw thickness of only 1.7 mm, and Group F mice producing a paw thickness of about 1.73 mm. The negative control Group A (PBS vehicle-treated control group), Group C (methoxycellulose vehicle-treated control group), and Group E (solvent/adjuvant vehicle-treated control group) animals, as well as Group D (ibuprofen-treated control group) performed significantly worse with paw thicknesses of 1.9 mm and over when compared to Group F and Group G animals. These results indicate that a pharmaceutical composition disclosed herein was effective in treating an arthritis.

Example 9

Case Studies for the Treatment of Chronic Inflammation

A 47 year old female was diagnosed with reactive arthritis in one knee was treated with a pharmaceutical composition disclosed herein (BC1054) comprising 20 mg/kg of ibuprofen, 10% ethanol, and 90% rapeseed oil (1200 mg uid) over a 3 day period and found that the swelling and pain started to go away after 1 day and was completely better after 3 days. Ineffective standard ibuprofen treatment was subsequently ceased. At a 3 month follow up, no signs of the reactive arthritis have been observed.

A 50 year old male was diagnosed with a chronically inflamed ankle after a maison neuve fracture in the ankle. The patient was taking 30 mg codeine with 500 mg paracetamol bid, along with 10 mg diclofenac tid for 8 months to control pain. He took a 5 day course of a pharmaceutical composition disclosed herein (BC1054) comprising 20 mg/kg of ibuprofen, 10% ethanol, and 90% rapeseed oil (600 mg bid) and after 2 days reported a significant improvement in his pain, and then after 3 days he reported that the pain was completely controlled. He has subsequently ceased the codeine, paracetamol and diclofenac, and after a 2 month follow the patient is still pain free.

A 33 year old female diagnosed with stress related eczema, had an acute flare of moderate eczema on arms and chest. A pharmaceutical composition disclosed herein (BC1054) comprising 20 mg/kg of ibuprofen, 10% ethanol, and 90% rapeseed oil (1200 mg uid) was administered for 7 days. After a couple of hours the lesion ceased itching, after 1 day a noticeable improvement in lesion swelling was reported. 2-3 days later the eczema lesions erythema had resolved and after 7 days the lesions had completely disappeared. In the past the patient had used emollients and hydrocortisone creams, which made the lesions worse and would often lead to a course of antibiotics. The patient commented that her response to the BC1054 treatment was quick and complete, and was a marked improvement on previously pharmacological therapies.

An 85 year old male diagnosed with reactive osteoarthritis, with marked swelling and severe pain in both knee. For 1 year, the patient had been prescribed prednisolone and NSAIDS to control arthritis, with no effect. In addition the patient had taken daily glucosamine. Despite considerable pharmacological intervention, the patient regularly flared resulting in considerable restriction of mobility. The patient was given a 10 day course of a pharmaceutical composition disclosed herein (BC1054) comprising 20 mg/kg of ibuprofen, 10% ethanol, and 90% rapeseed oil (400 mg tid) and experience an appreciable improvement by day 3 and a complete resolution after the completion of the course. The patient reported that his mobility was returned to normal and he has remained in remission at is 1 month examination.

A 38 years old male with reactive osteoarthritis in 1 knee, for 6 months (pain and swelling). Over that period, the patient had tried a comprehensive spectrum of pharmacological therapies: prednisolone, Humira and sulfasalazine, alongside NSAIDs to control pain. Only the sulfasalazine had any appreciable effect, however the patient disliked its side effects, so requested to come off the sulfasalazine. After 2 weeks of being sulfsalazine free, the patient experienced a flare of the reactive arthritis and commenced a 4 day course of a pharmaceutical composition disclosed herein (BC1054) comprising 20 mg/kg of ibuprofen, 10% ethanol, and 90% rapeseed oil (600 mg bid), experiencing complete remission of the arthritis. After 2 weeks of being drug free, the arthritis began to flare again and the patient was put on another 4 day treatment of BC1054, again experiencing complete remission. This time the arthritis flared again 1 week later. To account for this, the patient was given a final 10 day course of BC1054. Subsequently, the arthritis remained in remission for 11 months, as per the last examination.

A 49 year old male diagnosed with hypercholesterolemia (LDL of 4.35 mmol/L) was placed on a pharmaceutical composition disclosed herein (BC1054) comprising 20 mg/kg of ibuprofen, 10% ethanol, and 90% rapeseed oil (600 mg bid) for 7 days. After 5 days of treatment the patient's LDL levels had normalized to 3.89 mmol/L. The normalization of LDL level persisted for 2 months after cessation of BC1054 dosing, as determined at the last examination.

A 60 year old male newly diagnosed with hypercholesterolemia (LDL of 4.31 mmol/L) was given a course of a pharmaceutical composition disclosed herein (BC1054) comprising 20 mg/kg of ibuprofen, 10% ethanol, and 90% rapeseed oil (1200 mg uid) to lower LDL levels to within the normal range. After 5 days of treatment the patients LDL levels were lowered to 3.36 mmol/L. The patient was followed up for 1 month and his LDL remained within the normal range, despite there being no further BC1054 dosing.

Example 10

Treatment of Chronic Inflammation

A 62 year old female complains of joint stiffness and swelling and is diagnosed with rheumatoid arthritis. A physician determines that the joint stiffness and swelling is due to chronic inflammation. The woman is treated by oral administration a pharmaceutical composition comprising ibuprofen as disclosed herein taken twice daily. Alternatively, the woman is treated by oral administration a pharmaceutical composition comprising aspirin as disclosed herein taken thrice daily. Alternatively, the woman is treated by oral administration a pharmaceutical composition comprising naproxen as disclosed herein taken twice daily. The woman's condition is monitored and after about 3 days of treatment the woman indicates there is reduced joint stiffness and swelling. At one and three month check-ups, the woman indicates that she continues to have reduced joint stiffness and swelling in the area treated. This reduction in chronic inflammation symptoms indicates successful treatment with the pharmaceutical composition disclosed herein. A similar type of oral administration of a pharmaceutical composition disclosed herein will be used to treat a patient suffering from chronic inflammation associated with any monoarthritis, oligoarthritis, or polyarthritis, such as, e.g., osteoarthritis, juvenile idiopathic arthritis, septic arthritis, a spondyloarthropathy (including ankylosing spondylitis, reactive arthritis (Reiter's syndrome), psoriatic arthritis, enteropathic arthritis associated with inflammatory bowel disease, Whipple disease or Behcet disease), a synovitis, gout, pseudogout, or Still's disease, as well as, a bursitis, a rheumatic fever, or a tenosynovitis. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 58 year old male complains of breathing difficulty and is diagnosed with chronic obstructive pulmonary disease (COPD). A physician determines that the breathing difficulty is due to chronic inflammation. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is improvement in his ability to breath. At one and three month check-ups, the man indicates that he continues to have improved breathing. This reduction in a chronic inflammation symptom indicates successful treatment with the pharmaceutical composition disclosed herein. A similar type of oral administration of a pharmaceutical composition disclosed herein will be used to treat a patient suffering from chronic inflammation associated with an asthma, a bronchiolitis, a bronchitis, an emphysema, a laryngitis, a pharyngitis, a pleuritis, a pneumonitis, a rhinitis, a sinusitis, or any other type of chronic respiratory disorder. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 67 year old male complains of muscle soreness and is diagnosed with dermatomyositis. A physician determines that the soreness is due to chronic inflammation. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is reduced soreness. At one and three month check-ups, the man indicates that he continues to have improved muscle movement and reduced soreness This reduction in a chronic inflammation symptom indicates successful treatment with the pharmaceutical composition disclosed herein. A similar type of oral administration of a pharmaceutical composition disclosed herein will be used to treat a patient suffering from chronic inflammation associated with an inclusion body myositis, a myasthenia gravis, a polymyositis or any other type of inflammatory myopathy, as well as, a fasciitis, a fibrositis, a myositis, a neuromyotonia, a tendinosis, or a tendonitis. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 73 year old female complains of wheezing when she breathes and is diagnosed with Churg-Strauss arteritis. A physician determines that the wheezing is due to chronic inflammation. The woman is treated by oral administration a pharmaceutical composition comprising ibuprofen as disclosed herein taken twice daily. Alternatively, the woman is treated by oral administration a pharmaceutical composition comprising aspirin as disclosed herein taken thrice daily. Alternatively, the woman is treated by oral administration a pharmaceutical composition comprising naproxen as disclosed herein taken twice daily. The woman's condition is monitored and after about 3 days of treatment the woman indicates that she no longer is wheezing. At one and three month check-ups, the woman indicates that she still does not wheeze when she breathes. This reduction in a chronic inflammation symptom indicates successful treatment with the pharmaceutical composition disclosed herein. A similar type of oral administration of a pharmaceutical composition disclosed herein will be used to treat a patient suffering from chronic inflammation associated with any vasculitis, such as, e.g., a Buerger's disease, a cerebral vasculitis, a cryoglobulinemia, an essential cryoglobulinemic vasculitis, a giant cell arteritis, a Golfers vasculitis, a Henoch-Schonlein purpura, a hypersensitivity vasculitis, a Kawasaki disease, a microscopic polyarteritis/polyangiitis, a polyarteritis nodosa, a polymyalgia rheumatica (PMR), a rheumatoid vasculitis, a Takayasu arteritis, or a Wegener's granulomatosis, as well as, an arteritis, a carditis, an endocarditis, a heart disease, high blood pressure, inflammatory cardiomegaly, an ischemic heart disease, a myocarditis, a pericarditis, a phlebitis, a pylephlebitis, or a thrombophlebitis. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 37 year old male complains of skin redness and is diagnosed with rosacea. A physician determines that the redness is due to chronic inflammation. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is reduced skin redness. At one and three month check-ups, the man indicates that he continues to have improved skin tone and reduced redness This reduction in a chronic inflammation symptom indicates successful treatment with the pharmaceutical composition disclosed herein. A similar type of oral administration of a pharmaceutical composition disclosed herein will be used to treat a patient suffering from chronic inflammation associated with an acne, a cervicitis, a dermatitis, an eczema (including an atopic eczema, a contact eczema, a xerotic eczema, a seborrhoeic dermatitis, a dyshidrosis, a discoid eczema, a venous eczema, a dermatitis herpetiformis, a neurodermatitis, or an autoeczematization), an endometritis, a gingivitis, a glossitis, a hidradenitis suppurativa, a keratitis, a keratoconjunctivitis, a mastitis, a psoriasis (including a plaqure psoriasis, a nail psoriasis, a guttate psoriasis, a scalp psoriasis, an inverse psoriasis, a pustular psoriasis, or an erythrodermis psoriasis), a scleroderma, a statis dermatitis, a stomatitis, a tonsillitis, a vaginitis, a vitiligo, or a vulvitis. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 33 year old female complains of abdominal pain and diarrhea and is diagnosed with Crohn's disease. A physician determines that the abdominal pain and diarrhea is due to chronic inflammation. The woman is treated by oral administration a pharmaceutical composition comprising ibuprofen as disclosed herein taken twice daily. Alternatively, the woman is treated by oral administration a pharmaceutical composition comprising aspirin as disclosed herein taken thrice daily. Alternatively, the woman is treated by oral administration a pharmaceutical composition comprising naproxen as disclosed herein taken twice daily. The woman's condition is monitored and after about 3 days of treatment the woman indicates that there is a reduction in abdominal pain and she no longer has diarrhea. At one and three month check-ups, the woman indicates that she continues to have reduced abdominal pain and diarrhea. This reduction in a chronic inflammation symptom indicates successful treatment with the pharmaceutical composition disclosed herein. A similar type of oral administration of a pharmaceutical composition disclosed herein will be used to treat a patient suffering from neurogenic inflammation associated with any inflammatory bowel disease, such as, e.g., an ulcerative colitis (including ulcerative proctitis, left-sided colitis, pancolitis and fulminant colitis), any irritable bowel disease, as well as, a colitis, an enteritis, an enterocolitis, a gastritis, a gastroenteritis, a metabolic syndrome (syndrome X), a spastic colon, or any other gastrointestinal disorder. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 46 year old male complains of fever, joint pains, and fatigue and is diagnosed with systemic lupus erythematosus. A physician determines that these symptoms are due to chronic inflammation. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is improvement in his health, his fever is gone, the pain in his joints is reduced and his is not as tired. At one and three month check-ups, the man indicates that he continues to have reduced joint pain and does not suffer from fevers or fatigue. This reduction in a chronic inflammation symptom indicates successful treatment with the pharmaceutical composition disclosed herein. A similar type of oral administration of a pharmaceutical composition disclosed herein will be used to treat a patient suffering from chronic inflammation associated with any other systemic autoimmune disorder, including, without limitation, an anti-phospholipid antibody syndrome (APS), a bullous pemphigoid, a Chagas disease, a discoid lupus erythematosus, a drug-induced lupus erythematosus, a Goodpasture's syndrome, a Guillain-Barre syndrome, an idiopathic thrombocytopenic purpura, a myasthenia gravis, a neonatal lupus, a pernicious anemia, a polymyalgia rheumatica, a rheumatoid arthritis, a scleroderma, a Sjögren's syndrome, a subacute cutaneous lupus erythematosus, or a Wegener's granulomatosis. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 58 year old male complains of depression, sensitivity to cold, weight gain, forgetfulness, and constipation and is diagnosed with Hashimoto's thyroiditis. A physician determines that these symptoms are due to chronic inflammation. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is reduction in all the symptoms complained of. At one and three month check-ups, the man indicates that he still does not experience depression, sensitivity to cold, weight gain, forgetfulness, and constipation. This reduction in a chronic inflammation symptom indicates successful treatment with the pharmaceutical composition disclosed herein. A similar type of oral administration of a pharmaceutical composition disclosed herein will be used to treat a patient suffering from chronic inflammation associated with any other local autoimmune disorder, including, without limitation, an acute disseminated encephalomyelitis (ADEM), an Addison's disease, an autoimmune hemolytic anemia, an autoimmune hepatitis (including primary biliary cirrhosis), an autoimmune inner ear disease, a celiac disease, a Crohn's disease, a diabetes mellitus type 1, an endometriosis, a giant cell arteritis, a Graves' disease, an interstitial cystitis, a lupus nephritis, a multiple sclerosis, a morphea, a pemphigus vulgaris, a recurrent disseminated encephalomyelitis, a sclerosing cholangitis, an ulcerative colitis, or a vitiligo. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 59 year old female complains of joint stiffness and swelling and is diagnosed with reactive arthritis. A physician determines that the joint stiffness and swelling is due to chronic inflammation. The woman is treated by oral administration a pharmaceutical composition comprising ibuprofen as disclosed herein taken twice daily. Alternatively, the woman is treated by oral administration a pharmaceutical composition comprising aspirin as disclosed herein taken thrice daily. Alternatively, the woman is treated by oral administration a pharmaceutical composition comprising naproxen as disclosed herein taken twice daily. The woman's condition is monitored and after about 3 days of treatment the woman indicates there is reduced joint stiffness and swelling. At one and three month check-ups, the woman indicates that she continues to have reduced joint stiffness and swelling in the area treated. This reduction in a chronic inflammation symptom indicates successful treatment with the pharmaceutical composition disclosed herein. A similar type of oral administration of a pharmaceutical composition disclosed herein will be used to treat a patient suffering from chronic inflammation associated with any monoarthritis, oligoarthritis, or polyarthritis, such as, e.g., osteoarthritis, juvenile idiopathic arthritis, septic arthritis, a spondyloarthropathy (including ankylosing spondylitis, reactive arthritis (Reiter's syndrome), psoriatic arthritis, enteropathic arthritis associated with inflammatory bowel disease, Whipple disease or Behcet disease), a synovitis, gout, pseudogout, or Still's disease, as well as, a bursitis, a rheumatic fever, or a tenosynovitis. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A pharmaceutical composition comprising:
   a) a therapeutically effective amount of an ibuprofen;
   b) about 8% (v/v) to about 12% (v/v) of a pharmaceutically-acceptable polyethylene glycol (PEG) polymer of less than about 2,000 g/mol; and
   c) at least 60% by weight of a pharmaceutically-acceptable glycerolipid,
   wherein the pharmaceutical composition is formulated to have a melting point temperature of about 30° C. or higher.

2. The pharmaceutical composition according to claim 1, wherein the concentration of the NSAID is at least 150 mg/mL.

3. The pharmaceutical composition according to claim 1, wherein the PEG polymer comprises PEG 100, PEG 200, PEG 300, PEG 400, PEG 500, PEG 600, PEG 700, PEG 800, PEG 900, PEG 1000, or any combination thereof.

4. The pharmaceutical composition according to claim 1, wherein the glycerolipid comprises a monoglyceride, an acetylated monoglyceride, a diglyceride, an acetylated diglyceride, a triglyceride, an acetylated triglyceride, or any combination thereof.

5. The pharmaceutical composition according to claim 4, wherein the amount of the monoglyceride is at least 20% by weight of the total pharmaceutical composition.

6. The pharmaceutical composition according to claim 4, wherein the amount of the triglyceride is at least 35% by weight of the total pharmaceutical composition.

7. A method of treating an individual with a chronic inflammation, the method comprising the step of: administering to the individual in need thereof a pharmaceutical composition according to claim 1, wherein administration results in a reduction in a symptom associated with the chronic inflammation, thereby treating the individual.

8. The method according to claim 7, wherein the chronic inflammation is a tissue inflammation or a systemic inflammation.

9. The method according to claim 7, wherein the chronic inflammation is an auto-immune disease or a non-autoimmune disease.

10. The method according to claim 7, wherein the chronic inflammation is associated with an age related macular degeneration, an allergy, an allergic rhinitis, an Alzheimer's disease, an amyotrophic lateral sclerosis, an anemia, an appendicitis, an arthritis, an asthma, an atherosclerosis, an autoimmune disorder, a balanitis, a blepharitis, a bronchiolitis, a bronchitis, a bullous pemphigoid, a burn, a bursitis, a cancer, a cardiovascular disease, a cellulitis, a cervicitis, a cholangitis, a cholecystitis, a chorioamnionitis, a chronic neurogenic inflammation, a chronic obstructive pulmonary disease, a cirrhosis, a conjunctivitis, a cyclophosphamide-induced cystitis, a cystic fibrosis, a cystitis, a common cold, a dacryoadenitis, a dementia, a diabetes, a diabetic neuropathy, a diabetic retinopathy, a diabetic nephropathy, a diabetic ulcer, a digestive system disease, an emphysema, an encephalitis, an endometritis, an epicondylitis, an epididymitis, a fasciitis, a fibromyalgia, a fibrosis, a fibrositis, a gastroenteritis, a gastrointestinal disorder, a gingivitis, a glomerulonephritis, a glossitis, a graft-versus-host disease, a hepatitis, a Huntington's disease, a hyperlipidemic pancreatitis, an infection, an inflammatory neuropathy, an insulin resistance, an interstitial cystitis, an interstitial nephritis, an iritis, an ischemia, a keratitis, a keratoconjunctivitis, a laryngitis, a lupus nephritis, a mastitis, a mastoiditis, a meningitis, a metabolic syndrome, a migraine, a multiple sclerosis, a myelitis, a myopathy, a nephritis, a non-alcoholic steatohepatitis, an obesity, an omphalitis, an oophoritis, an orchitis, an osteochondritis, an osteopenia, an osteomyelitis, an osteoporosis, an osteitis, an otitis, a pancreatitis, a Parkinson's disease, a parotitis, a pelvic inflammatory disease, a pemphigus vularis, a peritonitis, a pharmacologically-induced inflammation, a pharyngitis, a pleuritis, a pneumonitis, a polycystic nephritis, a proctitis, a prostatitis, a pulpitis, a pyelonephritis, a renal failure, a reperfusion injury, a retinitis, a rheumatic fever, a rhinitis, a salpingitis, a sarcoidosis, a sialadenitis, a sinusitis, a skin disorder, a stenosis, a stomatitis, a stroke, a surgical complication, a synovitis, a tendonitis, tendinosis, a tenosynovitis, a Th1-mediated inflammatory disease, a tissue or organ injury, tonsillitis, a transplant rejection, a trauma, a traumatic brain injury, a transplant rejection, a trigonitis, a tuberculosis, a tumor, an urethritis, an ursitis, an uveitis, a vaginitis, a vasculitis, or a vulvitis.

11. The method according to claim 10, wherein the arthritis is an osteoarthritis, a rheumatoid arthritis, a juvenile idiopathic arthritis, a septic arthritis, a spondyloarthropathy, a gout, a pseudogout, or Still's disease.

12. The method according to claim 10, wherein the spondyloarthropathy is an ankylosing spondylitis, a reactive arthritis, a psoriatic arthritis, an enteropathic arthritis associated with inflammatory bowel disease, a Whipple disease or a Behcet disease.

13. The method according to claim 10, wherein the myopathy is a dermatomyositis, an inclusion body myositis, a myositis, or a polymyositis.

14. The method according to claim 10, wherein the vasculitis is a Buerger's disease, an arteritis, a cerebral vasculitis, a Churg-Strauss arteritis, a cryoglobulinemia, an essential cryoglobulinemic vasculitis, a giant cell arteritis, a Golfer's vasculitis, a Henoch-Schonlein purpura, a hypersensitivity vasculitis, a Kawasaki disease, a phlebitis, a microscopic polyarteritis/polyangiitis, a polyarteritis nodosa, a polymyalgia rheumatica, a pylephlebitis, a rheumatoid vasculitis, a Takayasu arteritis, a thrombophlebitis, a Wegener's granulomatosis, or a vasculitis secondary to connective tissue disorder, or vasculitis secondary to viral infection.

15. The method according to claim 10, wherein the skin disorder is an acne, a dermatitis, an eczema, a statis dermatitis, a hidradenitis suppurativa, a psoriasis, a rosacea or a scleroderma.

16. The method according to claim 15, wherein the eczema is an atopic eczema, a contact eczema, a xerotic eczema, a seborrhoeic dermatitis, a dyshidrosis, a discoid eczema, a venous eczema, a dermatitis herpetiformis, a neurodermatitis, or an autoeczematization.

17. The method according to claim 16, wherein the psoriasis is a plaque psoriasis, a nail psoriasis, a guttate psoriasis, a scalp psoriasis, an inverse psoriasis, a pustular psoriasis, or an erythrodermis psoriasis.

18. The method according to claim 10, wherein the gastrointestinal disorder is a celiac disease, a colitis, an enteritis, an enterocolitis, a gastritis, an ileitis, an irritable bowel disease, an inflammatory bowel disease, or a spastic colon.

19. The method according to claim 18, wherein the inflammatory bowel disease is a Crohn's disease or an ulcerative colitis.

20. The method according to claim 10, wherein the cardiovascular disease is an acid reflux/heartburn, an aneurysm, an arterial occlusive disease, a blood vessel inflammation, a cardiac arrest, a carditis, a congestive heart failure, a diabetic cardiac conditions, a dissection, an embolism, an endocarditis, a heart disease, a heart valve dysfunction, a hypertension, an inflammatory cardiomegaly, an ischemic heart disease, a myocardial infarction, a myocarditis, a pericarditis, a peripheral arterial disease, a pseudoaneurysm, a thrombosis, a thrombphlebitis, a vascular malformation, a vascular nevus, or a varicose veins.

21. The method according to claim 10, wherein the infection is a bacterial cystitis, a bacterial encephalitis, a pandemic influenza, a viral encephalitis, a viral hepatitis A, a viral hepatitis B, or a viral hepatitis C.

22. The method according to claim 7, wherein upon administration to the individual, the pharmaceutical composition results in a bio-distribution of the Ibuprofen different than a bio-distribution of the Ibuprofen included in the same pharmaceutical composition, except without the glycerolipid.

23. The method according to claim 22, wherein the amount of the ibuprofen from the pharmaceutical composition is delivered to a macrophage is at least 5% of the total amount of the ibuprofen contained in the administered pharmaceutical composition.

24. The method according to claim 7, wherein upon administration to the individual, the pharmaceutical composition reduces gastric or intestinal irritation by at least 5% when compared to the pharmaceutical composition, except without the glycerolipid.

* * * * *